United States Patent
Sanna

(10) Patent No.: US 10,039,772 B2
(45) Date of Patent: Aug. 7, 2018

(54) METHODS AND COMPOSITIONS FOR TREATING ALCOHOL USE DISORDERS

(71) Applicant: Pietro Paolo Sanna, San Diego, CA (US)

(72) Inventor: Pietro Paolo Sanna, San Diego, CA (US)

(*) Notice: Subject to any disclaimer, the term of this patent is extended or adjusted under 35 U.S.C. 154(b) by 0 days.

(21) Appl. No.: 15/350,052

(22) Filed: Nov. 12, 2016

(65) Prior Publication Data

US 2017/0232007 A1   Aug. 17, 2017

Related U.S. Application Data

(60) Provisional application No. 62/254,877, filed on Nov. 13, 2015.

(51) Int. Cl.
| | | |
|---|---|---|
| *A61K 31/585* | (2006.01) | |
| *A61K 31/56* | (2006.01) | |
| *A61K 31/4965* | (2006.01) | |
| *A61K 31/58* | (2006.01) | |

(52) U.S. Cl.
CPC ........ *A61K 31/585* (2013.01); *A61K 31/4965* (2013.01); *A61K 31/56* (2013.01); *A61K 31/58* (2013.01)

(58) Field of Classification Search
CPC .................................................. A61K 31/585
USPC ......................................................... 514/170
See application file for complete search history.

(56) References Cited

U.S. PATENT DOCUMENTS

| | | |
|---|---|---|
| 2005/0014786 A1 | 1/2005 | Sun et al. |
| 2005/0118263 A1 | 6/2005 | Walker et al. |
| 2010/0267696 A1 | 10/2010 | Webster et al. |
| 2011/0015178 A1 | 1/2011 | Webster et al. |
| 2011/0105389 A1 | 5/2011 | Hoveyda et al. |
| 2012/0095046 A1 | 4/2012 | Webster et al. |
| 2012/0135975 A1 | 5/2012 | Colandrea et al. |
| 2012/0172393 A1 | 7/2012 | Webster et al. |
| 2013/0012545 A1 | 1/2013 | Webster et al. |
| 2013/0123268 A1 | 5/2013 | Webster et al. |
| 2014/0038927 A1 | 2/2014 | Cohen et al. |

OTHER PUBLICATIONS

Wolff, Burger's medicinal Chemistry and Drug Discovery, vol. 1, Principles and Practice, John Wiley & sons, New York, 1997.*
Willebrords, Pharmacol Ther. Dec. 2017; 180: 144-160.*
Litten, Addict Biol. May 2012 ; 17(3): 513-527. doi:10.1111/j.1369-1600.2012.00454.x.*
Vendruscolo et al., Glucocorticoid receptor antagonism decreases alcohol seeking in alcohol-dependent individuals, J. Clin. Invest., 2015, 3193-3197, 125(8).
Veniant et al., Discovery of a potent, orally active 11beta-hydroxysteroid dehydrogenase type 1 inhibitor for clinical study: identification of (S)-2-((1S,2S,4R)-bicyclo[2.2.1]heptan-2-ylamino)-5-isopropyl-5-methylthiazol-4(5 H)-one (AMG 221), J. Med. Chem., 2010, 4481-4487, 53(11).
Vicker et al., A novel 18 beta-glycyrrhetinic acid analogue as a potent and selective inhibitor of 11 beta-hydroxysteroid dehydrogenase 2, Bioorg. Med. Chem. Lett., 2004, 3263-3267, 14(12).
Walker et al., Carbenoxolone increases hepatic insulin sensitivity in man: a novel role for 11-oxosteroid reductase in enhancing glucocorticoid receptor activation, J. Clin. Endocrinol. Metab., 1995, 3155-3159, 80(11).
Walker et al., Tissue production of cortisol by 11beta-hydroxysteroid dehydrogenase type 1 and metabolic disease, Ann. N.Y. Acad. Sci., 2006, 165-184, 1083.
Wamil et al., Inhibition of 11 beta-hydroxysteroid dehydrogenase type 1 as a promising therapeutic target, Drug Discov. Today, 2007, 504-520, 12(13-14).
Wan et al., Discovery of HSD-621 as a potential agent for the treatment of type 2 diabetes, 2013, ACS Med. Chem. Lett., 118-123, 4(1).
Wan et al., Efficacious 11beta-hydroxysteroid dehydrogenase type I inhibitors in the diet-induced obesity mouse model, J. Med. Chem., 2009, 5449-5461, 52(17).
Wan et al., Synthesis of potent and orally efficacious 11beta-hydroxysteroid dehydrogenase type 1 inhibitor HSD-016, J. Org. Chem., 2011, 7048-7055, 76(17).
Wang et al., Modulation of membrane channel currents by gap junction protein mimetic peptides: size matters, Am. J. Physiol. Cell Physiol., 2007, C1112-C1119, 293(3).
Wyrwoll et al., 11beta-hydroxysteroid dehydrogenases and the brain: from zero to hero, a decade of progress, Front. Neuroendocrinol., 2011, 265-286, 32(3).
Wyrwoll et al., Altered placental function of 11beta-hydroxysteroid dehydrogenase 2 knockout mice, Endocrinology, 2009,1287-1293, 150(3).
Wyrwoll et al., Altered placental methyl donor transport in the dexamethasone programmed rat, Placenta, 2012, 220-223, 33(3).
Xiang et al., Piperazine sulfonamides as potent, selective, and orally available 11beta-hydroxysteroid dehydrogenase type 1 inhibitors with efficacy in the rat cortisone-induced hyperinsulinemia model, J. Med. Chem., 2008, 4068-4071, 51(14).

(Continued)

*Primary Examiner* — Nizal S Chandrakumar
(74) *Attorney, Agent, or Firm* — Procopio, Cory, Hargreaves & Savitch LLP; Lisel M. Ferguson

(57) ABSTRACT

Disclosed are methods and compositions for treating alcohol dependence by administration to a patient of an inhibitor of 11β-hydroxysteroid dehydrogenases (11β-HSD) to modulate glucocorticoid effects. One such compound is the 11β-HSD inhibitor carbenoxolone (18β-glycyrrhetinic acid 3β-O-hemisuccinate), which has been extensively employed in the clinic for the treatment of gastritis and peptic ulcer. Carbenoxolone is active on both 11β-HSD1 and 2 isoforms. Here, carbenoxolone is surprisingly shown to reduce both baseline and excessive drinking in rats and mice. The carbenoxolone diastereomer 18α-glycyrrhetinic acid 3β-O-hemisuccinate (αCBX), which the applicants discovered to be selective for 11β-HSD2, was also effective in reducing alcohol drinking in mice. Thus, 11β-HSD inhibitors are a new class of candidate alcohol abuse medications and existing 11β-HSD inhibitor drugs may be re-purposed for alcohol abuse treatment.

15 Claims, 6 Drawing Sheets

(56) References Cited

OTHER PUBLICATIONS

Xiang et al., Synthesis and biological evaluation of sulfonamidooxazoles and beta-keto sulfones: selective inhibitors of 11beta-hydroxysteroid dehydrogenase type I, Bioorg. Med. Chem. Lett., 2005, 2865-2869, 15(11).
Yan et al., The synthesis and SAR of novel diarylsulfone 11beta-HSD1 inhibitors, Bioorg. Med. Chem. Lett., 2010, 7071-7075, 20(23).
Zhang et al., Inhibition of 11 beta-hydroxysteroid dehydrogenase obtained from guinea pig kidney by furosemide, haringenin and some other compounds, J. Steroid Biochem. Mol. Biol., 1994, 81-85, 49(1).
Zhang et al., Inhibition of 11beta-hydroxysteroid dehydrogenase type II selectively blocks the tumor COX-2 pathway and suppresses colon carcinogenesis in mice and humans, 2009, J. Clin. Invest., 2009, 876-885, 119(4).
Zhu et al., 4-Methyl-5-phenyl triazoles as selective inhibitors of 11beta-hydroxysteroid dehydrogenase type I, Bioorg. Med. Chem. Lett., 2008, 3405-3411, 18(11).
Zhu et al., Activity-based exposure comparisons among humans and nonclinical safety testing species in an extensively metabolized drug candidate, Xenobiotica, 2013, 617-627, 43(7).
Zhu et al., Phenylcyclobutyl triazoles as selective inhibitors of 11beta-hydroxysteroid dehydrogenase type I, Bioorg. Med. Chem. Lett., 2008, 3412-3416, 18(11).
Adinoff et al., Increased salivary cortisol concentrations during chronic alcohol intoxication in a naturalistic clinical sample of men, Alcohol. Clin. Exp. Res., 2003, 1420-1427, 27(9).
Alberts et al., Selective inhibition of 11beta-hydroxysteroid dehydrogenase type 1 decreases blood glucose concentrations in hyperglycaemic mice, Diabetologia, 2002, 1528-1532, 45(11).
Andrews et al., Effects of the 11β-Hydroxysteroid Dehydrogenase Inhibitor Carbenoxolone on Insulin Sensitivity in Men with Type 2 Diabetes, J. Clin. Endocrinol. Metab., 2003, 285-291, 88(1).
Armanini et al., Pseudohyperaldosteronism: pathogenetic mechanisms, Crit. Rev. Clin. Lab. Sci., 2003, 295-335, 40(3).
Armanini et al., The mechanism of mineralocorticoid action of carbenoxolone, Endocrinology, 1982, 1683-1686, 111(5).
Armanini et al., The pathogenesis of pseudohyperaldosteronism from carbenoxolone, J. Endocrinol. Invest., 1989, 337-341, 12(5).
Aster et al., Bis-aryl triazoles as selective inhibitors of 11beta-hydroxysteroid dehydrogenase type 1, Bioorg. Med. Chem. Lett., 2008, 2799-2804, 18(9).
Baker, Evolution of 11beta-hydroxysteroid dehydrogenase-type 1 and 11beta-hydroxysteroid dehydrogenase-type 3, FEBS Lett., 2010, 2279-2284, 584(11).
Barf et al., Arylsulfonamidothiazoles as a new class of potential antidiabetic drugs. Discovery of potent and selective inhibitors of the 11beta-hydroxysteroid dehydrogenase type 1, J. Med. Chem., 2002, 3813-3815, 45(18).
Becker et al., Increased ethanol drinking after repeated chronic ethanol exposure and withdrawal experience in C57BL/6 mice, Alcohol. Clin. Exp. Res., 2004, 1829-1838, 28(12).
Beraki et al., A pharmacological screening approach for discovery of neuroprotective compounds in ischemic stroke, PLoS One, 2013, e69233, 8(7) (13 pages).
Berrettini, Opioid Pharmacogenetics of Alcohol Addiction, Perspect. Med., 2013, 1-9, 3(7).
Bertaccini et al., Pharmacology of the treatment of peptic ulcer disease, Dig. Dis. Sci., 1985, 43S-51S, 30(11 Suppl.).
Beseda et al., Synthesis of glycyrrhetinic acid derivatives for the treatment of metabolic diseases, Bioorg. Med. Chem., 2010, 433-454, 18(1).
Bhat et al., Demonstration of proof of mechanism and pharmacokinetics and pharmacodynamic relationship with 4'-cyano-biphenyl-4-sulfonic acid (6-amino-pyridin-2-yl)amide (PF-915275), an inhibitor of 11-hydroxysteroid dehydrogenase type 1, in cynomolgus monkeys, J. Pharmacol. Exp. Ther., 2008, 299-305, 324(1).
Bruzzone et al., Pharmacological properties of homomeric and heteromeric pannexin hemichannels expressed in Xenopus oocytes, J. Neurochem., 2005, 1033-1043, 92(5).
Chantong et al., Mineralocorticoid and glucocorticoid receptors differentially regulate NF-kappaB activity and pro-inflammatory cytokine production in murine BV-2 microglial cells, J. Neuroinflammation, 2012, 260, 9 (14 pages).
Chapman et al., 11β-Hydroxysteroid Dehydrogenases: Intracellular Gate-Keepers of Tissue Glucocorticoid Action, Physiol. Rev., 2013, 1139-1206, 93(3).
Cheng et al., The development and SAR of pyrrolidine carboxamide 11beta-HSD1 inhibitors, Bioorg. Med. Chem. Lett., 2010 2897-2902, 20(9).
Classen-Houben et al., Selective inhibition of 11beta-hydroxysteroid dehydrogenase 1 by 18alpha-glycyrrhetinic acid but not 18beta-glycyrrhetinic acid, J. Steroid Biochem. Mol. Biol., 2009, 248-252, 113(3-5).
Coppola et al., Perhydroquinolylbenzamides as novel inhibitors of 11beta-hydroxysteroid dehydrogenase type 1, J. Med. Chem., 2005, 6696-6712, 48(21).
Cotrell et al., Foetal and placental 11beta-HSD2: a hub for developmental programming, Acta Physiol. (Oxf), 2014, 288-295, 210(2).
Dahl et al., The bizarre pharmacology of the ATP release channel pannexin1, Neuropharmacology, 2013, 583-593,75.
Di Stefano et al., Diphenylamine-2-carboxylate, a blocker of the Cl(−)-conductive pathway in Cl(−)-transporting epithelia, Pflugers Arch., 1985, S95-S100, 405 Suppl. 1.
Draper et al., 11beta-hydroxysteroid dehydrogenase and the pre-receptor regulation of corticosteroid hormone action, J. Endocrinol., 2005, 251-271, 186(2).
Duan et al., Design, synthesis, and biological evaluation of 1,4-diaryl-1,4-dihydropyrazines as novel 11beta-HSD1 inhibitors, Biol. Pharm. Bull., 2014, 840-846, 37(5).
Farese et al., Glycyrrhetinic acid food supplementation lowers serum potassium concentration in chronic hemodialysis patients, 2009, Kidney Int., 877-884, 76(8).
Ferrari, The role of 11beta-hydroxysteroid dehydrogenase type 2 in human hypertension, Biochim. Biophys. Acta, 2010, 1178-1187, 1802(12).
Flyren et al., Piperidine amides as 11beta-hydroxysteroid dehydrogenase type 1 inhibitors, Bioorg. Med. Chem. Lett., 2007, 3421-3425, 17(12).
Fotsch et al., Further studies with the 2-amino-1,3-thiazol-4(5H)-one class of 11beta-hydroxysteroid dehydrogenase type 1 inhibitors: reducing pregnane X receptor activity and exploring activity in a monkey pharmacodynamic model, 2008, J. Med. Chem., 7953-7967, 51(24).
Gareri et al., Anticonvulsant effects of carbenoxolone in genetically epilepsy prone rats (GEPRs), Neuropharmacology, 2004, 1205-1216, 47(8).
Gareri et al., Influence of carbenoxolone on the anticonvulsant efficacy of conventional antiepileptic drugs against audiogenic seizures in DBA/2 mice, Eur. J. Pharmacol., 2004, 49-56, 484(1).
Gaware et al., Synthesis of new glycyrrhetinic acid derived ring A azepanone, 29-urea and 29-hydroxamic acid derivatives as selective 11beta-hydroxysteroid dehydrogenase 2 inhibitors, Bioorg. Med. Chem., 2011, 1866-1880, 19(6).
Gilpin et al., Operant behavior and alcohol levels in blood and brain of alcohol-dependent rats, Alcohol. Clin. Exp. Res., 2009, 2113-2123, 33(12).
Goldberg et al., Free-Wilson and structural approaches to co-optimizing human and rodent isoform potency for 11beta-hydroxysteroid dehydrogenase type 1 (11beta-HSD1) inhibitors, 2012, J. Med. Chem., 10652-10661, 55(23).
Gu et al., Discovery of 4-heteroarylbicyclo[2.2.2]octyltriazoles as potent and selective inhibitors of 11beta-HSD1: novel therapeutic agents for the treatment of metabolic syndrome, Bioorg. Med. Chem. Lett., 2005, 5266-5269, 15(23).
Hale et al., Development of 11beta-HSD1 inhibitors for the treatment of type 2 diabetes, Mini. Rev. Med. Chem., 2008, 702-710, 8(7).

(56) References Cited

OTHER PUBLICATIONS

Hale et al., Structural characterization and pharmacodynamic effects of an orally active 11beta-hydroxysteroid dehydrogenase type 1 inhibitor, Chem. Biol. Drug Des., 2008, 36-44, 71(1).
Heilig et al., Pharmacogenetic approaches to the treatment of alcohol addiction, Nat. Rev. Neurosci., 2011, 670-684, 12(11).
Hermanowski-Vosatka et al., 11beta-HSD1 inhibition ameliorates metabolic syndrome and prevents progression of atherosclerosis in mice, J. Exp. Med., 2005, 517-527, 202(4).
Hofer et al., Synthesis and biological analysis of benzazol-2-yl piperazine sulfonamides as 11beta-hydroxysteroid dehydrogenase 1 inhibitors, Bioorg. Med. Chem. Lett., 2013, 5397-5400, 23(19).
Jo et al., Inhibition of neuronal voltage-gated sodium channels by brilliant blue G,. Mol. Pharmacol., 2011, 247-257, 80(2).
Julian et al., Discovery of novel, potent benzamide inhibitors of 11beta-hydroxysteroid dehydrogenase type 1 (11beta-HSD1) exhibiting oral activity in an enzyme inhibition ex vivo model, J .Med. Chem., 2008, 3953-3960, 51(13).
Koob et al., Neurocircuitry of addiction, Neuropsychopharmacology, 2010,:217-238, 35(1).
Kratschmar et al., Characterization of activity and binding mode of glycyrrhetinic acid derivatives inhibiting 11beta-hydroxysteroid dehydrogenase type 2, J. Steroid Biochem Mol. Biol., 2011, 129-142, 125(1-2).
Leschchenko et al., Carbenoxolone does not cross the blood brain barrier: an HPLC study, BMC Neurosci., 2006, 3, 7 (3 pages).
Litten et al., Medications Development to Treat Alcohol Dependence: A Vision for the Next Decade, Addict. Biol., 2012, 513-527, 17(3).
Lopez et al., Effect of pattern and numver of chronic ethanol exposures on subsequent voluntary ethanol intake in C57BL/67 mice, Psychopharmacology (Berl.), 2005, 688-696, 181(4).
Lovallo et al., Blunted stress cortisol response in abstinent alcoholic and polysubstance-abusing men, Alcohol. Clin. Exp. Res., 2000, 651-658, 24(5).
Maletic et al., Bicyclo[2.2.2]octyltriazole inhibitors of 11beta-hydoxysteroid dehydrogenase type 1. Pharmacological agents for the treatment of metabolic syndrome, Bioorg. Med. Chem. Lett., 2011, 2568-2572, 21(8).
Mason et al., Acamprosate for alcohol dependence: a sex-specific meta-analysis based on individual patient data, Alcohol. Clin. Exp. Res., 2012, 497-508, 36(3).
Mason et al., Gabapentin Treatment for Alcohol Dependence: A Randomized Clinical Trial, JAMA Intern. Med., 2013, 70-77, 174(1).
McCoull et al., Identification and optimisation of 3,3-dimethyl-azetidin-2-ones as potent and selective inhibitors of 11β-hydroxysteroid dehydrogenase type 1 (11β-HSD1), Med. Chem. Comm., 2014, 57-63, 5(1).
McMinn et al., Optimization of novel di-substituted cyclohexylbenzamide derivatives as potent 11 beta-HSD1 inhibitors, Bioorg. Med. Chem. Lett., 2009, 1446-1450, 19(5).
Mohler et al., Acute inhibition of 11beta-hydroxysteroid dehydrogenase type-1 improves memory in rodent models of cognition, J. Neurosci., 2011, 5406-5413, 31(14).
Nair et al., N-(Pyridin-2-yl) arylsulfonamide inhibitors of 11beta-hydroxysteroid dehydrogenase type 1: strategies to eliminate reactive metabolites, Bioorg. Med. Chem. Lett., 2013, 2344-2348, 23(8).
Nuotio-Antar et al., Carbenoxolone treatment attenuates symptoms of metabolic syndrome and atherogenesis in obese, hyperlipidemic mice, Am. J. Physiol. Endocrinol. Metab., 2007, E1517-E1528, 293(6).
Odermatt et al., Tissue-specific modulation of mineralocorticoid receptor function by 11beta-hydroxysteroid dehydrogenases: an overview, Mol. Cell Endocrinol., 168-186, 350(2).
Olson et al., Adamantyl triazoles as selective inhibitors of 11beta-hydroxysteroid dehydrogenase type 1, Bioorg. Med. Chem. Lett., 2005, 4359-4362, 15(19).

Pandya et al., Synthesis of sterically encumbered 11beta-aminoprogesterone derivatives and evaluation as 11beta-hydroxysteroid dehydrogenase inhibitors and mineralocorticoid receptor antagonists, Bioorg. Med. Chem., 2013, 6274-6281, 21(21).
Piazza et al., Glucocorticoids as a biological substrate of reward: physiological and pathophysiological implications, Brain Res. Brain Res. Rev., 1997, 359-372, 25(3).
Qiu et al., A permeant regulating its permeation pore: inhibition of pannexin 1 channels by ATP, Am. J. Physiol. Cell Physiol., 2009, C250-C255, 296(2).
Rasmussen et al., Chronic daily ethanol and withdrawal: 1. Long-term changes in the hypothalamo-pituitary-adrenal axis, Alcohol. Clin. Exp. Res., 2000, 1836-1849, 24(12).
Rew et al., Discovery and optimization of benzenesulfonanilide derivatives as a novel class of 11beta-HSD1 inhibitors, Bioorg. Med. Chem. Lett., 2012, 3786-3790, 22(11).
Rew et al., Discovery and optimization of piperidyl benzamide derivatives as a novel class of 11beta-HSD1 inhibitors, Bioorg. Med. Chem. Lett., 2009, 1797-1801, 19(6).
Rhodes et al., Evaluation of a simple model of ethanol drinking to intoxication in C57BL/6J mice, Physiol. Behav., 2005, 53-63, 84(1).
Rhodes et al., Mouse inbred strain differences in ethanol drinking to intoxication, Genes Brain. Behav., 2007, 1-18, 6(1).
Richardson et al., Alcohol self-administration acutely stimulates the hypothalamic-pituitary-adrenal axis, but alcohol dependence leads to a dampened neuroendocrine state, Eur. J. Neurosci., 2008, 1641-1653, 28(8).
Rimondini et al., A temporal threshold for induction of persistent alcohol preference: behavioral evidence in a rat model of intermittent intoxication, J. Stud. Alcohol., 2003, 445-449, 64(4).
Roberts et al., Excessive ethanol drinking following a history of dependence: animal model of allostasis, Neuropsychopharmacology, 2000, 581-594, 22(6).
Rohde et al., Discovery and metabolic stabilization of potent and selective 2-amino-N-(adamant-2-yl) acetamide 11beta-hydroxysteroid dehydrogenase type 1 inhibitors, J. Med. Chem., 2007, 149-164, 50(1).
Sakamuri et al., Carbenoxolone treatment ameliorated metabolic syndrome in WNIN/Ob obese rats, but induced severe fat loss and glucose intolerance in lean rats, PLoS One, 2012, e50216, 7(12) (16 pages).
Samhsa, Substance Abuse and Mental Health Services Administration, Results from the 2012 National Survey on Drug Use and Health: Summary of National Findings, NSDUH Series H-46, HHS Publication No. (SMA) 13-4795, 2013, p. 1-164, Rockville, MD, USA, doi: http://archive.samhsa.gov/data/NSDUH/2012SummNatFindDetTables/NationalFindings/NSDUHresults2012.pdf.
Sandeep et al., 11Beta-hydroxysteroid dehydrogenase inhibition improves cognitive function in healthy elderly men and type 2 diabetics, Proc. Natl. Acad. Sci. U.S.A., 2004, 6734-6739, 101(17).
Schulteis et al., Decreased brain reward produced by ethanol withdrawal, Proc. Natl. Acad. Sci., USA, 1995, 5880-5884, 92(13).
Schuster et al., The discovery of new 11beta-hydroxysteroid dehydrogenase type 1 inhibitors by common feature pharmacophore modeling and virtual screening, J. Med. Chem., 2006, 3454-3466, 49(12).
Scott et al., Discovery of a potent, selective, and orally bioavailable acidic 11beta-hydroxysteroid dehydrogenase type 1 (11beta-HSD1) inhibitor: discovery of 2-[(3S)-1-[5-(cyclohexylcarbamoyl)-6-propylsulfanylpyridin-2-yl]-3-piperidyl]acet ic acid (AZD4017), J. Med. Chem., 2012, 5951-5964, 55(12).
Scott et al., Medicinal Chemistry of Inhibitors of 11beta-Hydroxysteroid Dehydrogenase Type 1 (11beta-HSD1), J. Med. Chem., 2014, 4466-4486, 57(11).
Scott et al., Optimisation of pharmacokinetic properties in a neutral series of 11beta-HSD1 inhibitors, Bioorg. Med. Chem. Lett., 2012, 6756-6761, 22(21).
Scott et al., Reduction of acyl glucuronidation in a series of acidic 11β-hydroxysteroid dehydrogenase type 1 (11β-HSD1) inhibitors: the discovery of AZD6925, 2012, J. Med. Chem., 10136-10347, 55(22).

(56) References Cited

OTHER PUBLICATIONS

Shah et al., Azabicyclic sulfonamides as potent 11beta-HSD1 inhibitors, Bioorg. Med. Chem. Lett., 2010, 1551-1554, 20(5).

Silverman et al., Probenecid, a gout remedy, inhibits pannexin 1 channels, Am. J. Physiol. Cell Physiol., 2008, C761-C767, 295(3).

Silverman et al., The pannexin 1 channel activates the inflammasome in neurons and astrocytes, J. Biol. Chem., 2009, 18143-18151, 284(27).

Sinha et al., Effects of adrenal sensitivity, stress- and cue-induced craving, and anxiety on subsequent alcohol relapse and treatment outcomes, Arch. Gen. Psychiatry, 2011, 942-952, 68(9).

Siu et al., N-(Pyridin-2-yl) arylsulfonamide inhibitors of 11beta-hydroxysteroid dehydrogenase type 1: Discovery of PF-915275, Bioorg. Med. Chem. Lett., 2009, 3493-3497, 19(13).

Sprow et al., The neurobiology of binge-like ethanol drinking: Evidence from rodent models, Physiol. Behav., 2012, 325-301, 106(3).

St Jean et al., 2-(S)-phenethylaminothiazolones as potent, orally efficacious inhibitors of 11beta-hydroxysteriod dehydrogenase type 1, J. Med. Chem., 2007, 429-432, 50(3).

Stanetty et al., Synthesis of novel 3-amino and 29-hydroxamic acid derivatives of glycyrrhetinic acid as selective 11beta-hydroxysteroid dehydrogenase 2 inhibitors, Bioorg. Med. Chem., 2010, 7522-7541, 18(21).

Stewart et al., Mineralocorticoid activity of carbenoxolone: contrasting effects of carbenoxolone and liquorice on 11beta-hydroxysteroid dehydrogenase activity in man, Clin. Sci. (Lond), 1990, 49-54, 78(1).

Su et al., Inhibition of human and rat 11beta-hydroxysteroid dehydrogenase type 1 by 18beta-glycyrrhetinic acid derivatives, J. Steroid Biochem. Mol. Biol., 2007, 312-320, 104(3-5).

Su et al., Novel 18beta-glycyrrhetinic acid analogues as potent and selective inhibitors of 11beta-hydroxysteroid dehydrogenases, Bioorg. Med. Chem., 2004, 4439-4457, 12(16).

Sun et al., Discovery and initial SAR of arylsulfonylpiperazine inhibitors of 11beta-hydroxysteroid dehydrogenase type 1 (11beta-HSD1), Bioorg. Med. Chem. Lett., 2008, 3513-3516, 18(12).

Sun et al., Small molecule 11beta-hydroxysteroid dehydrogenase type 1 inhibitors, Curr. Top. Med. Chem., 2011, 1464-1475, 11(12).

Sun et al., Substituted phenyl triazoles as selective inhibitors of 11beta-Hydroxysteroid Dehydrogenase Type 1, Bioorg. Med. Chem. Lett., 2011, 2141-2145, 21(7).

Sun et al., Synthesis and optimization of novel 4,4-disubstituted cyclohexylbenzamide derivatives as potent 11beta-HSD1 inhibitors, Bioorg. Med. Chem. Lett., 2011, 405-410, 21(1).

Sutin et al., Oxazolones as potent inhibitors of 11beta-hydroxysteroid dehydrogenase type 1, Bioorg. Med. Chem. Lett., 2007, 4837-4840, 17(17).

Tiwari, INCB-13739, an 11beta-hydroxysteroid dehydrogenase type 1 inhibitor for the treatment of type 2 diabetes, IDrugs, 2010, 266-275, 13(4).

Turpie et al., Carbenoxolone sodium in the treatment of gastric ulcer with special reference to side-effects, Gut, 1965, 591-594, 6(6).

Uhart et al., Stress, alcohol and drug interaction: an update of human research, Addict. Biol., 2009, 43-64, 14(1).

Vendruscolo et al., Corticosteroid-dependent plasticity mediates compulsive alcohol drinking in rats, J. Neurosci., 2012, 7563-7571, 32(22).

Vendruscolo et al., "Operant alcohol self-administration in dependent rats: focus on the vapor model", Alcohol. (2014) 48(3):277-286.

International Search Report and Written Opinion for related International Application No. PCT/US2016/061729, dated Feb. 21, 2017, in 7 pages.

* cited by examiner

Figure 1 A-C
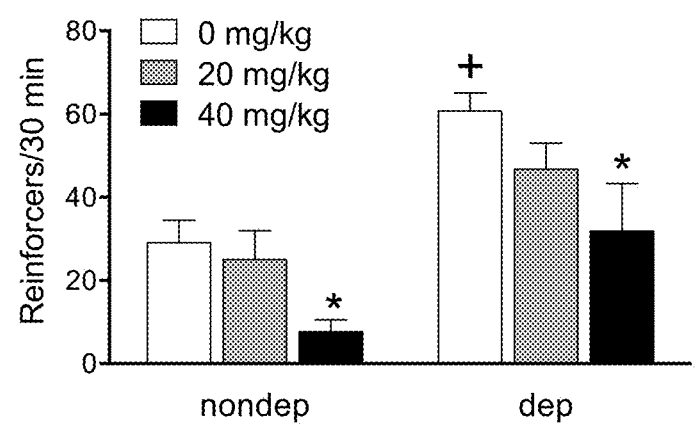
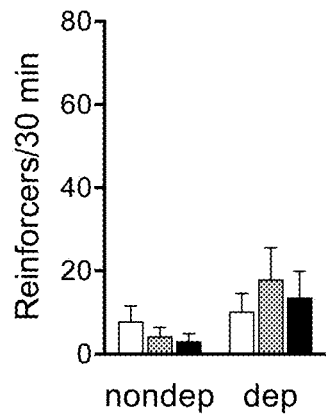
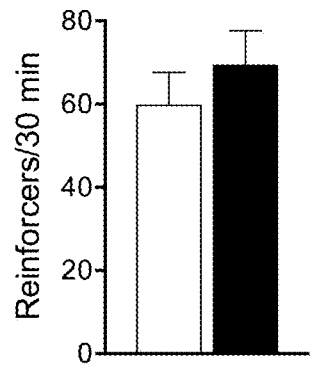

METHODS AND COMPOSITIONS FOR TREATING ALCOHOL USE DISORDERS

RELATED APPLICATION

This application claims the benefit of priority to Application Ser. No. 62/254,877 filed 13 Nov. 2015, supported by a grant from the U.S. Government (NIH grant no. AA021667). The government may have certain rights in the invention.

STATEMENT REGARDING FEDERALLY SPONSORED RESEARCH

Work relating to this application was supported by a grant from the U.S. Government (NIH grant no. AA021667). The government may have certain rights in the invention.

FIELD OF THE INVENTION

This invention relates to treatment methods and compositions for ameliorating substance use disorders, abuse, and/or dependence. More specifically, this invention relates to treatment methods and compositions for reducing excessive intake of substances such as alcohol.

BACKGROUND OF THE INVENTION

1. Introduction

The following description in this Background section includes information that may be useful in understanding the present invention. It is not an admission that any such information is prior art, or relevant, to the presently claimed inventions, or that any publication specifically or implicitly referenced is prior art. In this specification, a number of documents including patent applications are cited. The disclosures of these documents, while not considered relevant for the patentability of this invention, are hereby incorporated by reference in their entirety. More specifically, all referenced documents are incorporated by reference to the same extent as if each individual document was specifically and individually indicated to be incorporated by reference.

2. Background

In the United States, with an estimated 6.8 percent of the population aged 12 or older classified as having alcohol dependence or abuse (1), alcohol remains the most prevalent abused substance in the USA (1). Few pharmacotherapies for alcohol abuse are currently available, and those that exist have shown only limited efficacy, poor patient compliance, etc. (2-4). Thus, the development of more efficacious and safe alcohol abuse/dependence medications is a significant unmet medical need (5).

Carbenoxolone (3β-hydroxy-11-oxoolean-12-en-30-oic acid 3-hemisuccinate) is the hemisuccinate derivative of 18β-glycyrrhetinic acid (GA), a metabolite of the natural product glycyrrhizin present in licorice (6). Carbenoxolone has long been used for the treatment of gastritis and peptic ulcers (7). Subsequent studies focused on elucidating the mechanism of action of carbenoxolone have highlighted that carbenoxolone modulates glucocorticoid metabolism in target tissues by inhibiting 11β-hydroxysteroid dehydrogenases (11β-HSD) (8) and, at potencies several orders of magnitude higher, gap junction communication (9). 11β-HSD interconverts 11-hydroxi (active) glucocorticoids (cortisol in humans and corticosterone in rodents) and inert 11-keto glucocorticoids (cortisone in humans and 11β-dehydrocorticosterone in rodents) in target cells, thus acting as pre-receptor (8). In particular, there are at least two known isozymes of 11β-HSD: type 1 (11β-HSD1) and type 2 (11β-HSD2). In vivo, 11β-HSD1 catalyses the regeneration of cortisol in humans and corticosterone in rodents from cortisone in humans and 11β-dehydrocorticosterone in rodents using the cofactor NADPH, while 11β-HSD2 catalyses the reverse reaction using the cofactor NAD+ (8). An 11β-HSD3 isozyme has also been described, whose physiological function remains unclear (10). Carbenoxolone inhibits 11β-HSD isozymes in an isozyme non-selective manner (11).

Glucocorticoids are key in the regulation of stress responses, carbohydrate, lipid and protein metabolism and turnover, blood pressure, cell growth and differentiation, neuronal and immune functions, and alcohol and drug abuse (12-14). A complex regulatory network is involved in the regulation of glucocorticoid actions, with 11β-HSD enzymes regulating intracellular glucocorticoid levels and receptor access (8).

Impaired glucocorticoid regulation has been implicated in the pathogenesis of several diseases and, thus, modulation of intracellular glucocorticoid levels is a potential therapeutic strategy to treat glucocorticoid-dependent diseases. 11β-HSD1 is expressed primarily in the liver, brain, and adipose tissue (8). Inhibition of 11β-HSD1 reduces the intracellular availability of active glucocorticoids such as cortisol in humans and corticosterone in rodents (8). In both humans and rodents, elevated 11β-HSD1 activity has been associated with metabolic disorders (9, 15-18) and age-related cognitive impairments (19, 20). 11β-HSD2 is expressed in classic mineralocorticoid target tissues including the kidney, colon, sweat and salivary glands (21). 11β-HSD2 is also expressed in the placenta, where it protects the fetus from excess glucocorticoids (22-24), as well as in inflamed tissue and several tumors and cancer cell lines (21). Inhibition of 11β-HSD2 is responsible for the adverse effects of enhanced renal sodium retention and elevated blood pressure in patients with mutations of HSD11B2 (25) and in individuals ingesting high amounts of licorice, which contains the non-selective 11β-HSD inhibiting triterpenoid glycyrrhetinic acid (GA) and in some patients treated with the non-selective 11β-HSD inhibitor carbenoxolone (26-28). However, recent evidence indicates potential beneficial effects of 11β-HSD2 inhibition in chronic inflammatory diseases of the colon and on colon cancer cell proliferation. In particular, 11β-HSD2 regulates the activity of several enzymes involved in inflammatory and other responses such as NfKB (29) and COX (30). Furthermore, a recent clinical study suggested that 11β-HSD2 inhibition promotes potassium excretion and prevents hyperkalemia in chronic hemodialysis patients (31). Thus, 11β-HSD2 inhibition may also be therapeutically useful.

It is also understood that alcohol use disrupts glucocorticoid regulation in rodents (32, 33) as well as humans (34-37). Regardless of what is known about the functional consequences of such a dysregulation, there is a significant lack of understanding regarding this particular regulation cascade. However, it has been reported that glucocorticoid activation by alcohol is associated with escalation of alcohol intake in dependent rats and alcohol-seeking and drinking during protracted abstinence (13). In that study, mifepristone (RU38486), a glucocorticoid receptor antagonist with progesterone partial agonist activity, was used to antagonize glucocorticoid activation and the blocking of activation by systemic glucocorticoid receptor (GR) antagonism blocked escalated alcohol drinking and compulsive response for alcohol (35). In still another study, in humans, high adrenal sensitivity, as expressed by a high cortisol to corticotropin ratio at rest (neutral, relaxed conditions), was found to correlate with greater susceptibility of relapse to heavy drinking (37).

Only a limited number of drugs exist with clinical efficacy for alcohol abuse (5). Expansion of available therapeutic options is needed to improve treatment success at different stages of disease progression and, optimally, to bring about individualized therapies based on patient genetic makeup and disease stage (5, 38). Given that there is an ongoing need for effective medications for treating and ameliorating substance use disorder, abuse, and/or dependence for substances such as alcohol, this invention provides a new solution for treating alcohol substance abuse through the novel discovery that compounds capable of inhibiting 11β-hydroxysteroid dehydrogenases (11β-HSD) can be used to ameliorate excessive alcohol intake.

Thus, as described below, methods and compositions are provided for reducing dependence and otherwise excessive intake of alcohol in mammals including humans.

SUMMARY OF THE INVENTION

In a first aspect, the invention relates to new and more effective treatment methods for treating mammals, particularly humans, for alcohol use disorders, abuse, and/or dependence.

In a second aspect, the invention concerns compositions for treating alcohol use disorders, abuse, and/or dependence. In preferred embodiments, such compositions comprise formulations of an inhibitor of 11β-hydroxysteroid dehydrogenase (11β-HSD) activity, such as, for example, carbenoxolone or a carbenoxolone derivatives, or other such inhibitors as described herein.

In a third aspect, the invention involves methods for reducing alcohol use disorders, abuse, and/or dependence by administering to a mammal (particularly a human) in need thereof an effective amount of an inhibitor of 11β-hydroxysteroid dehydrogenases (11β-HSD) activity, such as by administration of a carbenoxolone formulation to cause inhibition of 11β-hydroxysteroid dehydrogenases (11β-HSD) activity, thereby resulting in a reduction of alcohol intake in the mammal.

Other features and advantages of the invention will be apparent from the following description and from the claims. The invention will be further described in the following examples, which do not limit the scope of the invention described in the claims.

BRIEF DESCRIPTION OF THE DRAWINGS

FIG. 1A is a graph showing acute, systemic administration of carbenoxolone decreases in alcohol self-administration both in dependent and nondependent rats. FIGS. 1B and 1C are graphs showing acute, systemic administration of carbenoxolone does not affect self-administration of saccharin-sweetened water. A) Acute, systemic administration of CBX decreases operant alcohol self-administration both in dependent and non-dependent rats. B) CBX did not influence water intake in any group. C) Acute, systemic administration of CBX does not affect operant self-administration of saccharin-sweetened water. Rats were given CBX (0, 20, and 40 mg/kg or 0 and 40 mg/kg; IP) 90 min prior to alcohol (10%, w/v), water or saccharin (0.004%) self-administration (30 min session; FR1). The data represent means and SEM. *p<0.05, significant difference from respective vehicle; $^+$p<0.05, significant difference from vehicle (saline)-treated non-dependent rats. N=9-10 per group.

DETAILED DESCRIPTION OF THE INVENTION

Figure 2:
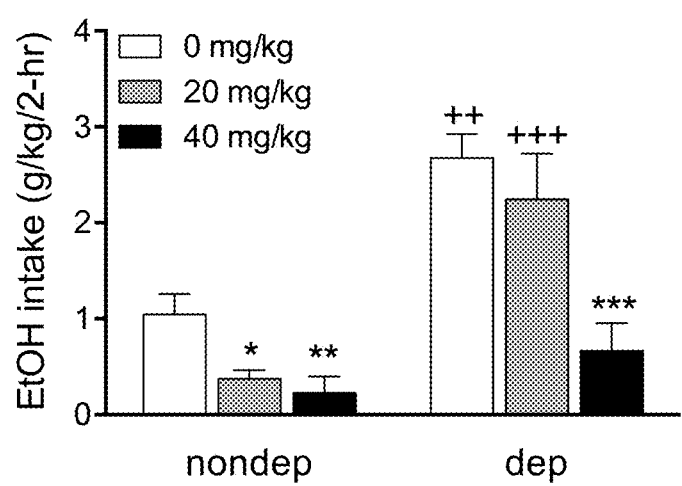
FIG. 2 is a graph showing acute CBX reduces ethanol intake in non-dependent and dependent mice in a limited access 2-bottle choice paradigm. Mice trained to drink alcohol in a limited access (2 h) 2-bottle choice paradigm were either exposed to alcohol vapor to induce dependence or air for the purpose of control, and tested for the effect of CBX on drinking. CBX reduced ethanol intake in non-dependent mice at doses of 20 and 40 mg/kg IP (left), and in dependent mice at 40 mg/kg, IP (right). Two-way ANOVA revealed a significant effect of vapor exposure ($F_{2,35}$=33.38, p<0.0001), dose ($F_{2,35}$=13.04, p<0.0001), and interaction of vapor exposure and dose ($F_{2,35}$=3.902, p=0.0295). *p<0.05, p<0.01, *p<0.001, significant difference from the respective vehicle saline-treated group; $^{++}$p<0.01, $^{+++}$p<0.001, significant difference from respective non-dependent group.

Turning now to the invention, provided are methods and compositions for treating alcohol use disorders, abuse, and/or dependence. This invention is based on the surprising discovery that compounds that have an antagonizing effect on 11β-HSD, in its various forms, when administered to a mammal, particularly a human, there is induced a reduction in alcohol intake in the subject. In one example, administration of carbenoxolone, having an antagonizing effect on 11β-HSD, reduces the intake behavior of alcohol in test mammals.

The term "treating" refers to any indication of success in the treatment or amelioration of a pathology or condition, including any objective or subjective parameter such as abatement; remission, decrease of symptoms in the pathology or condition so as to make physical conditions more tolerable to the patient. The term "treating" also refers to the lessening of negative effects of the pathology or condition making the final point of efficacy less debilitating so as to improve a patient's physical well-being.

Inhibition of 11β-HSD "synthesis or activity" refers to the inhibition of 11β-HSD at the protein level, to prevent or down-regulate the production of the protein, and/or at least one biological activity of any protein produced.

Regarding the activity of 11β-HSD, any small molecule, nucleic acid such as an interfering RNA, enzyme or protein that increases activity is necessarily an agonist of that activity. Similarly, any small molecule, nucleic acid, enzyme or protein that reduces the activity is an antagonist, i.e., inhibitor. Thus, the substance disclosed in the methods and compositions below is an antagonist of 11β-HSD, i.e., is capable of decreasing or reducing the activity of 11β-HSD.

The term "antagonist" generally means a compound that binds to an enzyme and inhibits the activity of that enzyme. As used here, however, the term is intended to refer broadly to any agent that inhibits the activity of a molecule, by any mechanism. Accordingly, it includes agents that affect the expression of a protein such as 11β-HSD, or the biosynthesis of a molecule such as 11β-HSD, or the expression of modulators of the activity of 11β-HSD. The specific activity inhibited can be any activity that is characteristic of the enzyme or molecule, for example, a dehydrogenase activity of 11β-HSD1. Activity assays for these are known to those skilled in the art. As used herein, in general, the term "antagonist" includes but is not limited to agents such as an atom or molecule, wherein a molecule may be inorganic or organic, a biological effector molecule and/or a nucleic acid encoding an agent such as a biological effector molecule, a protein, including, but not limited to, a structural protein, an enzyme, a cytokine (such as an interferon and/or an interleukin), a polypeptide, a peptide, a nucleic acid, a peptide nucleic acid (PNA), a virus, a virus-like particle, a nucleotide, a ribonucleotide, a synthetic analogue of a nucleotide, a synthetic analogue of a ribonucleotide, a modified nucleotide, a modified ribonucleotide, an amino acid, an amino acid analogue, a modified amino acid, a modified amino acid analogue, a steroid, a proteoglycan, a lipid, a fatty acid, or a carbohydrate or any small molecule capable of modifying the biosynthesis, degradation or activity of 11β-HSD, including 11β-HSD1, 11β-HSD2 and 11β-HSD3. An agent may be in solution or in suspension (e.g., in crystalline, colloidal or other particulate form). The agent may be in the form of a monomer, dimer, oligomer, etc, or otherwise in a complex.

The antagonist may bind to and compete for one or more sites on the relevant molecule, for example, a 11β-HSD molecule, to reduce one or more of its activities (including dehydrogenase activity). The antagonist need not specifically bind directly to a catalytic site, and may bind for example to an adjacent site, another protein (for example, a protein which is complexed with the enzyme) or other entity on or in the cell, so long as its binding reduces the activity of the enzyme or molecule.

The term "antagonist" is also intended to include, an antibiotic, a polyclonal or monoclonal antibody, or an effective part thereof, such as an Fv fragment, which antibody or part thereof may be natural, synthetic or humanized, a peptide hormone, a receptor, a signaling molecule or other protein; a nucleic acid, as defined below, including, but not limited to, an oligonucleotide or modified oligonucleotide, an antisense oligonucleotide or modified antisense oligonucleotide, cDNA, genomic DNA, an artificial or natural chromosome (e.g., a yeast artificial chromosome) or a part thereof, RNA, including mRNA, tRNA, rRNA or a ribozyme, or a peptide nucleic acid (PNA); a virus or virus-like particles; a nucleotide or ribonucleotide or synthetic analogue thereof, which may be modified or unmodified; an amino acid or analogue thereof, which may be modified or unmodified; a non-peptide (e.g., steroid) hormone; a proteoglycan; a lipid; or a carbohydrate. Small molecules, including inorganic and organic chemicals, which bind to and occupy the active site of the polypeptide thereby making the catalytic site inaccessible to substrates such that normal biological activity is prevented, are also included. Examples of small molecules include but are not limited to small peptides or peptide-like molecules.

In a second embodiment, a mammal can be treated for alcohol use disorder, abuse, and/or dependence by administration of a composition comprising carbenoxolone. Examples of formulations and dosages for systemic delivery to a patient to reduce craving for alcohol include such as, preferably administration at a rate of at or about 100 mg every 8 to 24 hours, preferably over a course of 4 weeks or more or it can also be administered on an as-needed basis. The formulations can alternatively be administered to an individual at or about 1, 1.5, 2, 2.5, 3, 3.5, 4, 4.5, 5, 5.5, 6, 6.5, 7, 7.5, 8, 8.5, 9, 9.5 or 10 mg/kg/day. Dosages may even be between 20, 40 and 60 mg/kg/day. In one preferred embodiment, carbenoxolone is administered to an individual at a rate of about 4.5 mg/kg/day.

A pharmaceutically or therapeutically effective amount is an amount of a composition which achieves the desired effect in an animal or human. As is well known to those of skill in the art, the specific amount to achieve efficacy will vary depending upon a number of factors. Using the guidance provided herein and knowledge of the art, determining of a pharmaceutically effective amount of carbenoxolone is within the ordinary skill of a physician. Pharmaceutically effective amounts designed for particular applications may be packaged as unit doses to facilitate administration.

Inhibition of 11β-HSD2 by carbenoxolone in some individuals—approximately 20% of subjects (39)—has been associated with various physiological conditions including increased blood pressure due to increased aldosterone activity (11). Thus, to assist efficacy of carbenoxolone in treating alcohol abuse, it may be administered in a formulation with other active agents such as an anti-kaliuretic-diuretic agent. Preferably, the diuretic is such that it selectively enhances the excretion of sodium ions without causing an increase in excretion of potassium ions. Anti-kaliuretic-diuretics, also known as "potassium-sparing diuretics", comprise a class of drugs capable of blocking the exchange of sodium for potassium and hydrogen ions in the distal tubule, causing an increase in the excretion of sodium and chloride with a negligible increase in potassium excretion.

In preferred embodiments, agents used with carbenoxolone administration are capable of modulating the inhibition of carbenoxolone on 11β-HSD2, preferably down-regulating, most preferably reversing such inhibition. Preferably, this secondary agent is not capable of binding to mineralocorticoid receptors; more preferably the second agent is not capable of blocking mineralocorticoid receptors.

A composition comprising carbenoxolone, can be delivered by conventional medicinal approaches, preferably in the form of a pharmaceutical composition. A pharmaceutical composition in the context of the present invention is a composition of matter comprising at least an inhibitor or antagonist of 11β-HSD alone or together with a second agent which comprises a diuretic, preferably an anti-kaliuretic-diuretic, as an active ingredient, as well as a carrier, excipient, and/or diluent.

Administration can be in any convenient manner such as by the oral, intravenous (where water soluble), intramuscular, subcutaneous, intranasal, intradermal, or suppository routes or implanting. In some embodiments, the tablets are coated or scored and are formulated so as to provide slow or controlled release of the active ingredient therein. Depending on the route of administration, the active ingredients can be required to be coated in a material to protect said ingredients from the action of enzymes, acids and other natural conditions which can inactivate said ingredient. In a preferred embodiment, carbenoxolone is administered orally.

The prevention of the action of microorganisms can be brought about by various antibacterial and antifungal agents, for example, parabens, chlorobutanol, phenyl, sorbic acid, thimerosal, and the like. In preferred embodiments, isotonic agents, for example, sugars or sodium chloride, can be included. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from previously sterile-filtered solution thereof.

When the combination of polypeptides is suitably protected as described above, it can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound can be incorporated with excipients and used in the form of ingestible tablets, buccal tablets, troches, capsules, elixirs, suspensions, syrups, wafers, and the like. The amount of active compound in such therapeutically useful compositions is such that a suitable dosage will be obtained.

The tablets, troches, pills, capsules and the like can also contain the following: a binder such as gum tragacanth, acacia, corn starch or gelatin; excipients such as dicalcium phosphate, a disintegrating agent such as corn starch, potato starch, alginic acid and the like, a lubricant such as magnesium stearate; and a sweetening agent such as sucrose, lactose or saccharin may be added or a flavoring agent such as peppermint, oil of wintergreen, and other flavorings. When the dosage unit form is a capsule, it can contain, in addition to materials of the above type, a liquid carrier.

Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulations.

As used herein "pharmaceutically acceptable carrier and/or diluent" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms are dictated by and directly dependent on (a) the unique characteristics of the active material and the particular therapeutic effect to be achieved, and (b) the limitations inherent in the art of compounding such as active material for the treatment of disease in living subjects having a diseased condition in which bodily health is impaired.

The principal active ingredients are compounded for convenient and effective administration in effective amounts with a suitable pharmaceutically acceptable carrier in dosage unit form. In the case of compositions containing supplementary active ingredients, the dosages are determined by reference to the usual dose and manner of administration of the said ingredients.

In some embodiments, the first agent which is an antagonist of 11β-HSD, namely carbenoxolone or derivative thereof and a possible second agent, if any, which comprises a diuretic such as, but not limited to, an anti-kaliuretic-diuretic can be provided in the form of a pharmaceutical composition.

Such first and second agents can be administered separately or as a single pharmaceutical formulation. Thus, the invention includes pharmaceutical compositions comprising a first agent that is an antagonist of 11β-HSD, together with a second agent that comprises, for example, a diuretic, preferably an anti-kaliuretic-diuretic. Alternatively, a treatment regimen involving first and second agents can involve administration of each agent in its own composition, which may be administered before, concurrently, or after the other agent(s).

Such pharmaceutical compositions are useful for delivery of the first or second agents, or both, preferably in the form of a composition as described, to an individual for the treatment or alleviation of symptoms as described.

Carbenoxolone and modes of administration thereof are described in previous studies that aimed at inhibiting 11β-HSD1 systemically for therapeutic purposes in humans, including in Walker et al., "Carbenoxolone Increases Hepatic Insulin Sensitivity in Man: A Novel Role for 11-oxosteroid Reductase in Enhancing Glucocorticoid Receptor Activation," (18) and "11β-hydroxysteroid dehydrogenase inhibition improves cognitive function in healthy elderly men and type 2 diabetics" (20). Both these studies used an oral dose of 100 mg three times per day (18, 20), which is a conventional dose of carbenoxolone for peptic ulcer (39). This dose of carbenoxolone in one study was combined with amiloride (10 mg/day) to prevent the occurrence of renal mineralocorticoid excess (20), which is seen in approximately 20% of subjects chronically treated with carbenoxolone at the dose of 100 mg three times per day (39).

The effective amount of agent depends on the age, weight and condition of a patient. In general, the daily oral dose of agent is less than 1200 mg, and more than 50 mg. The preferred daily oral dose is about 100-600 mg. Oral formulations are conveniently presented in a unit dosage form and can be prepared by any method known in the art of pharmacy. The composition can be formulated together with a suitable pharmaceutically acceptable carrier into any desired dosage form. Typical unit dosage forms include tablets, pills, powders, solutions, suspensions, emulsions, granules, capsules, suppositories. In general, the formulations are prepared by uniformly and intimately bringing into association the agent composition with liquid carriers or finely divided solid carriers or both, and as necessary, shaping the product. The active ingredient can be incorporated into a variety of basic materials in the form of a liquid, powder, tablets or capsules to give an effective amount of active ingredient to treat the disease. In a highly preferred embodiment, carbenoxolone is administered to an individual at a rate of about 100 mg 1-3 times a day, preferably 3 times a day every 8 hours, or at a rate of about 4.5 mg/kg/day. Carbenoxolone can also be administered on an as-needed basis to reduce craving for alcohol in an individual.

A second agent capable of modulating the inhibition of 11β-HSD2 by carbenoxolone or another non-selective 11β-HSD inhibitor may also be administered with carbenoxolone or another non-selective 11β-HSD inhibitor to prevent—preferably down-regulating, most preferably reversing—such inhibition of 11β-HSD2. Preferably, the second agent is not capable of binding to mineralocorticoid receptors; more preferably the second agent is not capable of blocking mineralocorticoid receptors. Such agents may include an anti-kaliuretic-diuretic that enhances the excretion of sodium ions without causing an increase in excretion of potassium ions such as a pyrazine-carbonyl-guanidine like amiloride (3,5-diamino-6-chloro-N-(diami-nomethylene) pyrazinecarboxamide), or a salt or ester thereof, preferably amiloride-HCl, more preferably amiloride-monohydrochloride, dihydrate. Alternatively, such agent may include an aldosterone antagonist, such as an androstadiene-spiro-furan like spironolactone (17-hydroxy-7alpha-mercapto-3-oxo-17alpha-pregn-4-ene-21-carboxylic acid gamma-lactone) or a salt or ester thereof, preferably spironolactone-acetate, or Eplerenone.

Other inhibitors of 11β-hydroxysteroid dehydrogenase have been described and they include the compounds in Table I, including 18α- and 18β-glycyrrhetinic acid (40) and various of their derivatives, e.g., (41-44); furosemide, naringenin, found in grapefruit juice, ethacrynic acid, and chenodeoxycholic acid (45); 11β-aminoprogesterone derivatives (46); benzazol-2-yl piperazine sulfonamides (47); arylsulphonamidothiazoles (48); 3,3-disubstituted-(8-aza-bicyclo[3.2.1]oct-8-yl)-[5-(1H-pyrazol-4-yl)-thi-ophen-3-yl]-methanone, 3,3-disubstituted-(6-aza-bicyclo[3.1.1]hept-6-yl)-[5-(1H-pyrazol-4-yl)-th-iophen-3-yl]-methanone, and 4,4-disubstituted piperidin-1-yl)-[5-(1H-pyrazol-4-yl)-thiophen-3-yl]-methanone compounds that selectively inhibit 11β-HSD1 (Patent application number: 20130123268); Amido-Thiophene Compounds that selectively inhibit 11β-HSD1 (Patent application numbers: 20130012545; 20110015178; 20100267696); (4-phenyl-piperidin-1-yl)-[5-(1H-pyrazol-4-yl)-thiophen-3-yl]-methanone compounds that selectively inhibit 11β-HSD1 (Patent application number: 20120172393); compounds that selectively inhibit 11β-HSD1 (Patent application number: 20120095046); as well as other structures including adamantyl triazoles, octyltriazoles, phenyl triazoles, among others (17, 49-54). Any one of these 11β-HSD inhibitors can be used to treat alcohol use disorders. All of these cited publications are hereby incorporated by reference in their entirety.

Table I, below, provides a list of 11β-HSD inhibitors that, because of their inhibition activity, use of any of them is contemplated in the context of the invention for treating a patient who is in need of decreasing intake of alcohol due to an alcohol abuse disease or disorder.

TABLE 1

Chemical structure of 11β-HSD inhibitor families.

| Number | Molecular structure | Name | Specificity | References |
|---|---|---|---|---|
| 1 | 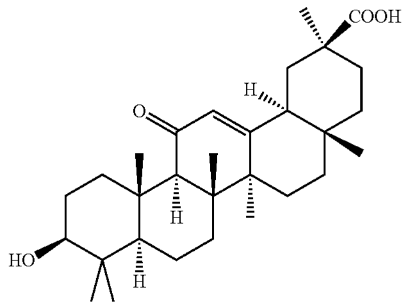 | 18α-glycyrrhetinic acid | 11β-HSD1 > 2 | (40) |
| 2 | 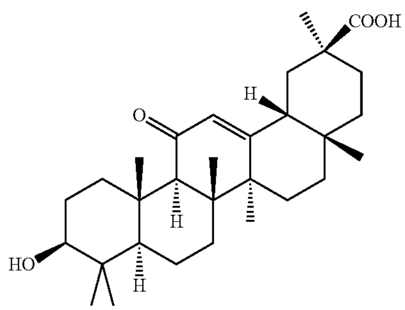 | 18β-glycyrrhetinic acid | 11β-HSD1, 2 | (40) |
| 3 | (show as disodium salt) | 18β-glycyrrhetinic acid. 3β-O-hemisuccunate (carbenoxolone) | 11β-HSD1, 2 | |
| 4 | (show as disodium salt) | 18α-glycyrrhetinic acid. 3β-O-hemisuccunate | 11β-HSD1 > 2 | |
| 5 | 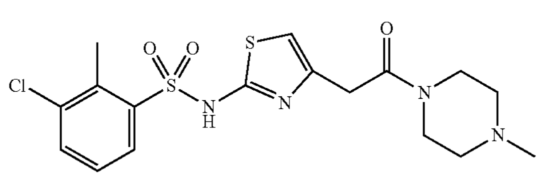 [SMILES: Cc1c(Cl)cccc1S(=O)(=O)Nc1nc(CC(=O)N2CCN(C)CC2)cs1] | BVT-2733 | 11β-HSD1 > 2 | (55) |

TABLE 1-continued

Chemical structure of 11β-HSD inhibitor families.

| Number | Molecular structure | Name | Specificity | References |
|---|---|---|---|---|
| 6 | 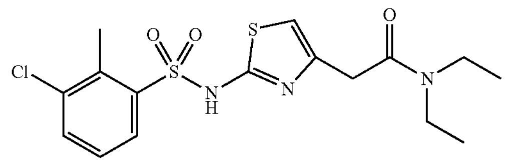 [SMILES: CCN(CC)C(=O)Cc1csc(NS(=O)(=O)c2cccc(Cl)c2C)n1] | BVT-14225 | 11β-HSD1 > 2 | (55) |
| 7 | 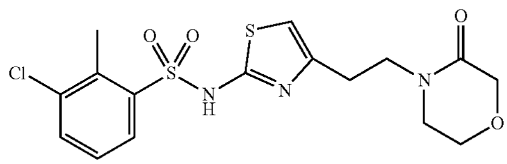 [SMILES: Cc1c(Cl)cccc1S(=O)(=O)Nc1nc(CCN2CCOCC2=O)cs1] | BVT-3498/AMG-331 (3-chloro-2-methyl-N-{4-[2-(3-oxo-4-morpholinyl)ethyl]-1,3-thiazol-2-yl}benzenesulfonamide). | 11β-HSD1 > 2 | Structure disclosed on page 9 of Abrahmsen, L.; Nilsson, J.; Opperman, U.; Svensson, S. Wo2005068646A1, 2005 |
| 8 | 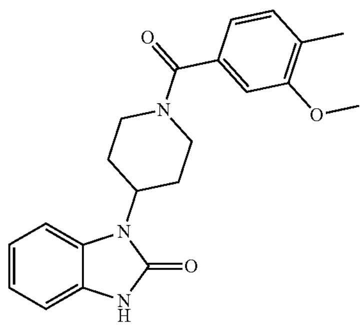 [SMILES: COc1cc(C(=O)N2CCC(n3c(=O)[nH]c4ccccc43)CC2)ccc1C] | Biovitrum ##Need to add other compounds in series | 11β-HSD1 > 2 | (56) |
| 9 | 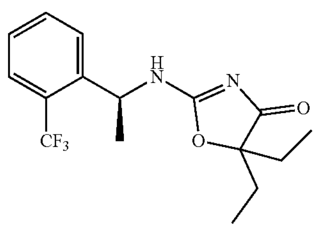 [SMILES: CCC1(CC)OC(N[C@@H](C)c2ccccc2C(F)(F)F)=NC1=O] | Biovitrum ##Need to add other compounds in series | 11β-HSD1 > 2 | (57) |
| 10 | 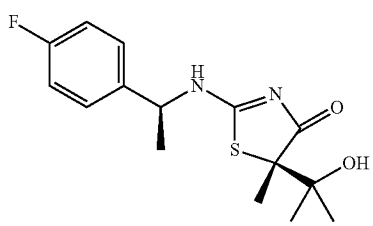 [SMILES: C[C@H](NC1=NC(=O)[C@@](C)(C(C)(C)O)S1)c1ccc(F)cc1] | Amgen | 11β-HSD1 > 2 | (58) |
| 11 | 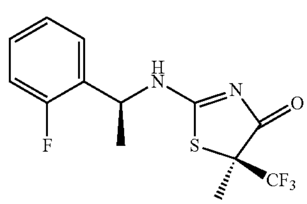 [SMILES: C[C@H](NC1=NC(=O)[C@@](C)(C(F)(F)F)S1)c1ccccc1F] | Amgen Cpd 2922 BVT-116429 | 11β-HSD1 > 2 | (59) |
| 12 | 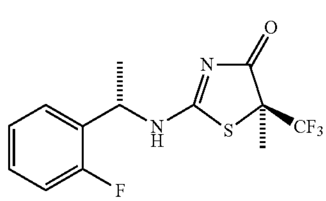 [SMILES: C[C@H](NC1=NC(=O)[C@@](C)(C(F)(F)F)S1)c1ccccc1F] | AMGEN 2922 | 11β-HSD1 > 2 | (60) |

TABLE 1-continued

Chemical structure of 11β-HSD inhibitor families.

| Number | Molecular structure | Name | Specificity | References |
|---|---|---|---|---|
| 13 | 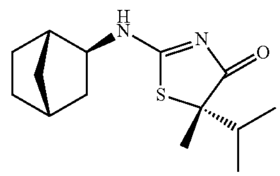 [SMILES: CC(C)[C@]1(C)SC(N[C@H]2C[C@@H]3CC[C@H]2C3)=NC1=O] | AMGEN 221 BVT-83370 | 11β-HSD1 > 2 | (61) |
| 14 | 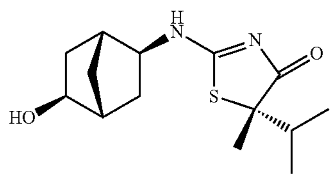 [SMILES: CC(C)[C@]1(C)SC(N[C@H]2C[C@H]3C[C@@H]2C[C@@H]3O)=NC1=O] | AMGEN | 11β-HSD1 > 2 | (62) |
| 15 | 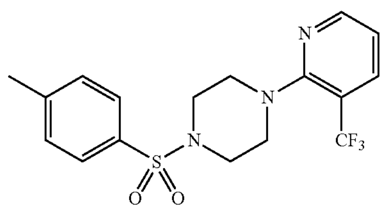 | AMGEN | 11β-HSD1 > 2 | (63) |
| 16 | 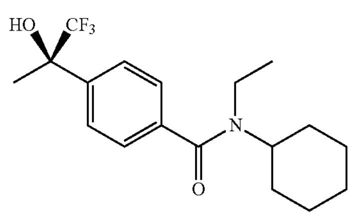 [SMILES: CCN(C(=O)c1ccc([C@@](C)(O)C(F)(F)F)cc1)C1CCCCC1] | AMGEN | 11β-HSD1 > 2 | (64) |
| 17 | 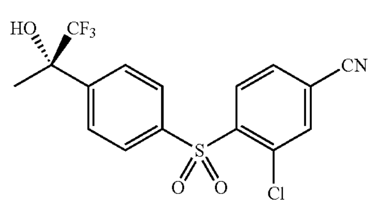 [SMILES: C[C@](O)(c1ccc(S(=O)(=O)c2ccc(C#N)cc2Cl)cc1)C(F)(F)F] | AMGEN | 11β-HSD1 > 2 | (65) |
| 18 | 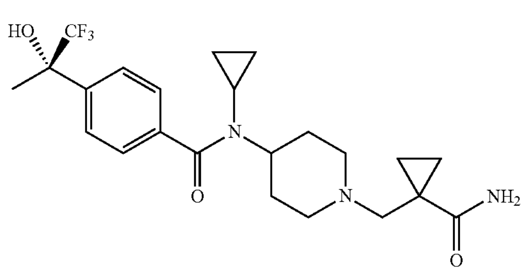 [SMILES: C[C@](O)(c1ccc(C(=O)N(C2CC2)C2CCN(CC3(C(N)=O)CC3)CC2)cc1)C(F)(F)F] | AMGEN | 11β-HSD1 > 2 | (66) |

TABLE 1-continued
Chemical structure of 11β-HSD inhibitor families.
| Number | Molecular structure | Name | Specificity | References |
|---|---|---|---|---|
| 19 | 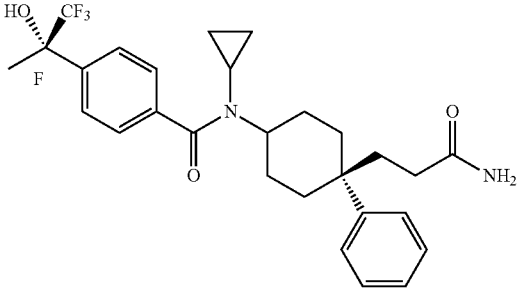 | AMGEN | 11β-HSD1 > 2 | (67) |
| 20 | 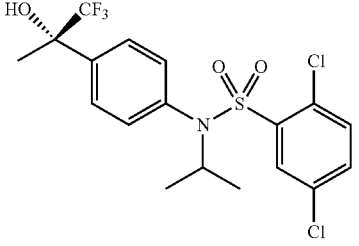 [SMILES: CC(C)N(c1ccc([C@](C)(O)C(F)(F)F)cc1)S(=O)(=O)c1cc(Cl)ccc1Cl] | AMGEN | 11β-HSD1 > 2 | (68) |
| 21 | 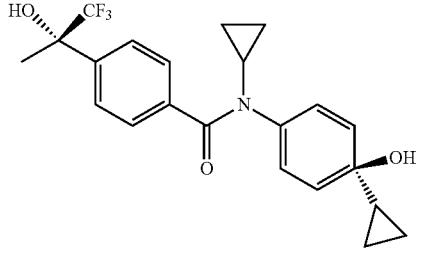 | AMGEN | 11β-HSD1 > 2 | (69) |
| 21 | 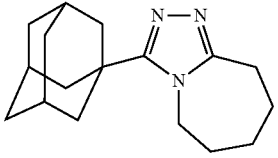 [SMILES: C1CCc2nnc(C34CC5CC(CC(C5)C3)C4)n2CC1] | MERK-544 | 11β-HSD1 > 2 | (70) |
| 23 | 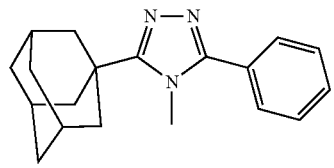 [SMILES: Cn1c(-c2ccccc2)nnc1C12CC3CC(CC(C3)C1)C2] | MERK | 11β-HSD1 > 2 | (71) |
| 24 | 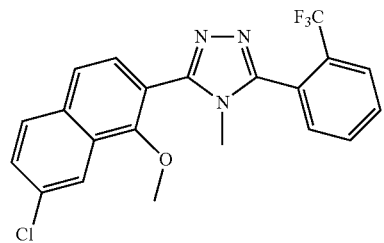 [SMILES: COc1c(-c2nnc(-c3ccccc3C(F)(F)F)n2C)ccc2ccc(Cl)cc12] | MERK | 11β-HSD1 > 2 | (72) |

TABLE 1-continued

Chemical structure of 11β-HSD inhibitor families.

| Number | Molecular structure | Name | Specificity | References |
|---|---|---|---|---|
| 25 | 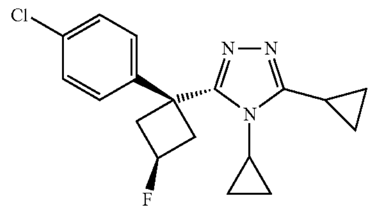 | MERK MK-0916 | 11β-HSD1 > 2 | (73) |
| 26 | 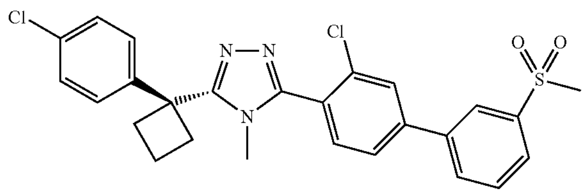 | MERK | 11β-HSD1 > 2 | (74) |
| 27 | 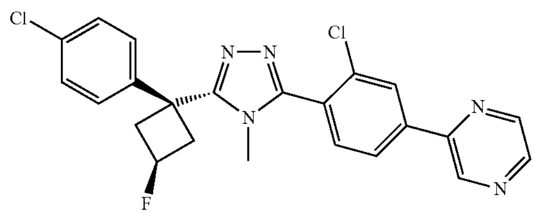 | MERK | 11β-HSD1 > 2 | (75) |
| 28 | 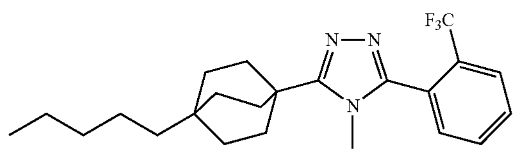 [SMILES: CCCCCC12CCC(c3nnc(-c4ccccc4C(F)(F)F)n3C)(CC1)CC2] | MERK | 11β-HSD1 > 2 | (76,77) |
| 29 | 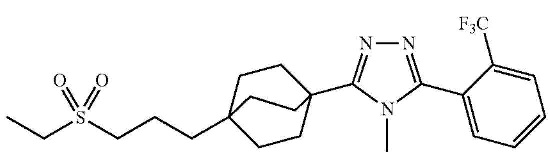 [SMILES: CCS(=O)(=O)CCCC12CCC(c3nnc(-c4ccccc4C(F)(F)F)n3C)(CC1)CC2] | MERK MK-0736 | 11β-HSD1 > 2 | (77) |
| 30 | 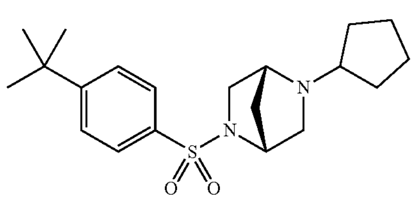 [SMILES: CC(C)(C)c1ccc(S(=O)(=O)N2C[C@H]3C[C@@H]2CN3C2CCCC2)cc1] | MERK | 11β-HSD1 > 2 | (78) |
| 31 | 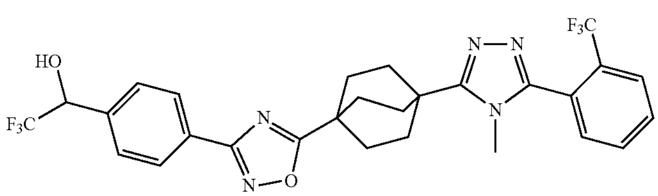 [SMILES: Cn1c(-c2ccccc2C(F)(F)F)nnc1C12CCC(c3nc(-c4ccc(C(O)C(F)(F)F)cc4)no3)(CC1)CC2] | MERK | 11β-HSD1 > 2 | (76) |
| 32 | 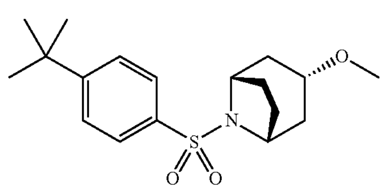 | MERK | 11β-HSD1 > 2 | (78) |

TABLE 1-continued

Chemical structure of 11β-HSD inhibitor families.

| Number | Molecular structure | Name | Specificity | References |
|---|---|---|---|---|
| 33 | 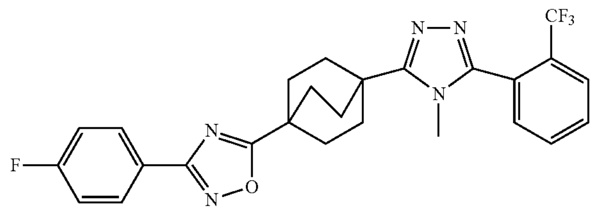 [SMILES: Cn1c(-c2ccccc2C(F)(F)F)nnc1C12CCC(c3nc(-c4ccc(F)cc4)no3)(CC1)CC2] | MERK | 11β-HSD1 > 2 | (76) |
| 34 | 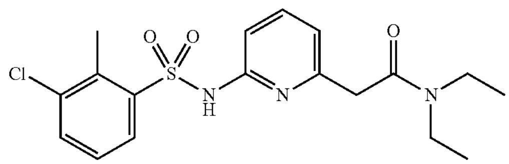 [SMILES: CCN(CC)C(=O)Cc1cccc(NS(=O)(=O)c2cccc(Cl)c2C)n1] | MERK | 11β-HSD1 > 2 | (79) |
| 35 | 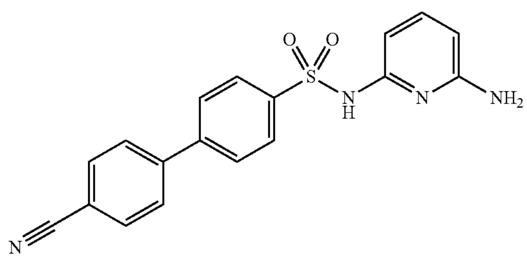 [SMILES: N#Cc1ccc(-c2ccc(S(=O)(=O)Nc3cccc(N)n3)cc2)cc1] | Pfizer PF-915275 | 11β-HSD1 > 2 | (79-81) |
| 36 | 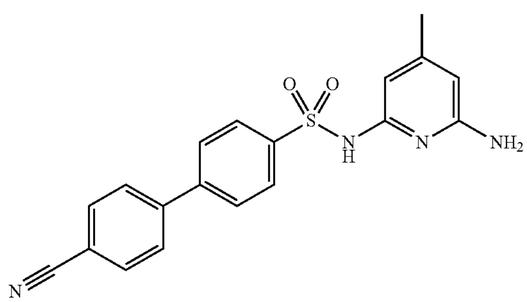 [SMILES: Cc1cc(N)nc(NS(=O)(=O)c2ccc(-c3ccc(C#N)cc3)cc2)c1] | Pfizer | 11β-HSD1 > 2 | (82) |
| 37 | 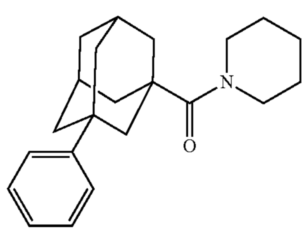 [SMILES: O=C(N1CCCCC1)C12CC3CC(C1)CC(c1ccccc1)(C3)C2] | Pfizer | 11β-HSD1 > 2 | (83) |
| 38 | 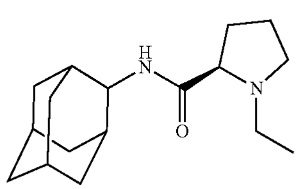 [SMILES: CCN1CCC[C@@H]1C(=O)NC1C2CC3CC(C2)CC1C3] | Pfizer PF-877423 | 11β-HSD1 > 2 | (70, 83) |

TABLE 1-continued
Chemical structure of 11β-HSD inhibitor families.
| Number | Molecular structure | Name | Specificity | References |
|--------|---------------------|------|-------------|------------|
| 39 | 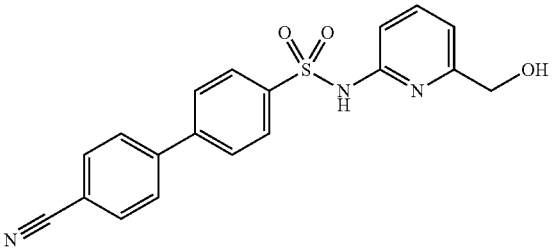 [SMILES: N#Cc1ccc(-c2ccc(S(=O)(=O)Nc3cccc(CO)n3)cc2)cc1] | Pfizer | 11β-HSD1 > 2 | (82) |
| 40 | 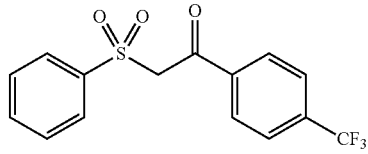 [SMILES: O=C(CS(=O)(=O)c1ccccc1)c1ccc(C(F)(F)F)cc1] | Wyeth | 11β-HSD1 > 2 | (84) |
| 41 | 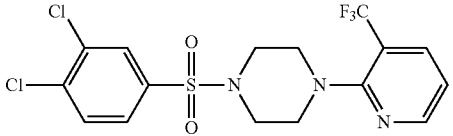 | Wyeth | 11β-HSD1 > 2 | (85) |
| 42 | 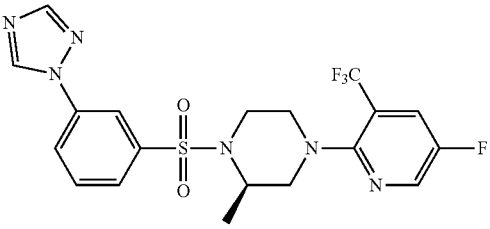 [SMILES: C[C@@H]1CN(c2ncc(F)cc2C(F)(F)F)CCN1S(=O)(=O)c1cccc(-n2cncn2)c1] | Wyeth | 11β-HSD1 > 2 | (85) |
| 43 | 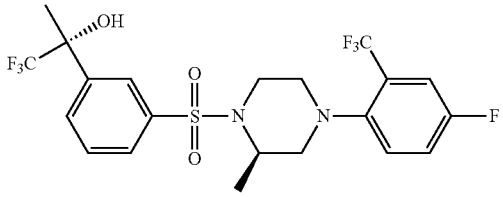 [SMILES: C[C@@H]1CN(c2ccc(F)cc2C(F)(F)F)CCN1S(=O)(=O)c1cccc([C@@](C)(O)C(F)(F)F)c1] | Wyeth HSD-016 | 11β-HSD1 > 2 | (86) |
| 44 | 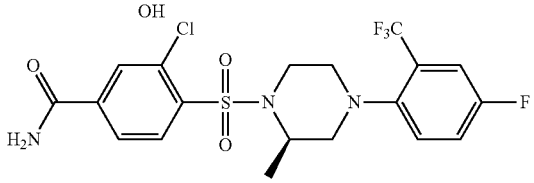 | Wyeth | 11β-HSD1 > 2 | (87) |
| 45 | 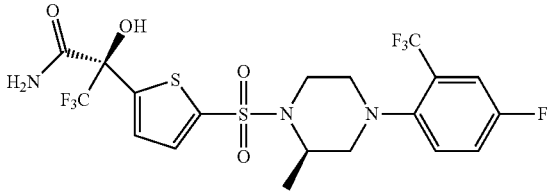 [SMILES: C[C@@H]1CN(c2ccc(F)cc2C(F)(F)F)CCN1S(=O)(=O)c1ccc([C@@](O)(C(N)=O)C(F)(F)F)s1] | Wyeth HSD-621 | 11β-HSD1 > 2 | (88) |

TABLE 1-continued

Chemical structure of 11β-HSD inhibitor families.

| Number | Molecular structure | Name | Specificity | References |
|---|---|---|---|---|
| 46 | 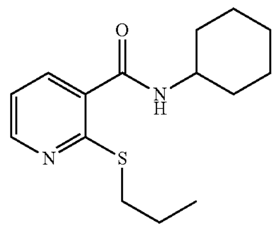 [SMILES: CCCSc1ncccc1C(=O)NC1CCCCC1] | AstraZeneca | 11β-HSD1 > 2 | (89) |
| 47 | 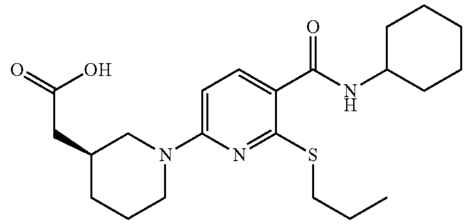 [SMILES: CCCSc1nc(N2CCC[C@@H](CC(=O)O)C2)ccc1C(=O)NC1CCCCC1] | AstraZeneca AZD4017 | 11β-HSD1 > 2 | (89) |
| 48 | 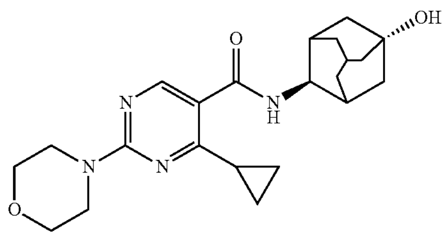 [SMILES: O=C(N[C@H]1C2CC3CC1C[C@@](O)(C3)C2)c1cnc(N2CCOCC2)nc1C1CC1] | AstraZeneca | 11β-HSD1 > 2 | (90) |
| 49 | 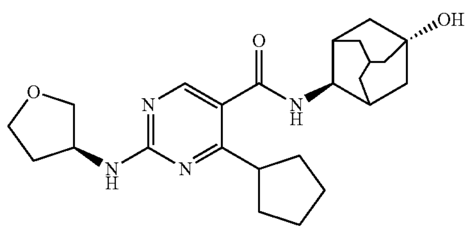 [SMILES: O=C(N[C@H]1C2CC3CC1C[C@@](O)(C3)C2)c1cnc(N[C@H]2CCOC2)nc1C1CCCC1] | AstraZeneca | 11β-HSD1 > 2 | (91) |
| 50 | 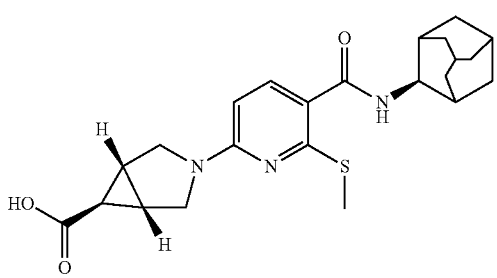 | AstraZeneca AZD6925 | 11β-HSD1 > 2 | (92) |
| 51 | 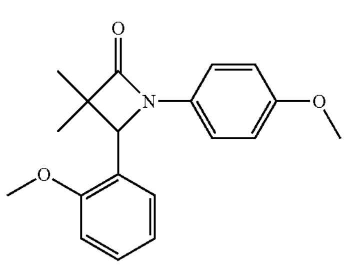 | AstraZeneca | 11β-HSD1 > 2 | (93) |

TABLE 1-continued

Chemical structure of 11β-HSD inhibitor families.

| Number | Molecular structure | Name | Specificity | References |
|---|---|---|---|---|
| 52 | 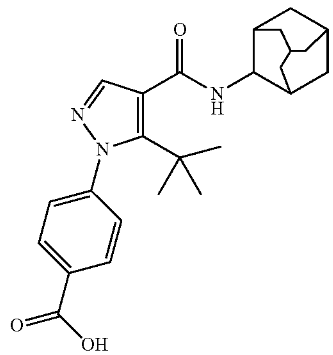 [SMILES: CC(C)(C)c1c(C(=O)NC2C3CC4CC(C3)CC2C4)cnn1-c1ccc(C(=O)O)cc1] | AstraZeneca AZD8329 | 11β-HSD1 > 2 | (94) |
| 53 | 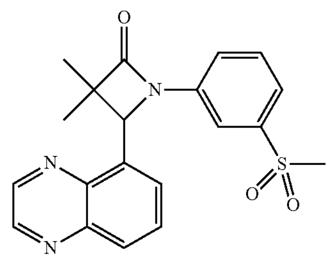 [SMILES: CC1(C)C(=O)N(c2cccc(S(C)(=O)=O)c2)C1c1cccc2nccnc12] | AstraZeneca | 11β-HSD1 > 2 | (93) |
| 54 | 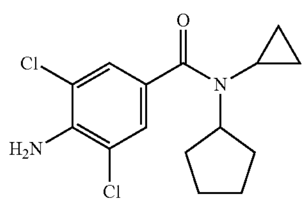 [SMILES: Nc1c(Cl)cc(C(=O)N(C2CCCC2)C2CC2)cc1Cl] | Abbott | 11β-HSD1 > 2 | (6) |
| 55 | 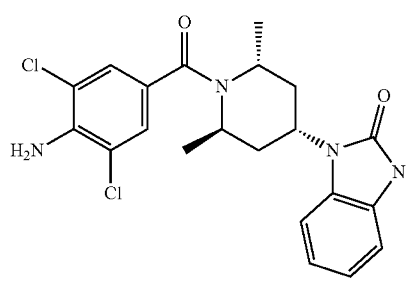 | Abbott | 11β-HSD1 > 2 | (6) |
| 56 | 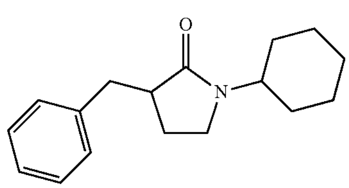 [SMILES: O=C1C(Cc2ccccc2)CCN1C1CCCCC1] | Abbott | 11β-HSD1 > 2 | (6) |
| 57 | 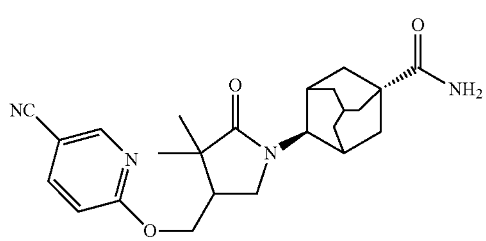 [SMILES: CC1(C)C(=O)N([C@H]2C3CC4CC2C[C@@](C(N)=O)(C4)C3)CC1COc1ccc(C#N)cn1] | Abbott | 11β-HSD1 > 2 | (6) |

TABLE 1-continued
Chemical structure of 11β-HSD inhibitor families.
| Number | Molecular structure | Name | Specificity | References |
|---|---|---|---|---|
| 58 | 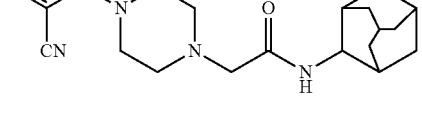 | Abbott | 11β-HSD1 > 2 | (6) |
| 59 | 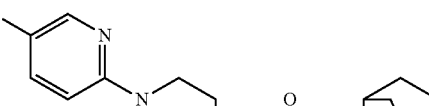 | Abbott | 11β-HSD1 > 2 | (6) |
| 60 | 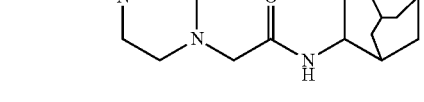 | Abbott ABT-384 | 11β-HSD1 > 2 | (6) |
| 61 | 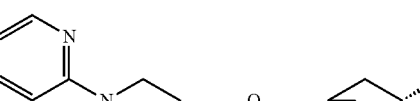 | Abbott | 11β-HSD1 > 2 | (6) |
| 62 | 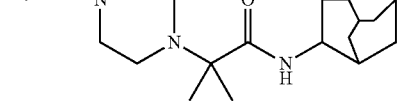 | Abbott | 11β-HSD1 > 2 | (6) |
| 63 | 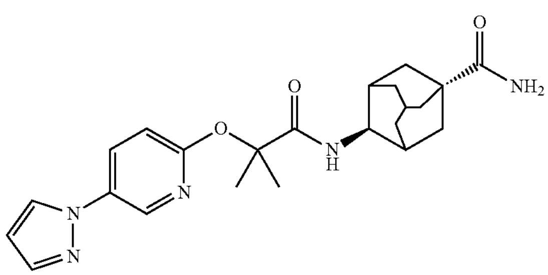 [SMILES: CC(C)(Oc1ccc(-n2cccn2)cn1)C(=O)N[C@H]1C2CC3CC1C[C@@](C(N)=O)(C3)C2] | Abbott | 11β-HSD1 > 2 | (6) |
| 64 | 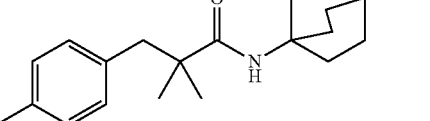 | Abbott | 11β-HSD1 > 2 | (6) |

TABLE 1-continued
Chemical structure of 11β-HSD inhibitor families.
| Number | Molecular structure | Name | Specificity | References |
|---|---|---|---|---|
| 65 | 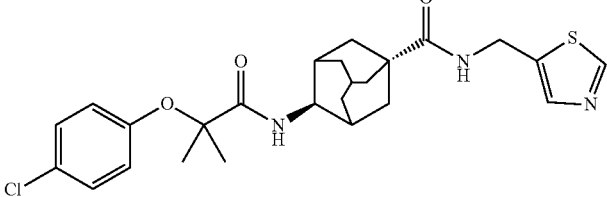 | Abbott | 11β-HSD1 > 2 | (6) |
| 66 | 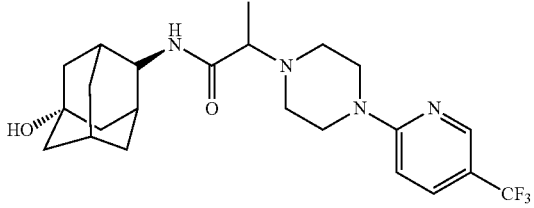 | Abbott | 11β-HSD1 > 2 | (60, 81) |
| 67 | 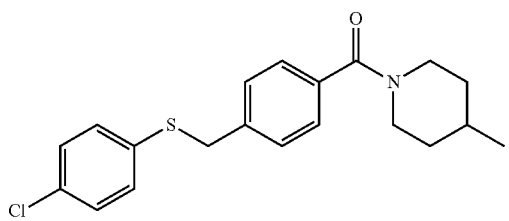 [SMILES: CC1CCN(C(=O)c2ccc(CSc3ccc(Cl)cc3)cc2)CC1] | Bristol-Myers Squibb | 11β-HSD1 > 2 | (6) |
| 68 | 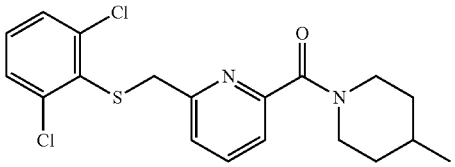 [SMILES: CC1CCN(C(=O)c2cccc(CSc3c(Cl)cccc3Cl)n2)CC1] | Bristol-Myers Squibb | 11β-HSD1 > 2 | (6) |
| 69 | 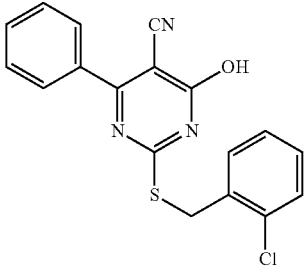 [SMILES: N#Cc1c(O)nc(SCc2ccccc2Cl)nc1-c1ccccc1] | Bristol-Myers Squibb | 11β-HSD1 > 2 | (6) |
| 70 | 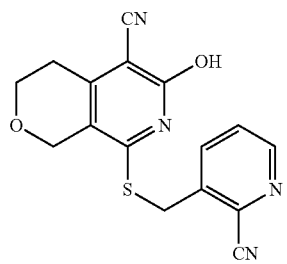 [SMILES: N#Cc1ncccc1CSc1nc(O)c(C#N)c2c1COCC2] | Bristol-Myers Squibb | 11β-HSD1 > 2 | (6) |
| 71 | 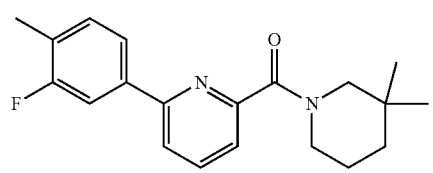 [SMILES: Cc1ccc(-c2cccc(C(=O)N3CCCC(C)(C)C3)n2)cc1F] | Bristol-Myers Squibb | 11β-HSD1 > 2 | (6) |

TABLE 1-continued

Chemical structure of 11β-HSD inhibitor families.

| Number | Molecular structure | Name | Specificity | References |
|---|---|---|---|---|
| 72 | 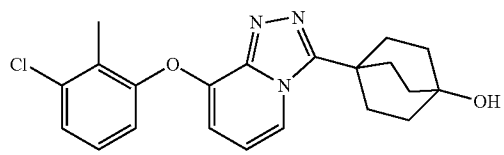 [SMILES: Cc1c(Cl)cccc1Oc1cccn2c(C34CCC(O)(CC3)CC4)nnc12] | Bristol-Myers Squibb | 11β-HSD1 > 2 | (6) |
| 73 | 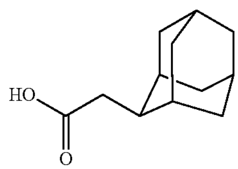 [SMILES: O=C(O)CC1C2CC3CC(C2)CC1C3] | Bristol-Myers Squibb | 11β-HSD1 > 2 | (6) |
| 74 | 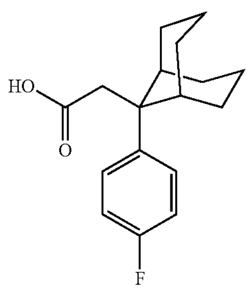 [SMILES: O=C(O)CC1(c2ccc(F)cc2)C2CCCC1CCC2] | Bristol-Myers Squibb | 11β-HSD1 > 2 | (6) |
| 75 | 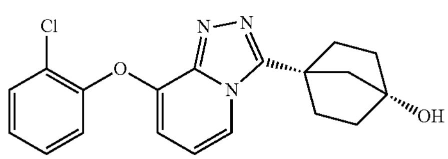 [SMILES: O[C@]12CC[C@](c3nnc4c(Oc5ccccc5Cl)cccn43)(CC1)C2] | Bristol-Myers Squibb BMS-770767 | 11β-HSD1 > 2 | (6) |
| 76 | 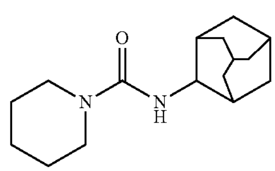 [SMILES: O=C(NC1C2CC3CC(C2)CC1C3)N1CCCCC1] | Vitae Pharmaceuticals | 11β-HSD1 > 2 | (6) |
| 77 | 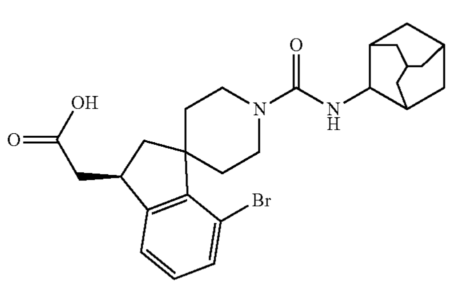 [SMILES: O=C(O)C[C@H]1CC2(CCN(C(=O)NC3C4CC5CC(C4)CC3C5)CC2)c2c(Br)cccc21] | Vitae Pharmaceuticals | 11β-HSD1 > 2 | (6) |
| 78 | 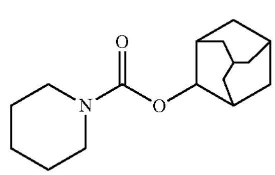 [SMILES: O=C(OC1C2CC3CC(C2)CC1C3)N1CCCCC1] | Vitae Pharmaceuticals | 11β-HSD1 > 2 | (6) |

TABLE 1-continued

Chemical structure of 11β-HSD inhibitor families.

| Number | Molecular structure | Name | Specificity | References |
|---|---|---|---|---|
| 79 | 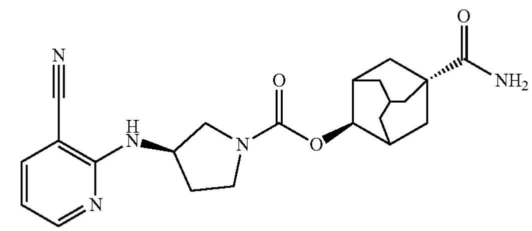 [SMILES: N#Cc1cccnc1N[C@@H]1CCN(C(=O)O[C@H]2C3CC4CC2C[C@@](C(N)=O)(C4)C3)C1] | Vitae Pharmaceuticals | 11β-HSD1 > 2 | (6) |
| 80 | 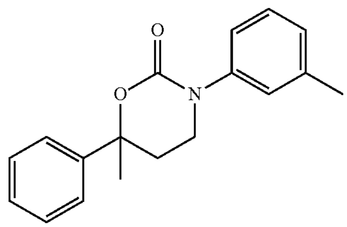 [SMILES: Cc1cccc(N2CCC(C)(c3ccccc3)OC2=O)c1] | Vitae Pharmaceuticals | 11β-HSD1 > 2 | (6) |
| 81 | 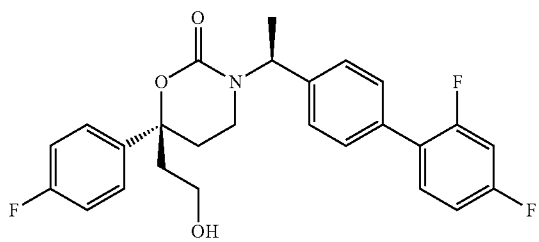 [SMILES: C[C@@H](c1ccc(-c2ccc(F)cc2F)cc1)N1CC[C@](CCO)(c2ccc(F)cc2)OC1=O] | Vitae Pharmaceuticals | 11β-HSD1 > 2 | (6) |
| 82 | 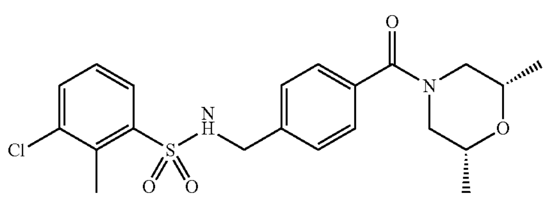 [SMILES: Cc1c(Cl)cccc1S(=O)(=O)NCc1ccc(C(=O)N2C[C@@H](C)O[C@@H](C)C2)cc1] | Shanghai Institute of Materia Medica | 11β-HSD1 > 2 | (6) |
| 83 | 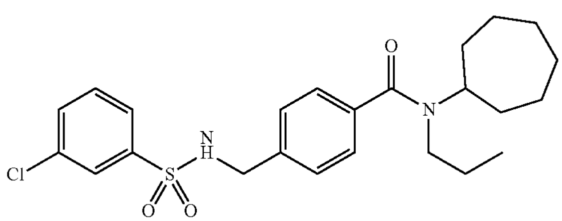 [SMILES: CCCN(C(=O)c1ccc(CNS(=O)(=O)c2cccc(Cl)c2)cc1)C1CCCCCC1] | Shanghai Institute of Materia Medica | 11β-HSD1 > 2 | (6) |
| 84 | 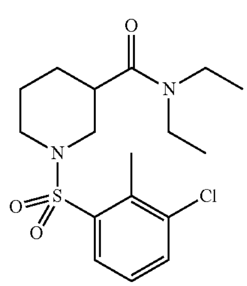 [SMILES: CCN(CC)C(=O)C1CCCN(S(=O)(=O)c2cccc(Cl)c2C)C1] | Shanghai Institute of Materia Medica | 11β-HSD1 > 2 | (6) |

TABLE 1-continued

Chemical structure of 11β-HSD inhibitor families.

| Number | Molecular structure | Name | Specificity | References |
|---|---|---|---|---|
| 85 | 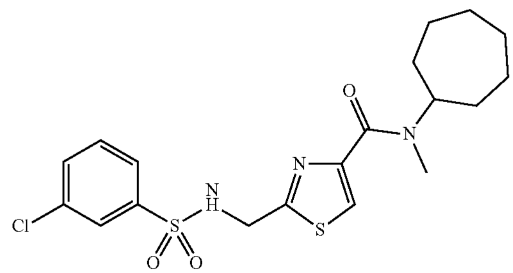 [SMILES: CN(C(=O)c1csc(CNS(=O)(=O)c2cccc(Cl)c2)n1)C1CCCCCC1] | Shanghai Institute of Materia Medica | 11β-HSD1 > 2 | (6) |
| 86 | 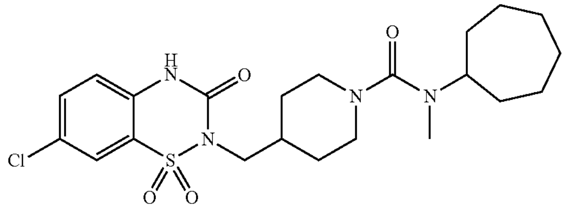 [SMILES: CN(C(=O)N1CCC(CN2C(=O)Nc3ccc(Cl)cc3S2(=O)=O)CC1)C1CCCCCC1] | Shanghai Institute of Materia Medica | 11β-HSD1 > 2 | (6) |
| 87 | 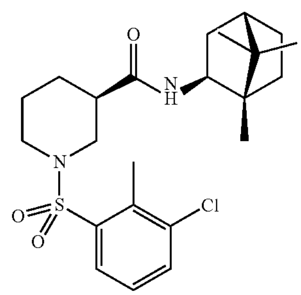 [SMILES: Cc1c(Cl)cccc1S(=O)(=O)N1CCC[C@@H](C(=O)N[C@H]2C[C@@H]3CC[C@@]2(C)C3(C)C)C1] | Shanghai Institute of Materia Medica | 11β-HSD1 > 2 | (6) |
| 88 | 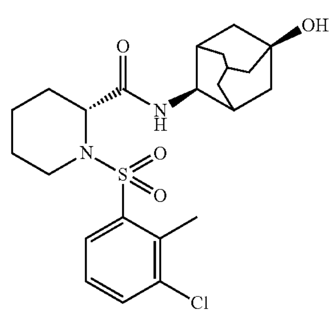 [SMILES: Cc1c(Cl)cccc1S(=O)(=O)N1CCCC[C@@H]1C(=O)N[C@H]1C2CC3CC1C[C@](O)(C3)C2] | Shanghai Institute of Materia Medica | 11β-HSD1 > 2 | (6) |
| 89 | 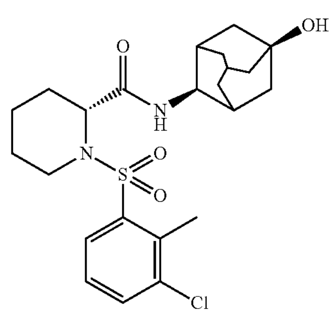 [SMILES: Cc1c(Cl)cccc1S(=O)(=O)N1CCCC[C@@H]1C(=O)N[C@H]1C2CC3CC1C[C@](O)(C3)C2] | Shanghai Institute of Materia Medica | 11β-HSD1 > 2 | (6) |

TABLE 1-continued

Chemical structure of 11β-HSD inhibitor families.

| Number | Molecular structure | Name | Specificity | References |
|---|---|---|---|---|
| 90 | 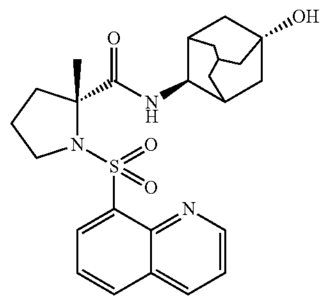 [SMILES: C[C@]1(C(=O)N[C@H]2C3CC4CC2C[C@@](O)(C4)C3)CCCN1S(=O)(=O)c1cccc2cccnc12] | Shanghai Institute of Materia Medica | 11β-HSD1 > 2 | (6) |
| 91 | (KR-66344) | Korea Research Institute of Chemical Technology (KR-66344) | 11β-HSD1 > 2 | (6) |
| 92 | 102 R = Me<br>103 R = H (KR-67183) | Korea Research Institute of Chemical Technology (KR-67183) | 11β-HSD1 > 2 | (6) |
| 93 | 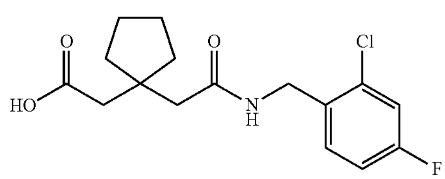 [SMILES: O=C(O)CC1(CC(=O)NCc2ccc(F)cc2Cl)CCCC1] | Merk-Serono | 11β-HSD1 > 2 | (6) |
| 94 | 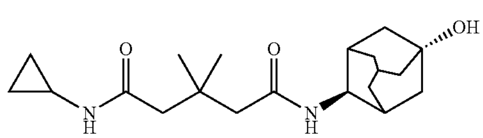 [SMILES: CC(C)(CC(=O)NC1CC1)CC(=O)N[C@H]1C2CC3CC1C[C@@](O)(C3)C2] | Merk-Serono | 11β-HSD1 > 2 | (6) |
| 95 | 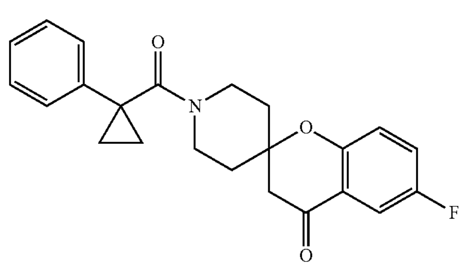 [SMILES: O=C1CC2(CCN(C(=O)C3(c4ccccc4)CC3)CC2)Oc2ccc(F)cc21] | Merk-Serono | 11β-HSD1 > 2 | (6) |

TABLE 1-continued

Chemical structure of 11β-HSD inhibitor families.

| Number | Molecular structure | Name | Specificity | References |
|---|---|---|---|---|
| 96 | 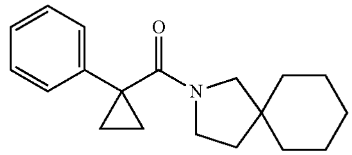 [SMILES: O=C(N1CCC2(CCCCC2)C1)C1(c2ccccc2)CC1] | Merk-Serono | 11β-HSD1 > 2 | (6) |
| 97 | 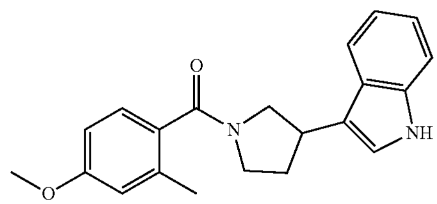 [SMILES: COc1ccc(C(=O)N2CCC(c3c[nH]c4ccccc34)C2)c(C)c1] | Merk-Serono | 11β-HSD1 > 2 | (6) |
| 98 | 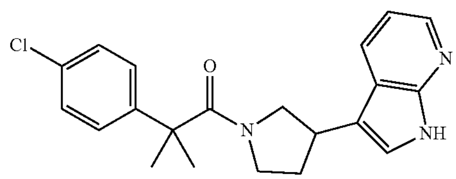 [SMILES: CC(C)(C(=O)N1CCC(c2c[nH]c3ncccc23)C1)c1ccc(Cl)cc1] | Merk-Serono | 11β-HSD1 > 2 | (6) |
| 99 | 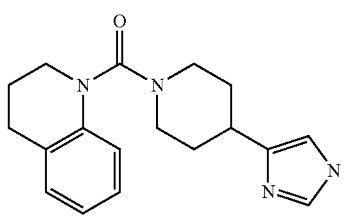 [SMILES: O=C(N1CCC(c2c[nH]cn2)CC1)N1CCCc2ccccc21] | Sanofi | 11β-HSD1 > 2 | (6) |
| 100 | 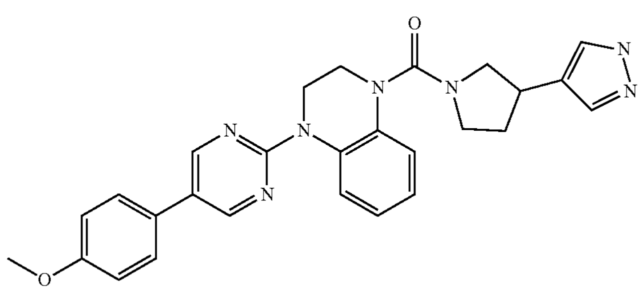 [SMILES: COc1ccc(-c2cnc(N3CCN(C(=O)N4CCC(c5cn[nH]c5)C4)c4ccccc43)nc2)cc1] | Sanofi | 11β-HSD1 > 2 | (6) |
| 101 | 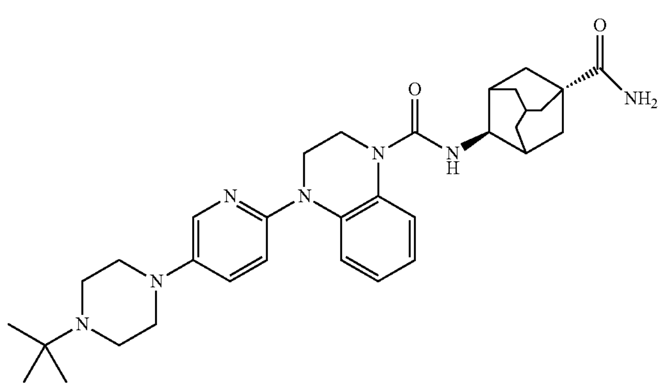 | Sanofi SAR184841 | 11β-HSD1 > 2 | (6) |

112 (SAR184841)

TABLE 1-continued

Chemical structure of 11β-HSD inhibitor families.

| Number | Molecular structure | Name | Specificity | References |
|---|---|---|---|---|
| 102 | 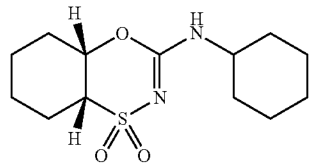 [SMILES: O=S1(=O)N=C(NC2CCCCC2)O[C@H]2CCCC[C@H]21] | Sanofi SAR184841 | 11β-HSD1 > 2 | (6) |
| 103 | 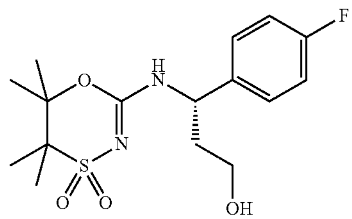 [SMILES: CC1(C)OC(N[C@@H](CCO)c2ccc(F)cc2)=NS(=O)(=O)C1(C)C] | Sanofi SAR184841 | 11β-HSD1 > 2 | (6) |
| 104 | 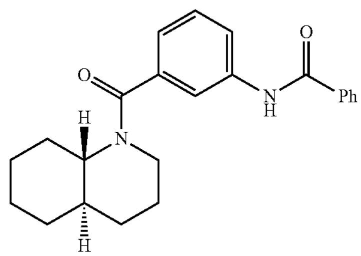 [SMILES: O=C(Nc1cccc(C(=O)N2CCC[C@H]3CCCC[C@@H]32)c1)c1ccccc1] | Novartis | 11β-HSD1 > 2 | (95) |
| 105 | 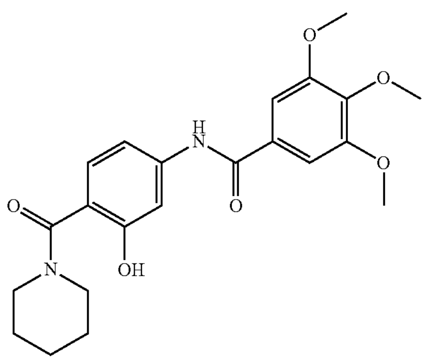 [SMILES: COc1cc(C(=O)Nc2ccc(C(=O)N3CCCCC3)c(O)c2)cc(OC)c1OC] | Novartis | 11β-HSD1 > 2 | (6) |
| 106 | 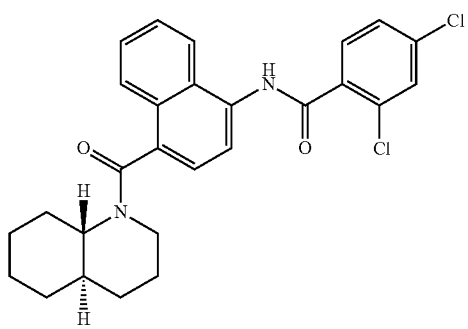 [SMILES: O=C(Nc1ccc(C(=O)N2CCC[C@H]3CCCC[C@@H]32)c2ccccc12)c1ccc(Cl)cc1Cl] | Novartis | 11β-HSD1 > 2 | (6) |
| 107 | 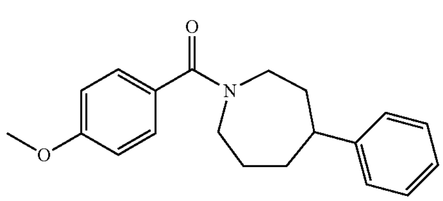 [SMILES: COc1ccc(C(=O)N2CCCC(c3ccccc3)CC2)cc1] | Schering-Plough | 11β-HSD1 > 2 | (6) |

TABLE 1-continued

Chemical structure of 11β-HSD inhibitor families.

| Number | Molecular structure | Name | Specificity | References |
|---|---|---|---|---|
| 108 | 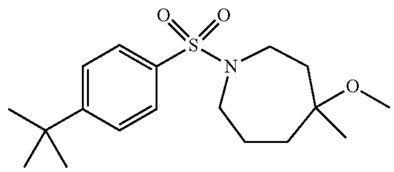 [SMILES: COC1(C)CCCN(S(=O)(=O)c2ccc(C(C)(C)C)cc2)CC1] | Schering-Plough | 11β-HSD1 > 2 | (6) |
| 109 | 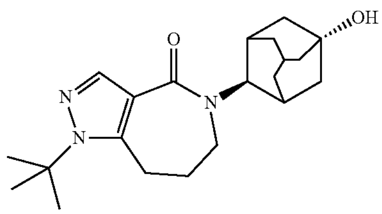 [SMILES: CC(C)(C)n1ncc2c1CCCN([C@H]1C3CC4CC1C[C@@](O)(C4)C3)C2=O] | Toray | 11β-HSD1 > 2 | (6) |
| 110 | 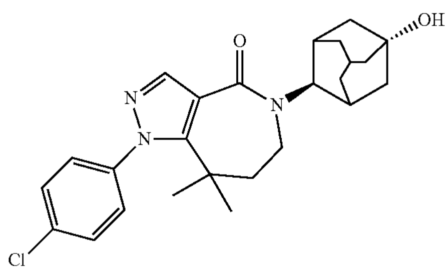 [SMILES: CC1(C)CCN([C@H]2C3CC4CC2C[C@@](O)(C4)C3)C(=O)c2cnn(-c3ccc(Cl)cc3)c21] | Toray | 11β-HSD1 > 2 | (6) |
| 111 | 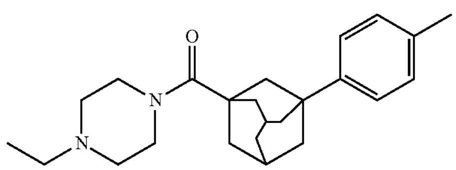 [SMILES: CCN1CCN(C(=O)C23CC4CC(C2)CC(c2ccc(C)cc2)(C4)C3)CC1] | The University of Edinburgh | 11β-HSD1 > 2 | (6) |
| 112 | 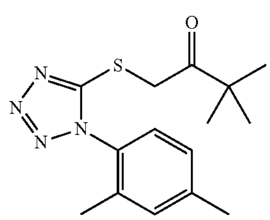 [SMILES: Cc1ccc(-n2nnnc2SCC(=O)C(C)(C)C)c(C)c1] | The University of Edinburgh | 11β-HSD1 > 2 | (6) |
| 113 | 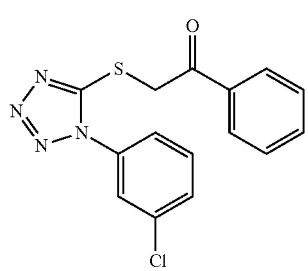 [SMILES: O=C(CSc1nnnn1-c1cccc(Cl)c1)c1ccccc1] | The University of Edinburgh | 11β-HSD1 > 2 | (95) |
| 114 | (UE1961) | The University of Edinburgh | 11β-HSD1 > 2 | (6) |

TABLE 1-continued

Chemical structure of 11β-HSD inhibitor families.

| Number | Molecular structure | Name | Specificity | References |
|--------|--------------------|------|-------------|------------|
| 115 | 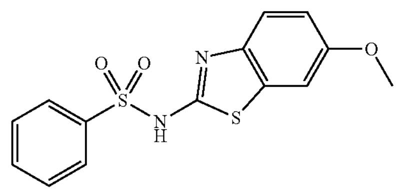 [SMILES: COc1ccc2nc(NS(=O)(=O)c3ccccc3)sc2c1] | The University of Edinburgh | 11β-HSD1 > 2 | (6) |
| 116 | 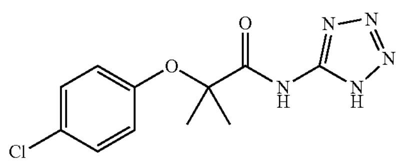 [SMILES: CC(C)(Oc1ccc(Cl)cc1)C(=O)Nc1nnn[nH]1] | The University of Edinburgh | 11β-HSD1 > 2 | (6) |
| 117 | 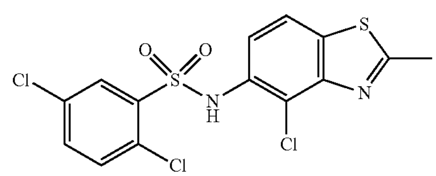 [SMILES: Cc1nc2c(Cl)c(NS(=O)(=O)c3cc(Cl)ccc3Cl)ccc2s1] | University of Bath | 11β-HSD1 > 2 | (6) |
| 118 | 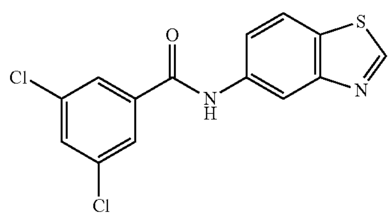 [SMILES: O=C(Nc1ccc2scnc2c1)c1cc(Cl)cc(Cl)c1] | University of Bath | 11β-HSD1 > 2 | (6) |
| 119 | 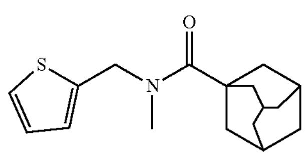 [SMILES: CN(Cc1cccs1)C(=O)C12CC3CC(CC(C3)C1)C2] | University of Bath | 11β-HSD1 > 2 | (6) |
| 120 | 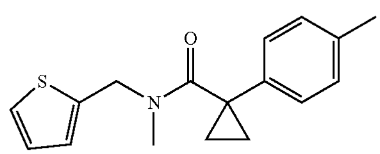 [SMILES: Cc1ccc(C2(C(=O)N(C)Cc3cccs3)CC2)cc1] | University of Bath | 11β-HSD1 > 2 | (6) |
| 121 | 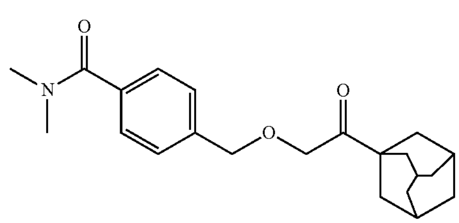 [SMILES: CN(C)C(=O)c1ccc(COCC(=O)C23CC4CC(CC(C4)C2)C3)cc1] | University of Bath | 11β-HSD1 > 2 | (6) |
| 122 | 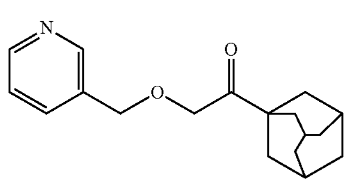 [SMILES: O=C(COCc1cccnc1)C12CC3CC(CC(C3)C1)C2] | | | |

TABLE 1-continued
Chemical structure of 11β-HSD inhibitor families.
| Number | Molecular structure | Name | Specificity | References |
|---|---|---|---|---|
| 123 | 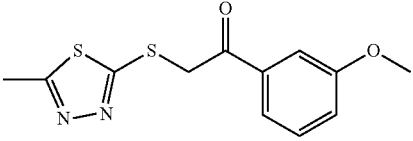 | University of Bath | 11β-HSD1 > 2 | (6) |
| 124 | 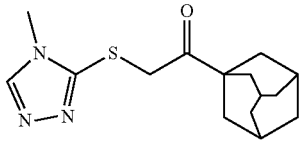 [SMILES: Cn1cnnc1SCC(=O)C12CC3CC(CC(C3)C1)C2] | University of Bath | 11β-HSD1 > 2 | (6) |
| 125 | 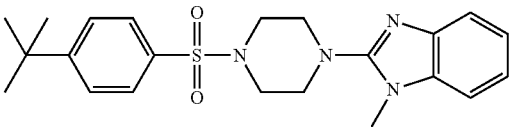 [SMILES: Cn1c(N2CCN(S(=O)(=O)c3ccc(C(C)(C)C)cc3)CC2)nc2ccccc21] | The University Innsbruck | 11β-HSD1 > 2 | (6) |
| 126 | 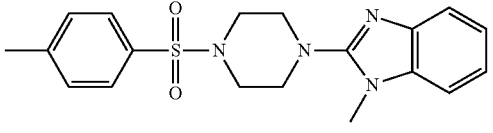 [SMILES: Cc1ccc(S(=O)(=O)N2CCN(c3nc4ccccc4n3C)CC2)cc1] | The University Innsbruck | 11β-HSD1 > 2 | (6) |
| 127-130 | 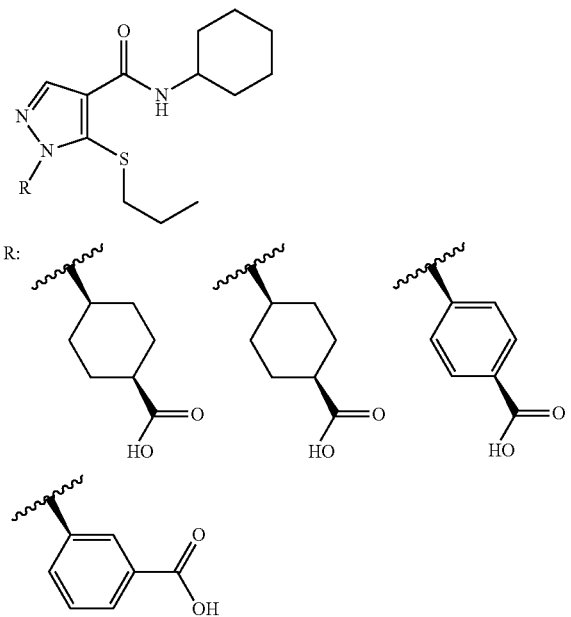 | 1N-Substituted Pyrazoles | | (94) |

TABLE 1-continued
Chemical structure of 11β-HSD inhibitor families.
| Number | Molecular structure | Name | Specificity | References |
|---|---|---|---|---|
| 131-137 | 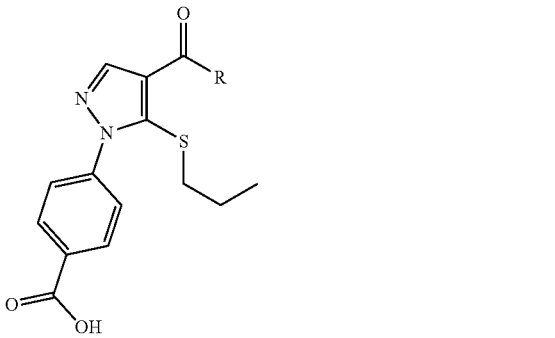 | Amide variations | | (94) |
| 138-142 | 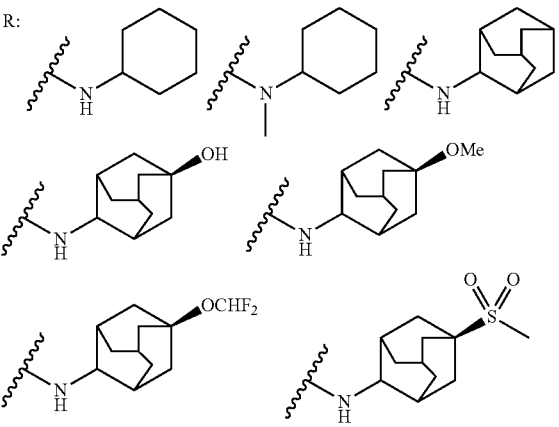 | Thioalkyl Pyrazoles 1N-Substituted Pyrazoles | | (94) |

TABLE 1-continued
Chemical structure of 11β-HSD inhibitor families.
| Number | Molecular structure | Name | Specificity | References |
|---|---|---|---|---|
| 131-137 | 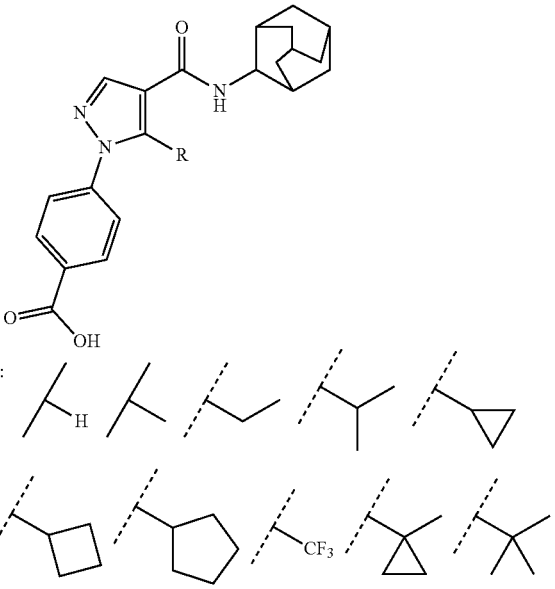 | AZD8329 and other Nonthioalkyl Pyrazoles | | (94) |
| 153-213 | 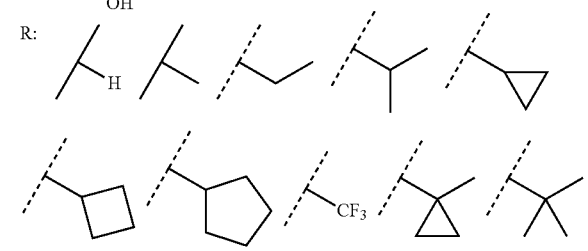<br>$R_1$ = H, 4-Cl, 4-$CH_3$, 4-$COOC_2H_5$, 3-$NO_2$<br>$R_2$ = H, 4-Cl, 4-$CH_3$, 4-$OCH_3$, 4-$COOC_2H_5$, 3-$NO_2$ | 1,4-Diaryl-1,4-dihydropyrazine derivatives | | (96) |
| $R_1$ | $R_2$ | | | |
|---|---|---|---|---|
| H | H | 1,4-Diaryl-1,4-dihydropyrazine derivatives | | (96) |
| H | 4-Cl | | | |
| H | 4-OH | | | |
| H | 4-$CH_3$ | | | |
| H | 4-$CF_3$ | | | |
| H | 4-$OCH_3$ | | | |

TABLE 1-continued

Chemical structure of 11β-HSD inhibitor families.

| Number | Molecular structure | | Name | Specificity | References |
|---|---|---|---|---|---|
| | H | 4-$CH_2OH$ | | | |
| | H | 4-COOH | | | |
| | H | 4-$COOC_2H_5$ | | | |
| | 4-Cl | H | | | |
| | 4-Cl | 4-Cl | | | |
| | 4-Cl | 4-$CH_3$ | | | |
| | 4-Cl | 4-$CF_3$ | | | |
| | 4-Cl | 4-$OCH_3$ | | | |
| | 4-Cl | 4-$CH_2OH$ | | | |
| | 4-Cl | 4-COOH | | | |
| | 4-Cl | 4-$COOC_2H_5$ | | | |
| | 4-OH | 4-OH | | | |
| | 4-$CH_3$ | H | | | |
| | 4-$CH_3$ | 4-Cl | | | |
| | 4-$CH_3$ | 4-OH | | | |
| | 4-$CH_3$ | 4-$CH_3$ | | | |
| | 4-$CH_3$ | 4-$CF_3$ | | | |
| | 4-$CH_3$ | 4-$OCH_3$ | | | |
| | 4-$CH_3$ | 4-$CH_2OH$ | | | |
| | 4-$CH_3$ | 4-$COOC_2H_5$ | | | |
| | 4-$CF_3$ | H | | | |
| | 4-$CF_3$ | 4-Cl | | | |
| | 4-$CF_3$ | 4-OH | | | |
| | 4-$CF_3$ | 4-$CH_3$ | | | |
| | 4-$CF_3$ | 4-$CF_3$ | | | |
| | 4-$CF_3$ | 4-$OCH_3$ | | | |
| | 4-$CF_3$ | 4-$CH_2OH$ | | | |
| | 4-$CF_3$ | 4-COOH | | | |
| | 4-$CF_3$ | 4-$COOC_2H_5$ | | | |
| | 4-$CH_2OH$ | H | | | |
| | 4-$CH_2OH$ | 4-Cl | | | |
| | 4-$CH_2OH$ | 4-OH | | | |
| | 4-$CH_2OH$ | 4-$CH_3$ | | | |
| | 4-$CH_2OH$ | 4-$OCH_3$ | | | |
| | 4-$CH_2OH$ | 4-$CH_2OH$ | | | |
| | 4-$CH_2OH$ | 4-COOH | | | |
| | 4-$CH_2OH$ | 4-$COOC_2H_5$ | | | |
| | 4-COOH | H | | | |
| | 4-COOH | 4-Cl | | | |
| | 4-COOH | 4-OH | | | |
| | 4-COOH | 4-$CH_3$ | | | |
| | 4-COOH | 4-$CF_3$ | | | |
| | 4-COOH | 4-$OCH_3$ | | | |
| | 4-COOH | 4-$CH_2OH$ | | | |
| | 4-COOH | 4-COOH | | | |
| | 4-COOH | 4-$COOC_2H_5$ | | | |
| | 4-$COOC_2H_5$ | H | | | |
| | 4-$COOC_2H_5$ | 4-Cl | | | |
| | 4-$COOC_2H_5$ | 4-OH | | | |
| | 4-$COOC_2H_5$ | 4-$CH_3$ | | | |

TABLE 1-continued

Chemical structure of 11β-HSD inhibitor families.

| Number | Molecular structure | | Name | Specificity | References |
|---|---|---|---|---|---|
| | 4-COOC$_2$H$_5$ | 4-CF$_3$ | | | |
| | 4-COOC$_2$H$_5$ | 4-OCH$_3$ | | | |
| | 4-COOC$_2$H$_5$ | 4-CH$_2$OH | | | |
| | 4-COOC$_2$H$_5$ | 4-COOC$_2$H$_5$ | | | |
| | 3-NO$_2$ | 3-NO$_2$ | | | |
| 214-235 | (triterpenoid structure with CONHR group) | | 11β-HSD1 > 2 | | (97) |

R:

CH$_2$CH$_2$CH$_2$CH$_3$, cyclopropyl, CH(CH$_3$)COOEt, CH(CH$_3$)COOH

CH$_2$CH$_2$OH, CH$_2$(CH$_2$)$_4$OH, CH$_2$CH$_2$NHCH$_3$, (γ-butyrolactone)

CH(CH$_2$CH$_2$OH)CO$_2$H, (ethyl-morpholine)

(morpholine), (ethyl-piperazine-NH)

(piperazine-N-methyl), (ethyl-piperazine-NH)

(ethyl-piperidine), (ethyl-pyrrolidine)

(pyrrolidine), CH$_2$C$_6$H$_5$, (2-picolyl), (3-picolyl)

(4-picolyl), (2-pyridylethyl)

TABLE 1-continued
Chemical structure of 11β-HSD inhibitor families.
| Number | Molecular structure | Name | Specificity | References |
|---|---|---|---|---|
| 236-242 | 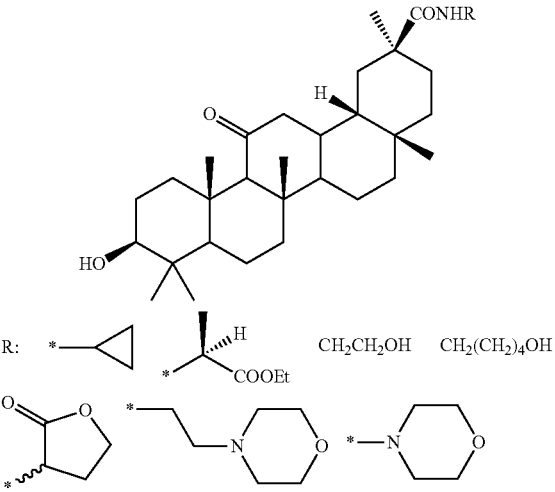 R: cyclopropyl, *CH(COOEt)H, $CH_2CH_2OH$, $CH_2(CH_2)_4OH$, γ-butyrolactone, *$CH_2CH_2$-morpholine, *N-morpholine | | 11β-HSD1 > 2 | (98) |
| 243-247 | 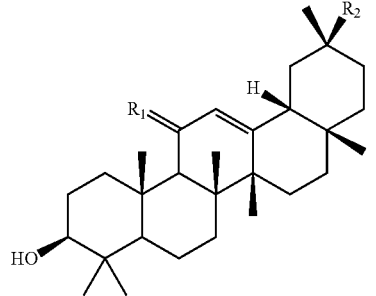 $R_1$ = α-$CH_3$' β-OH, $R_2$ = COOH<br>$R_1$ = $CH_2$' $R_2$ = COOH<br>$R_1$ = O, $R_2$ = 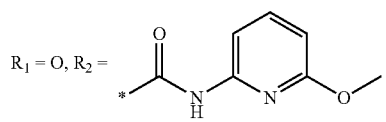<br>$R_1$ = O, $R_2$ = $CH_2OCH_2CH_2OCH_2$<br>$R_1$ = O, $R_2$ = $CH_2OH$ | | 11β-HSD1 > 2 | (99) |
| 248 | 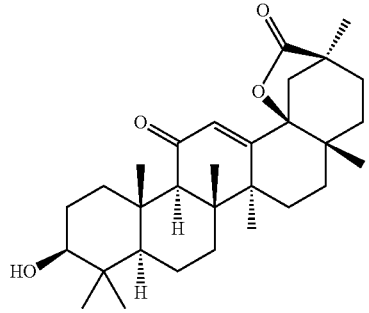 | | 11β-HSD1 > 2 | (42) |

TABLE 1-continued
Chemical structure of 11β-HSD inhibitor families.
| Number | Molecular structure | Name | Specificity | References |
|---|---|---|---|---|
| 249 | 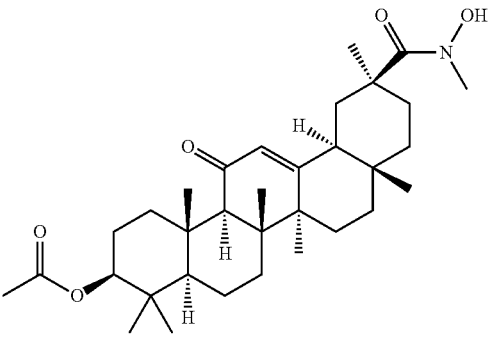 | | 11β-HSD1 > 2 | (42) |
| 250 | 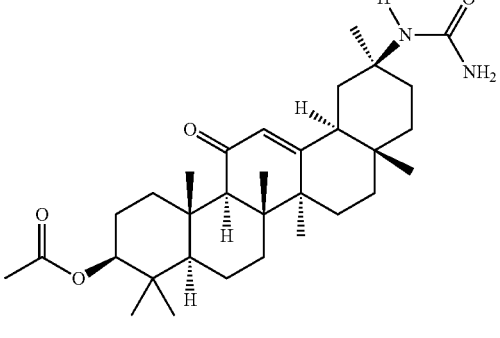 | | 11β-HSD1 > 2 | (42) |
| 251 | 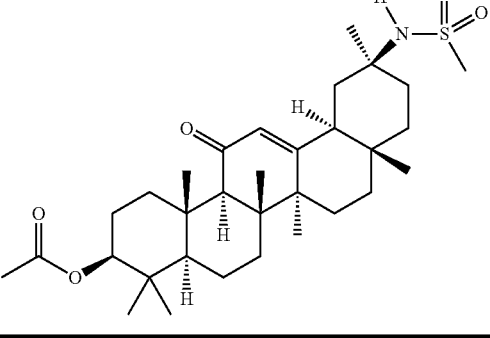 | | 11β-HSD1 > 2 | (42) |

Carbenoxolone is also known to block gap junctions and pannexins (100). Table II, below, provides a list of gap junction and pannexin inhibitors that because of their inhibition activity, use of any of them is contemplated in the context of the invention to be used for treating a patient who is in need of decreasing intake of alcohol due to an alcohol abuse disease or disorder.

TABLE II

| | Chemical structure of Pannexin inhibitors | | | |
|---|---|---|---|---|
| Number | Molecular structure | Name | Specificity | References |
| 256 | 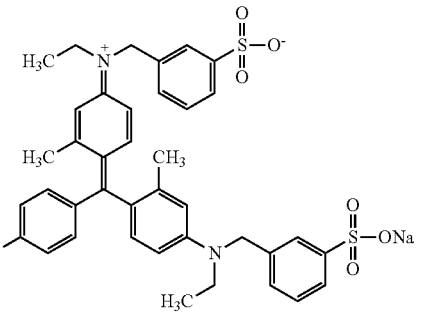 | Acid blue 90, Coomassie Brilliant Blue G | | (105) |
| 257 | 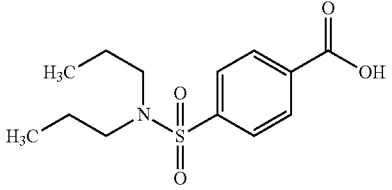 [SMILES: CCCN(CCC)S(=O)(=O)c1ccc(C(=O)O)cc1] | Probenecid | | (101, 102) |
| 258 | 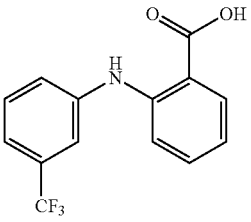 [SMILES: O=C(O)c1ccccc1Nc1cccc(C(F)(F)F)c1] | flufenamic acid | | (104, 107) |
| 259 | 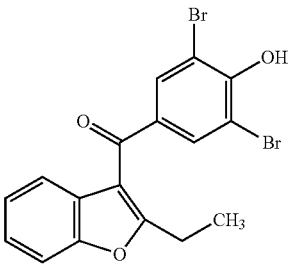 [SMILES: CCc1oc2ccccc2c1C(=O)c1cc(Br)c(O)c(Br)c1] | Benzbromarone 3-(3,5-Dibromo-4-hydroxybenzo-yl)-2-ethylbenzofuran | | (100) |
| 260 | 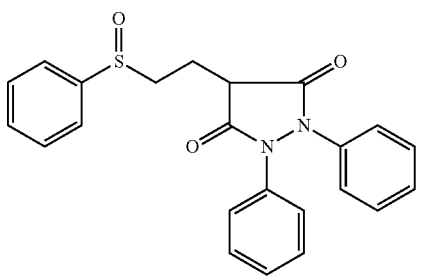 [SMILES: O=C1C(CCS(=O)c2ccccc2)C(=O)N(c2ccccc2)N1c1ccccc1] | Sulfinpyrazone, 1,2-Diphenyl-4-(phenylsulfinyl-ethyl)-3,5-pyrazolidinedione, Diphenylpyrazone | | (100) |

TABLE II-continued

Chemical structure of Pannexin inhibitors

| Number | Molecular structure | Name | Specificity | References |
|---|---|---|---|---|
| 261 | 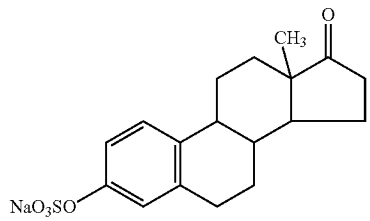 | Estrone sulfate, 1,3,5(10)-Estratrien-17-one 3-sulfate | | (100) |
| 262 | 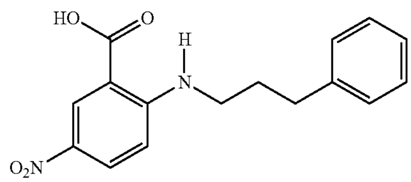 [SMILES: O=C(O)c1cc([N+](=O)[O-])ccc1NCCCc1ccccc1] | NPPB, 5-Nitro-2-(3-phenylpropyl-amino)benzoic acid, CAS Number: 107254-86-4 | | (100, 101) |
| 263 | 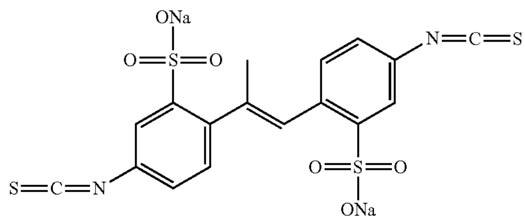 | disodium 4,40-diisothiocyanato-stilbene-2,20-disulfonate | | (100) |
| 264 | 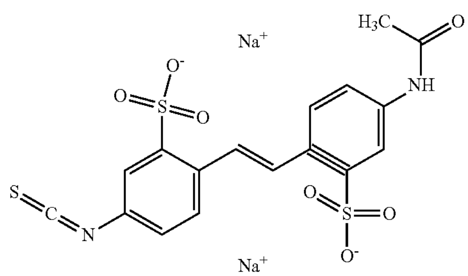 | SITS, disodium 4-acet-amido-4,-isothio-cyanato-stilben-2,2'-disulfonate;s | | (100) |
| 265 | 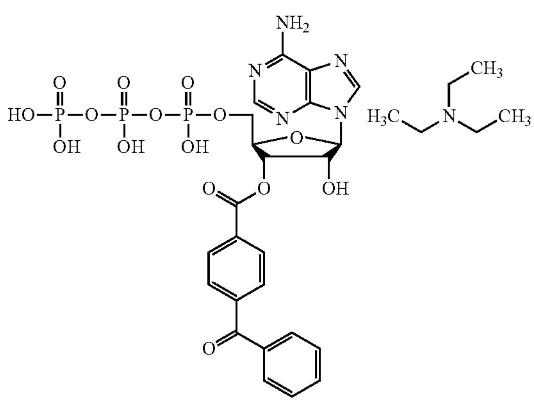 | 2'(3')-O-(4-Benzoylbenzoyl)-adenosine 5'-triphosphate triethyl-ammonium salt, Benzoylbenzoyl-ATP, Bz-ATP | | (100) |
| 266 | 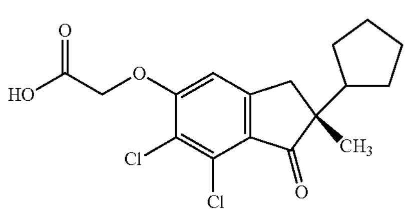 [SMILES: C[C@]1(C2CCCC2)Cc2cc(OCC(=O)O)c(Cl)c(Cl)c2C1=O] | IAA94, Indanyloxyacetic acid 94, R(+)-Methylindazone, R(+)-[(6,7-Dichloro-2-cyclopentyl-2,3-dihydro-2-methyl-1-oxo-1H-inden-5-yl)-oxy]acetic acid | | (100) |

TABLE II-continued

Chemical structure of Pannexin inhibitors

| Number | Molecular structure | Name | Specificity | References |
|---|---|---|---|---|
| 267 | 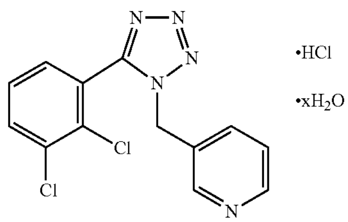 [SMILES: Clc1cccc(-c2nnnn2Cc2cccnc2)c1Cl ; Cl] | A438079 | | (100) |
| 268 | 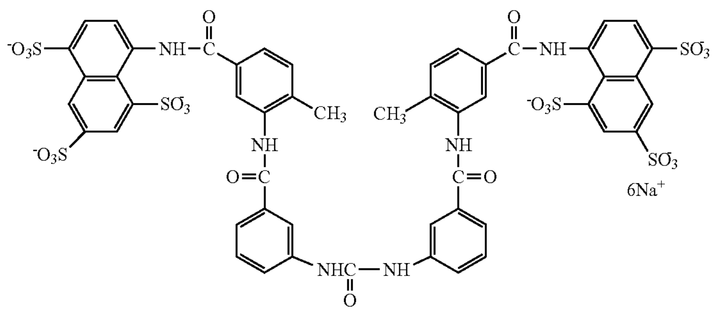 | Suramin | | (100) |
| 269 | 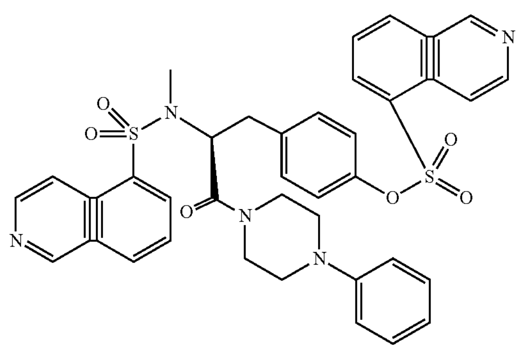 [SMILES: CN([C@@H](Cc1ccc(OS(=O)(=O)c2cccc3c2-c2ccncc2-3)cc1)C(=O)N1CCN(c2ccccc2)CC1)S(=O)(=O)c1cccc2c1-c1ccncc1-2] | KN-62 | | (100) |
| 270 | 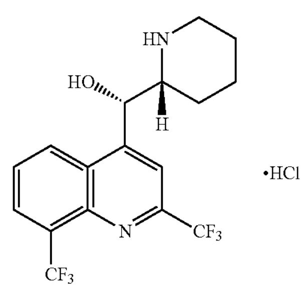 | Mefloquine | | (100) |
| 271 | 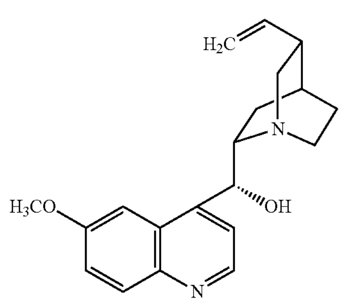 [SMILES: C=CC1CN2CCC1CC2[C@H](O)c1ccnc2ccc(OC)cc12] | Quinine | | (100) |

TABLE II-continued
Chemical structure of Pannexin inhibitors
| Number | Molecular structure | Name | Specificity | References |
|---|---|---|---|---|
| 272 | 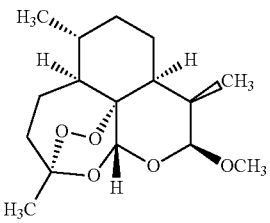 [SMILES: CO[C@H]1O[C@@H]2O[C@@]3(C)CC[C@H]4[C@H](C)CC[C@@H]([C@H]1C)[C@@]24OO3] | Artemether | | (100) |
| 273 | 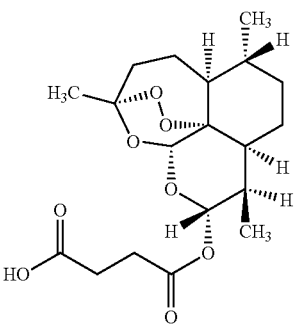 [SMILES: C[C@H]1[C@H](OC(=O)CCC(=O)O)O[C@@H]2O[C@@]3(C)CC[C@H]4[C@H](C)CC[C@@H]1[C@@]24OO3] | Artesunate | | (100) |
| 274 | 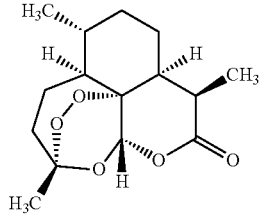 [SMILES: C[C@@H]1CC[C@H]2[C@@H](C)C(=O)O[C@@H]3O[C@]4(C)CC[C@@H]1[C@]32OO4] | Artemisinin | | (100) |
| 275 | 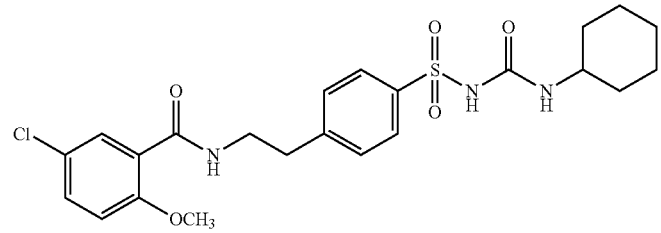 [SMILES: COc1ccc(Cl)cc1C(=O)NCCc1ccc(S(=O)(=O)NC(=O)NC2CCCCC2)cc1] | Glyburide | | (100) |
| 276 | 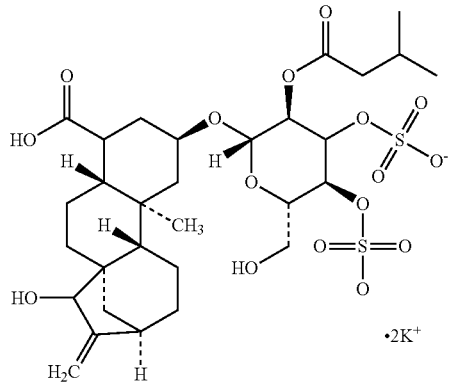 | Atractyloside | | (100) |

TABLE II-continued

Chemical structure of Pannexin inhibitors

| Number | Molecular structure | Name | Specificity | References |
|---|---|---|---|---|
| 277 | 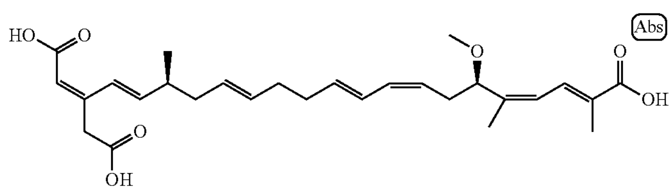 [SMILES: CO[C@H](C/C=C\C=C\CC/C=C/C[C@H](C)/C=C/C(=C\C(=O)O)CC(=O)O)/C(C)=C\C=C(/C)C(=O)O] | Bongkrekic acid | | (100) |
| 278 | 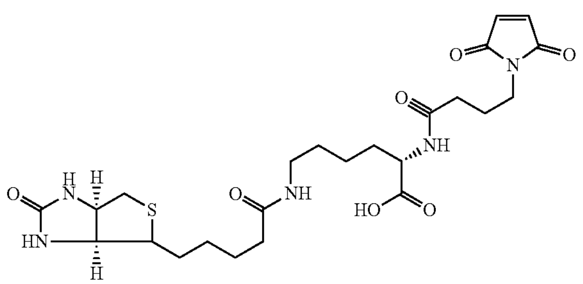 | MBB, maleimido-butyrylbiocytin | | (100) |
| 279 | 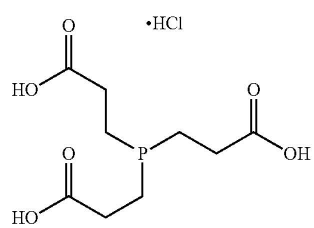 [SMILES: Cl ; O=C(O)CCP(CCC(=O)O)CCC(=O)O] | TCEP, tris (2-carboxyethyl) phosphine | | (100) |
| 280 | SRPTEKTIFII | Gap27 | peptide | (103) |
| 281 | GHGDPLHLEEVKC | Gap24 | peptide | (103) |
| 282 | SSFSWRQAAFVDS | PanxE1b | peptide | (103) |
| 283 | WRQAAFVDSY | Benx1 | peptide | (103) |
| 284 | VCYDKSFPISHVR | Gap26 | peptide | (103) |
| 285 | AQEISIGTQIS | PanxE1a | peptide | (103) |
| 286 | SSLSDEFVCSIKS | PanxE2a | peptide | (103) |
| 287 | KSGILRNDSTVPDQ | PanxE2b | peptide | (103) |
| | | Brilliant Blue FCF (BBFCF) | | (100) |

TABLE II-continued

Chemical structure of Pannexin inhibitors

| Number | Molecular structure | Name | Specificity | References |
|---|---|---|---|---|
| | 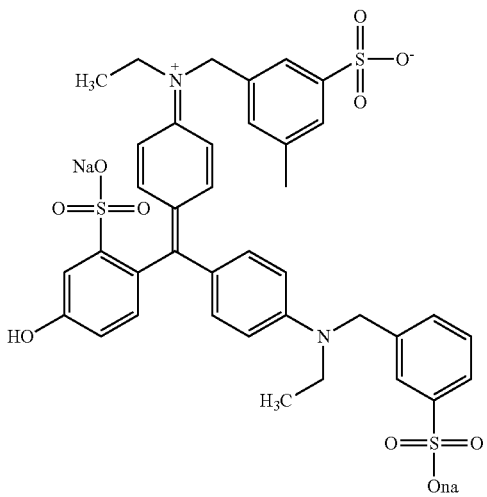 | Fast Green FCF | | (100) |

The antigout drug probenecid inhibits Pannexin 1 and prevents inflammasome activation in neurons and astrocytes (101, 102). Other nonselective transporter inhibitors including sulfinpyrazone and benzbromarone (100). Pannexin 1 is also inhibited by other classes of drugs including Gap junction blockers, transport blockers, Cl channel blockers, malaria drugs, thiol reagents and others (Dahl, et al. 2013) and "mimetic" peptides" such as Gap27, Gap24, PanxE1b, Panx1 (103). Other gap junction inhibitors including flufenamic acid (FFA) were tested on Pannexin 1 and were found to inhibit the channel (104). ATP inhibits Pannexin 1 in a form of negative feedback (105. More potent ATP analogues such as the nonhydrolyzable BZATP inhibit Pannexin 1 more effectively than AYP. The ATP-dependent negative feedback on Pannexin 1 serves two functions. First, negative feedback on Pannexin 1 stops the channel from being open for prolonged periods of time and thus prevents rundown of ionic gradients and cell death (105). Second, the negative feedback ensures that ATP release through Pannexin 1 is transient and elicits a controlled response. The most selective and least detrimental Pannexin 1 inhibitor currently known is the blue dye Brilliant Blue G (BBG or Coomassie Blue) (105). The food dye Brilliant Blue FCF (BBFCF) is structurally similar to BBG and has been hypothesized to have similar effects to those of BBG (106).

A composition for use in accordance with the invention may include the first agent which is an antagonist of 1β-HSD, optionally together with a second agent which comprises a diuretic, preferably an anti-kaliuretic-diuretic, or a fragment, homologue, variant or derivative thereof, a structurally related compound, or an acidic salt of either. The pharmaceutical formulations comprise an effective amount of the first and/or second agent, fragment, homologue, variant or derivative thereof, together with one or more pharmaceutically-acceptable carriers. An "effective amount" is the amount sufficient to alleviate at least one symptom of a disease as described, for example, lessening of alcohol intake and or craving for alcohol.

The effective amount will vary depending upon the particular disease or syndrome to be treated or alleviated, as well as other factors including the age and weight of the patient, how advanced the disease state is, the general health of the patient, the severity of the symptoms, and whether the first and/or second agent or variant or derivative thereof is being administered alone or in combination with other therapies.

Suitable pharmaceutically acceptable carriers are well known in the art and vary with the desired form and mode of administration of the pharmaceutical formulation. For example, they can include diluents or excipients such as fillers, binders, wetting agents, disintegrators, surface-active agents, lubricants and the like. Typically, the carrier is a solid, a liquid or a vaporizable carrier, or a combination thereof. Each carrier should be "acceptable" in the sense of being compatible with the other ingredients in the formulation and not injurious to the patient. The carrier should be biologically acceptable without eliciting an adverse reaction (e.g., immune response) when administered to the host.

EXAMPLES

The following examples are provided for illustrative purposes only and not to limit the scope of the claims provided herein.

Specifically, adult male Wistar rats (Charles River), weighing 225-275 g at the beginning of the experiments, were housed in groups of 2-3 per cage in a temperature-controlled (22° C.) vivarium on a 12 hr/12 hr light/dark cycle (lights on at 8:00 P.M.) with ad libitum access to food and water except during behavioral testing. Male wild-type C57BL/6J obtained from Jackson Laboratories were used for chronic intermittent ethanol exposure (CIE) and the drinking in the dark (DID) procedure.

All behavioral tests were conducted during the dark phase of the light/dark cycle. All procedures adhered to the National Institutes of Health Guide for the Care and Use of Laboratory Animals.

Rat Operant Self-Administration of Alcohol.

Self-administration sessions were conducted in standard operant conditioning chambers (Med Associates). The rats were trained to self-administer alcohol as previously reported (13). First, the rats were given free-choice access to alcohol (10% w/v) and water for 1 day in their home cages to habituate them to the taste of alcohol. Second, the rats were subjected to an overnight session in the operant chambers with access to one lever (right lever) that delivered water in a fixed-ratio 1 (FR1) schedule where every lever press is reinforced with delivery of 0.1 ml of solution. Food was available ad libitum during this training. Third, after 1 day off, the rats were subjected to a 2 hour session (FR1) for 1 day and a 1 hour session (FR1) the next day, with one lever delivering alcohol (right lever). All of the subsequent sessions lasted 30 min, and two levers were available (left lever: water; right lever: alcohol) until stable levels of intake were reached. Upon completion of this procedure, the animals were allowed to self-administer a 10% (w/v) alcohol solution and water on an FR1 schedule of reinforcement.

Rat Alcohol Vapor Chambers.

The rats were made dependent by chronic, intermittent exposure to alcohol vapors as previously described (13). They underwent cycles of 14 hours on (blood alcohol levels during vapor exposure ranged between 150 and 250 mg %) and 10 hours off, during which behavioral testing for acute withdrawal occurred (i.e., 6-8 hours after vapor was turned off when brain and blood alcohol levels are negligible (108). In this model, rats exhibit motivational and somatic withdrawal signs (13, 109-111). Dependent rats were exposed to vapor at least for two months before testing. Nondependent rats were not exposed to alcohol vapor. The same rats were also tested during protracted abstinence, where the animals were tested at the same time of the day as for acute withdrawal but 3-6 weeks after the vapor was turned off.

Rat Operant Self-Administration of Saccharin.

A separate cohort of rats was tested for self-administration of saccharin-sweetened water. A submaximal rewarding saccharin concentration (0.004%, w/v) was chosen based on previous studies (13) to prevent a "ceiling effect" in any group and maintain similar response rates as alcohol. Training for this experiment was identical as for alcohol described above, except that saccharin solution was used.

Mouse 2-Bottle Choice Procedure and Intermittent Ethanol Exposure (CIE) to Model Dependent and Nondependent Drinking.

Exposure of mice to repeated cycles of intermittent ethanol vapor in order to induce dependence increases ethanol drinking following withdrawal in a 2-bottle choice paradigm (112, 113). Thus, the CIE paradigm is used to test the effects of a drug on dependent and nondependent drinking in mice. Briefly, C57BL/6J mutant and WT mice had access to two bottles, one containing water and the other containing 15% (w/v) ethanol, for 2 hours starting 3 hours into the dark phase. Following acquisition of stable alcohol intake, half of the mice were subjected to repeated bouts of ethanol vapor exposure consisting of 16 hours per day for 4 days. Before each exposure to ethanol vapor, mice were IP injected with a solution of 20% v/v ethanol and 68.1 mg/kg pyrazole and immediately placed into ethanol vapor chambers (La Jolla Ethanol Research, CA). Tail blood sampling for blood ethanol level (BAL) determination was carried out daily. Target BALs were 150-200 mg %. Seventy-two hours following removal from the chambers, mice received access to water vs. 20% ethanol for 2 hours, and again over the next 4 days. The following week, mice were re-exposed to the ethanol vapor/control conditions and again tested for t2-bottle choice drinking for 5 days. Three vapor bouts followed by 2-bottle choice were carried out. Mice were weighed every 4-6 days throughout the 2-bottle choice sessions and daily during the vapor exposure bouts. Food and water were available ad libitum and mice were group housed except during the ethanol drinking sessions.

Mouse Drinking in the Dark Procedure (DID) to Model Binge Drinking.

The DID paradigm capitalizes on the circadian rhythm in drinking of mice utilizing a discrete time of exposure to ethanol to obtain pharmacologically significant ethanol drinking in a four-day procedure (114, 115). It is considered a preclinical model of binge alcohol drinking (116). Blood ethanol levels of C57BL/6J mice in DID are reliably over 100 mg % following the final drinking bout and produce behavioral intoxication in C57BL/6J mice (115). In the DID paradigm, the water bottle is replaced with a bottle containing 20% ethanol for 2 hours in the home cage 3 hours after lights go off. The design involves 3 daily drinking sessions of 2 hours and a fourth of 4 hours (114, 115).

Effect of carbenoxolone (CBX) on alcohol drinking in rats and mice. Carbenoxolone was administered acutely systemically by intraperitoneal (IP) injection 90 min before testing at doses of 0, 20, and 40 mg/kg to rats and mice, which are in line with the scientific literature (16, 117-119).

Vapor-exposed alcohol dependent rats, as in previous studies, showed increased lever press responding for alcohol compared with nondependent rats (FIG. 1A; group effect: $F_{(1,\ 17)}=32.9$; $p<0.0001$). Acute intraperitoneal (IP) administration of CBX 90 min before testing dose-dependently reduced responding for alcohol in both dependent and nondependent rats (FIG. 1); dose effect: $F_{(2,\ 34)}=5.0$; $p<0.05$). No significant effects were found for water responding (FIG. 1B). Additionally, no significant effects were found for self-administration of saccharin-sweetened water (FIG. 1C).

Figure 3:
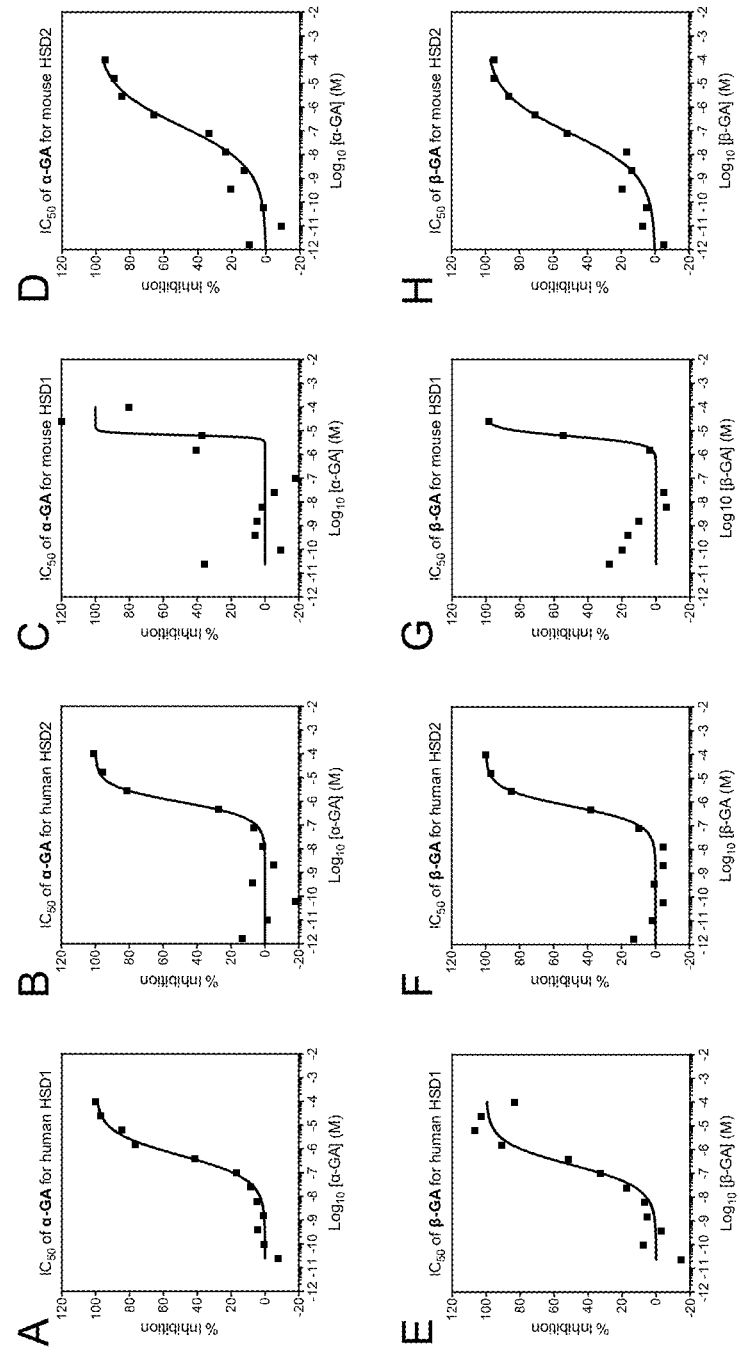
FIGS. 3A-H are graphs showing activity of 18α-glycyrrhetinic acid and 18β-glycyrrhetinic on mouse and human 11β-HSD1 and 2. We tested the IC50 of α and β-glycyrrhetinic acid (GA) against human and mouse 11β-HSD1 and 11β-HSD2 by means of homogeneous time-resolved fluorescence (HTRF) assays. A,C) α-GA yielded IC50 values of 532.1 nM for human 11β-HSD1 and 6.63 μM for mouse 11β-HSD1. B,D) α-GA yielded IC50 values of 942.6 nM for human 11β-HSD2 and 159.7 nM for mouse 11β-HSD2. E,G) β-GA yielded IC50 values of 232.3 nM for human 11β-HSD1 and 5.85 μM for mouse 11β-HSD1. F,H) β-GA yielded IC50 values of 674.5 nM for human 11β-HSD2 and 79.7 nM for mouse 11β-HSD2.
Figure 4:
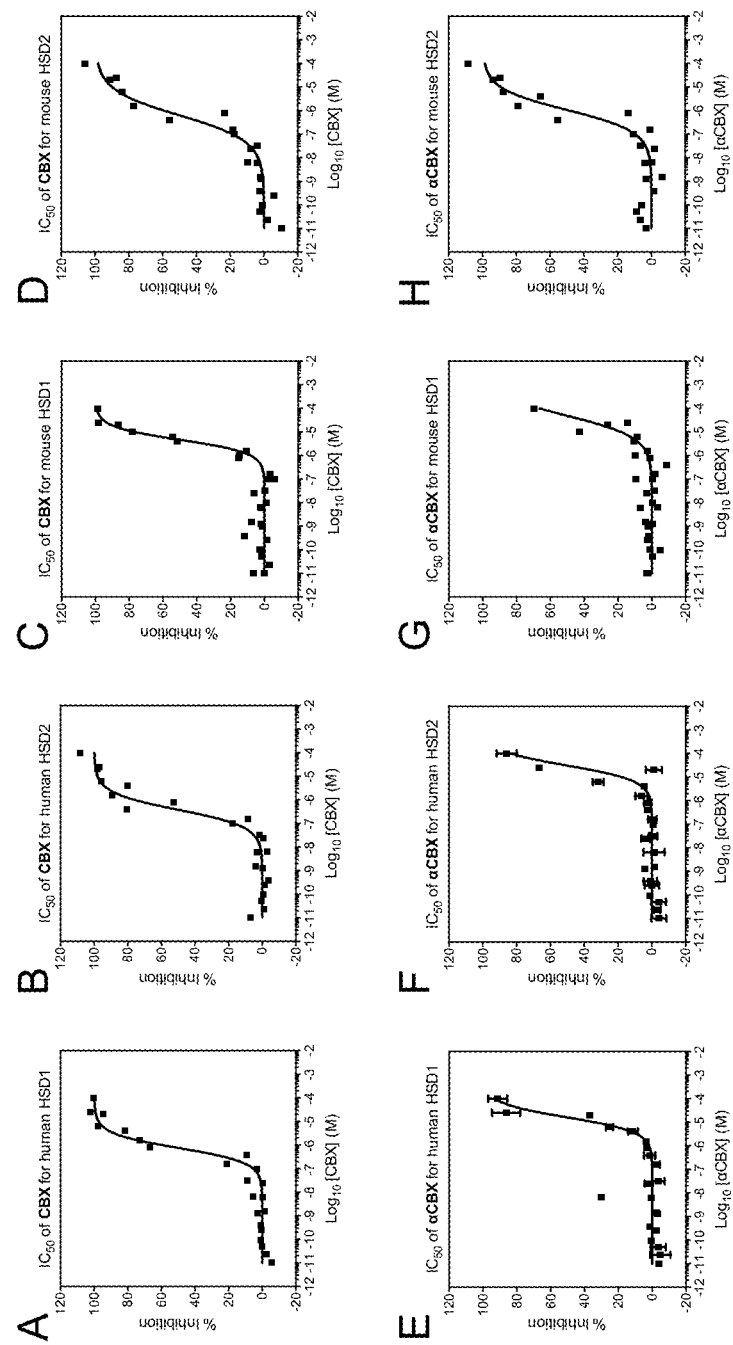
FIGS. 4A-H are graphs showing activity of carbenoxolone (CBX, 18β-glycyrrhetinic acid 3β-O-hemisuccinate), and αCBX (18α-glycyrrhetinic acid 3β-O-hemisuccinate) on mouse and human 11β-HSD1 and 2. We tested the IC50 of 18α-18β-glycyrrhetinic acid 3β-O-hemisuccinate against human and mouse 11β-HSD1 and 11β-HSD2 by means of homogeneous time-resolved fluorescence (HTRF) assays. A,C) CBX yielded IC50 values of 753.1 nM for human 11β-HSD1 and 4.62 μM for mouse 11β-HSD1. B,D) CBX yielded IC50 values of 379.6 nM for human 11β-HSD2 and 628.7 nM for mouse 11β-HSD2. E,G) αCBX yielded IC50 values of 15.92 μM for human 11β-HSD1 and 48.25 μM for mouse 11β-HSD1. F,H) αCBX yielded IC50 values of 30.67 μM for human 11β-HSD2 and 1.06 μM for mouse 11β-HSD2. Results for CBX are the average of 2-3 independent replicates; results for αCBX are the average of 3-4 independent replicates.
Figure 5:
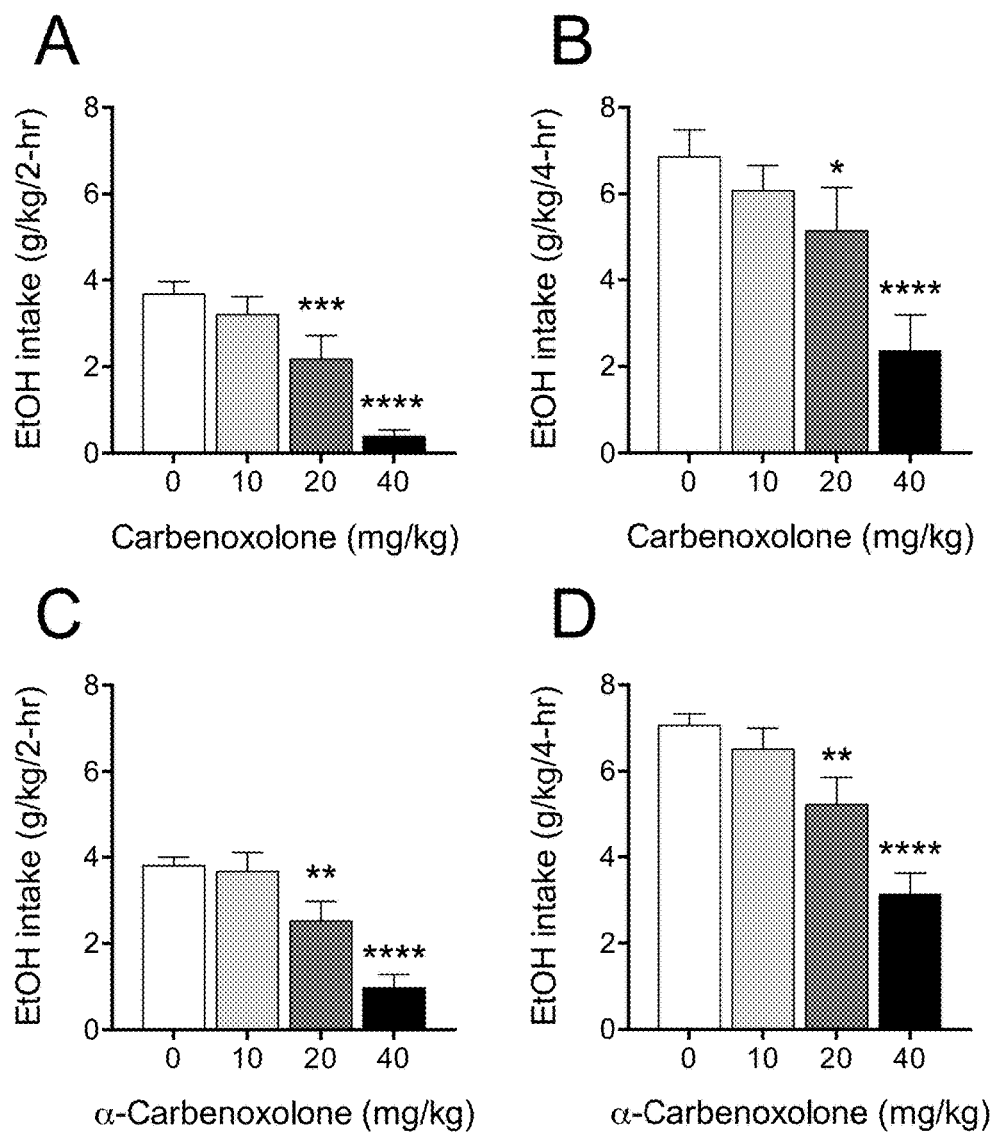
FIGS. 5A-D are graphs showing CBX and αCBX reduce ethanol intake in mice in the drinking in the dark (DID) paradigm. A-B) CBX reduced ethanol intake in the DID binge-like drinking paradigm. A) CBX effect on ethanol intake in the first 2 hours of the 4 h drinking session ($F_{3, 30}$=26.00, p<0.0001); B) CBX effect on ethanol intake for the 4 h drinking session ($F_{3, 30}$=10.82, p<0.0001); C) αCBX effect on ethanol intake in the first 2 h of the 4 h drinking session ($F_{3, 86}$=15.66, p<0.0001); D) αCBX effect on ethanol intake for the 4 h drinking session ($F_{3, 86}$=18.51, p<0.0001). The effects of CBX and αCBX were more pronounced in the first 2 hours of the session, suggesting an effect on initiation of drinking. *p<0.05, p<0.01, *p<0.001, significant difference from respective saline vehicle (N=11-15).
Figure 6:
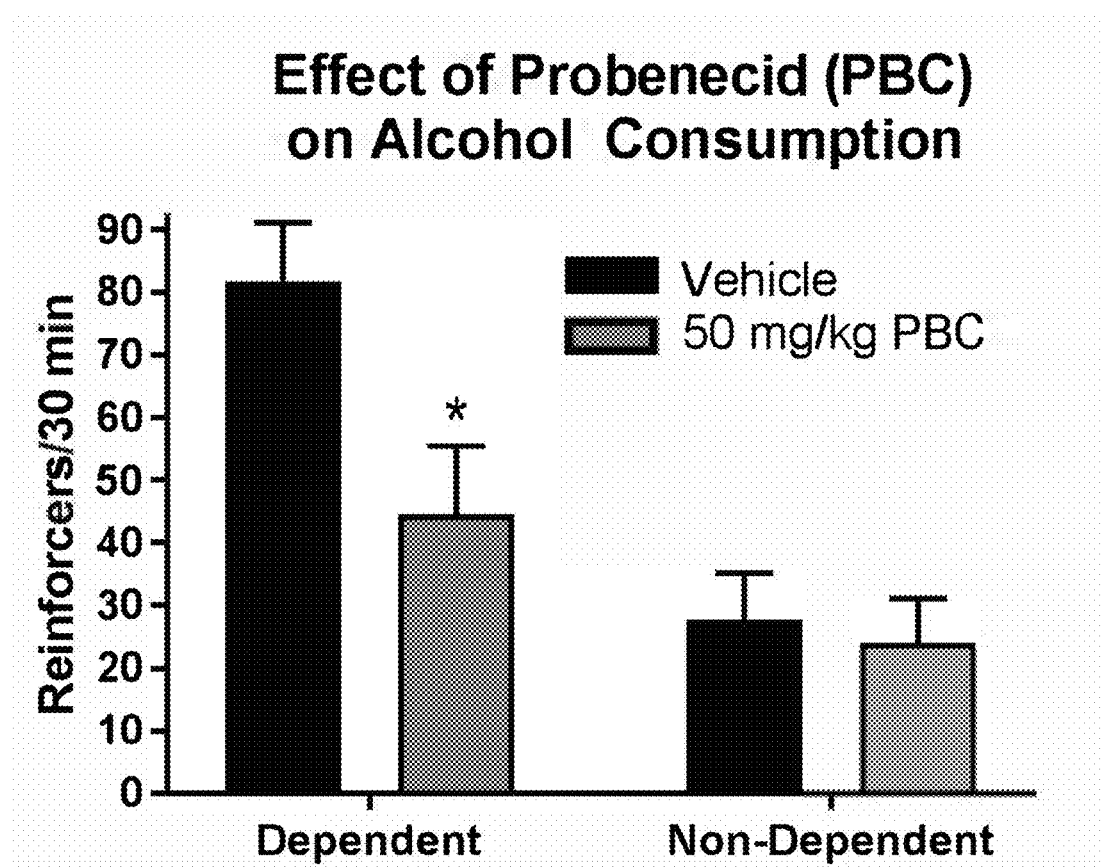
FIG. 6 is a graph showing acute, systemic administration of probenecid decreases alcohol self-administration in alcohol dependent but not in nondependent alcohol self-administering rats. "*" means different from vehicle-treated dependent rats ($p<0.05$, $n=6-8$).

Results in rats showed that carbenoxolone effectively and dose-dependently reduces responding (lever pressing) for alcohol both in dependent and nondependent rats (FIGS. 1A and 1B). At the highest dose of carbenoxolone used, 40 mg/kg, carbenoxolone did not affect responding for saccharin (FIG. 2B). Carbenoxolone also reduced alcohol drinking in mice in the CIE paradigm (FIG. 3A) and in the DID paradigm of binge drinking (FIG. 3B).

These results indicate that carbenoxolone can be beneficial in two separate stages of alcohol abuse progression, the early stage when alcohol's positive reinforcement predominates and after the insurgence of dependence, when negative reinforcement becomes predominant (120).

Carbenoxolone inhibits both isozymes of 11β-HSD (11). Inhibition of 11β-HSD type 1 (11β-HSD1), which is expressed in liver and adipose tissue, reduces the intracellular availability of active glucocorticoids such as cortisol in humans and corticosterone in rodents (8). For this reason, 11β-HSD1 is characterized as a glucocorticoid pre-receptor (121). Carbenoxolone does not effectively cross the blood brain barrier (BBB), thus its actions in reducing alcohol drinking are likely due to its peripheral actions (122). Therefore, the present results suggest a role of peripheral glucocorticoid receptor activation in motivation for alcohol.

Although carbenoxolone has long been used in the clinic for treating gastritis and peptic ulcer, its use has greatly diminished in favor of other classes of drugs, such as proton pump inhibitors and histamine H2 antagonists. This is in part because of the potential of chronic carbenoxolone intake to induce pseudohyperaldosteronism. The latter is due to carbenoxolone inhibition of 11β-HSD type 2 isoform (11β-HSD2), present in the kidney and other mineralocorticoid target tissues, that performs the reverse reaction as 11β-HSD1, preventing glucocorticoids from acting on the mineralocorticoid receptor in cells that express it (26). Thus 11β-HSD2 inhibition results in the activation of mineralocorticoid receptors (MR) by glucocorticoids (26). However, this side effect of 11β-HSD inhibitors can be avoided by use of 11β-HSD1-selective inhibitors or by combination of non-selective 11β-HSD inhibitors with an anti-kaliuretic-diuretic, such as amiloride (20).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the spirit and scope of the invention. More specifically, the described embodiments are to be considered in all respects only as illustrative and not restrictive.

All similar substitutes and modifications apparent to those skilled in the art are deemed to be within the spirit and scope of the invention as defined by the appended claims.

All patents, patent applications, and publications mentioned in the specification are indicative of the levels of those of ordinary skill in the art to which the invention pertains. All patents, patent applications, and publications, including those to which priority or another benefit is claimed, are herein incorporated by reference to the same extent as if each individual publication was specifically and individually indicated to be incorporated by reference.

The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. The terms and expressions which have been employed are used as terms of description and not of limitation, and there is no intention that use of such terms and expressions imply excluding any equivalents of the features shown and described in whole or in part thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

REFERENCES

1. SAMHSA. 2013. Results from the 2012 National Survey on Drug Use and Health: Summary of National Findings, NSDUH Series H-46, HHS Publication No. (SMA) 13-4795. Rockville, Md.: Substance Abuse and Mental Health Services Administration, 2013.
2. Berrettini W. 2013. Opioid pharmacogenetics of alcohol addiction. Cold Spring Harb Perspect Med 3.
3. Mason B J, Quello S, Goodell V, Shadan F, Kyle M, Begovic A. 2013. Gabapentin Treatment for Alcohol Dependence: A Randomized Clinical Trial. JAMA Intern Med doi:10.1001/jamainternmed.2013.11950.
4. Mason B J, Lehert P. 2012. Acamprosate for alcohol dependence: a sex-specific meta-analysis based on individual patient data. Alcohol Clin Exp Res 36:497-508.
5. Litten R Z, Egli M, Heilig M, Cui C, Fertig J B, Ryan M L, Falk D E, Moss H, Huebner R, Noronha A. 2012. Medications development to treat alcohol dependence: a vision for the next decade. Addict Biol 17:513-527.
6. Scott J S, Goldberg F W, Turnbull A V. 2013. Medicinal Chemistry of Inhibitors of 11beta-Hydroxysteroid Dehydrogenase Type 1 (11beta-HSD1). J Med Chem doi: 10.1021/jm4014746.
7. Bertaccini G, Coruzzi G. 1985. Pharmacology of the treatment of peptic ulcer disease. Dig Dis Sci 30:43S-51S.
8. Chapman K, Holmes M, Seckl J. 2013. 11beta-hydroxysteroid dehydrogenases: intracellular gate-keepers of tissue glucocorticoid action. Physiol Rev 93:1139-1206.
9. Andrews R C, Rooyackers O, Walker B R. 2003. Effects of the 11 beta-hydroxysteroid dehydrogenase inhibitor carbenoxolone on insulin sensitivity in men with type 2 diabetes. J Clin Endocrinol Metab 88:285-291.
10. Baker M E. 2010. Evolution of 11beta-hydroxysteroid dehydrogenase-type 1 and 11beta-hydroxysteroid dehydrogenase-type 3. FEBS Lett 584:2279-2284.
11. Stewart P M, Wallace A M, Atherden S M, Shearing C H, Edwards C R. 1990. Mineralocorticoid activity of carbenoxolone: contrasting effects of carbenoxolone and liquorice on 11 beta-hydroxysteroid dehydrogenase activity in man. Clin Sci (Lond) 78:49-54.
12. Piazza P V, Le Moal M. 1997. Glucocorticoids as a biological substrate of reward: physiological and pathophysiological implications [In Process Citation]. Brain Res Brain Res Rev 25:359-372.
13. Vendruscolo L F, Barbier E, Schlosburg J E, Misra K K, Whitfield T W, Jr., Logrip M L, Rivier C, Repunte-Canonigo V, Zorrilla E P, Sanna P P, Heilig M, Koob G F. 2012. Corticosteroid-dependent plasticity mediates compulsive alcohol drinking in rats. J Neurosci 32:7563-7571.
14. Vendruscolo L F, Estey D, Goodell V, Macshane L G, Logrip M L, Schlosburg J E, McGinn M A, Zamora-Martinez E R, Belanoff J K, Hunt H J, Sanna P P, George O, Koob G F, Edwards S, Mason B J. 2015. Glucocorticoid receptor antagonism decreases alcohol seeking in alcohol-dependent individuals. J Clin Invest doi:10.1172/JCI79828.
15. Nuotio-Antar A M, Hachey D L, Hasty A H. 2007. Carbenoxolone treatment attenuates symptoms of metabolic syndrome and atherogenesis in obese, hyperlipidemic mice. Am J Physiol Endocrinol Metab 293:E1517-1528.
16. Prasad Sakamuri S S, Sukapaka M, Prathipati V K, Nemani H, Putcha U K, Pothana S, Koppala S R, Ponday L R, Acharya V, Veetill G N, Ayyalasomayajula V. 2012. Carbenoxolone treatment ameliorated metabolic syndrome in WNIN/Ob obese rats, but induced severe fat loss and glucose intolerance in lean rats. PLoS One 7:e50216.
17. Walker B R, Andrew R. 2006. Tissue production of cortisol by 11beta-hydroxysteroid dehydrogenase type 1 and metabolic disease. Ann NY Acad Sci 1083:165-184.
18. Walker B R, Connacher A A, Lindsay R M, Webb D J, Edwards C R. 1995. Carbenoxolone increases hepatic insulin sensitivity in man: a novel role for 11-oxosteroid reductase in enhancing glucocorticoid receptor activation. J Clin Endocrinol Metab 80:3155-3159.
19. Mohler E G, Browman K E, Roderwald V A, Cronin E A, Markosyan S, Scott Bitner R, Strakhova M I, Drescher K U, Hornberger W, Rohde J J, Brune M E, Jacobson P B, Rueter L E. 2011. Acute inhibition of 11beta-hydroxysteroid dehydrogenase type-1 improves memory in rodent models of cognition. J Neurosci 31:5406-5413.

20. Sandeep T C, Yau J L, MacLullich A M, Noble J, Deary I J, Walker B R, Seckl J R. 2004. 11Beta-hydroxysteroid dehydrogenase inhibition improves cognitive function in healthy elderly men and type 2 diabetics. Proc Natl Acad Sci USA 101:6734-6739.
21. Odermatt A, Kratschmar D V. 2012. Tissue-specific modulation of mineralocorticoid receptor function by 11beta-hydroxysteroid dehydrogenases: an overview. Mol Cell Endocrinol 350:168-186.
22. Cottrell E C, Seckl J R, Holmes M C, Wyrwoll C S. 2013. Foetal and placental 11beta-HSD2: a hub for developmental programming. Acta Physiol (Oxf) doi:10.1111/apha.12187.
23. Wyrwoll C S, Kerrigan D, Holmes M C, Seckl J R, Drake A J. 2012. Altered placental methyl donor transport in the dexamethasone programmed rat. Placenta 33:220-223.
24. Wyrwoll C S, Seckl J R, Holmes M C. 2009. Altered placental function of 11beta-hydroxysteroid dehydrogenase 2 knockout mice. Endocrinology 150:1287-1293.
25. Ferrari P. 2010. The role of 11beta-hydroxysteroid dehydrogenase type 2 in human hypertension. Biochim Biophys Acta 1802:1178-1187.
26. Armanini D, Calo L, Semplicini A. 2003. Pseudohyperaldosteronism: pathogenetic mechanisms. Crit Rev Clin Lab Sci 40:295-335.
27. Armanini D, Karbowiak I, Krozowski Z, Funder J W, Adam W R. 1982. The mechanism of mineralocorticoid action of carbenoxolone. Endocrinology 111:1683-1686.
28. Armanini D, Scali M, Zennaro M C, Karbowiak I, Wallace C, Lewicka S, Vecsei P, Mantero F. 1989. The pathogenesis of pseudohyperaldosteronism from carbenoxolone. J Endocrinol Invest 12:337-341.
29. Chantong B, Kratschmar D V, Nashev L G, Balazs Z, Odermatt A. 2012. Mineralocorticoid and glucocorticoid receptors differentially regulate NF-kappaB activity and pro-inflammatory cytokine production in murine BV-2 microglial cells. J Neuroinflammation 9:260.
30. Zhang M Z, Xu J, Yao B, Yin H, Cai Q, Shrubsole M J, Chen X, Kon V, Zheng W, Pozzi A, Harris R C. 2009. Inhibition of 11beta-hydroxysteroid dehydrogenase type II selectively blocks the tumor COX-2 pathway and suppresses colon carcinogenesis in mice and humans. J Clin Invest 119:876-885.
31. Farese S, Kruse A, Pasch A, Dick B, Frey B M, Uehlinger D E, Frey F J. 2009. Glycyrrhetinic acid food supplementation lowers serum potassium concentration in chronic hemodialysis patients. Kidney Int 76:877-884.
32. Richardson H N, Lee S Y, O'Dell L E, Koob G F, Rivier C L. 2008. Alcohol self-administration acutely stimulates the hypothalamic-pituitary-adrenal axis, but alcohol dependence leads to a dampened neuroendocrine state. Eur J Neurosci 28:1641-1653.
33. Rasmussen D D, Boldt B M, Bryant C A, Mitton D R, Larsen S A, Wilkinson C W. 2000. Chronic daily ethanol and withdrawal: 1. Long-term changes in the hypothalamo-pituitary-adrenal axis. Alcohol Clin Exp Res 24:1836-1849.
34. Adinoff B, Ruether K, Krebaum S, Iranmanesh A, Williams M J. 2003. Increased salivary cortisol concentrations during chronic alcohol intoxication in a naturalistic clinical sample of men. Alcohol Clin Exp Res 27:1420-1427.
35. Lovallo W R, Dickensheets S L, Myers D A, Thomas T L, Nixon S J. 2000. Blunted stress cortisol response in abstinent alcoholic and polysubstance-abusing men. Alcohol Clin Exp Res 24:651-658.
36. Uhart M, Wand G S. 2009. Stress, alcohol and drug interaction: an update of human research. Addict Biol 14:43-64.
37. Sinha R, Fox H C, Hong K I, Hansen J, Tuit K, Kreek M J. 2011. Effects of adrenal sensitivity, stress- and cue-induced craving, and anxiety on subsequent alcohol relapse and treatment outcomes. Arch Gen Psychiatry 68:942-952.
38. Heilig M, Goldman D, Berrettini W, O'Brien C P. 2011. Pharmacogenetic approaches to the treatment of alcohol addiction. Nat Rev Neurosci 12:670-684.
39. Turpie A G, Thomson T J. 1965. Carbenoxolone sodium in the treatment of gastric ulcer with special reference to side-effects. Gut 6:591-594.
40. Classen-Houben D, Schuster D, Da Cunha T, Odermatt A, Wolber G, Jordis U, Kueenburg B. 2009. Selective inhibition of 11beta-hydroxysteroid dehydrogenase 1 by 18alpha-glycyrrhetinic acid but not 18beta-glycyrrhetinic acid. J Steroid Biochem Mol Biol 113:248-252.
41. Beseda I, Czollner L, Shah P S, Khunt R, Gaware R, Kosma P, Stanetty C, Del Ruiz-Ruiz M C, Amer H, Mereiter K, Da Cunha T, Odermatt A, Classen-Houben D, Jordis U. 2010. Synthesis of glycyrrhetinic acid derivatives for the treatment of metabolic diseases. Bioorg Med Chem 18:433-454.
42. Kratschmar D V, Vuorinen A, Da Cunha T, Wolber G, Classen-Houben D, Doblhoff O, Schuster D, Odermatt A. 2011. Characterization of activity and binding mode of glycyrrhetinic acid derivatives inhibiting 11beta-hydroxysteroid dehydrogenase type 2. J Steroid Biochem Mol Biol 125:129-142.
43. Stanetty C, Czollner L, Koller I, Shah P, Gaware R, Cunha T D, Odermatt A, Jordis U, Kosma P, Classen-Houben D. 2010. Synthesis of novel 3-amino and 29-hydroxamic acid derivatives of glycyrrhetinic acid as selective 11beta-hydroxysteroid dehydrogenase 2 inhibitors. Bioorg Med Chem 18:7522-7541.
44. Gaware R, Khunt R, Czollner L, Stanetty C, Da Cunha T, Kratschmar D V, Odermatt A, Kosma P, Jordis U, Classen-Houben D. 2011. Synthesis of new glycyrrhetinic acid derived ring A azepanone, 29-urea and 29-hydroxamic acid derivatives as selective 11beta-hydroxysteroid dehydrogenase 2 inhibitors. Bioorg Med Chem 19:1866-1880.
45. Zhang Y D, Lorenzo B, Reidenberg M M. 1994. Inhibition of 11 beta-hydroxysteroid dehydrogenase obtained from guinea pig kidney by furosemide, naringenin and some other compounds. J Steroid Biochem Mol Biol 49:81-85.
46. Pandya K, Dietrich D, Seibert J, Vederas J C, Odermatt A. 2013. Synthesis of sterically encumbered 11beta-aminoprogesterone derivatives and evaluation as 11beta-hydroxysteroid dehydrogenase inhibitors and mineralocorticoid receptor antagonists. Bioorg Med Chem 21:6274-6281.
47. Hofer S, Kratschmar D V, Schernthanner B, Vuorinen A, Schuster D, Odermatt A, Easmon J. 2013. Synthesis and biological analysis of benzazol-2-yl piperazine sulfonamides as 11beta-hydroxysteroid dehydrogenase 1 inhibitors. Bioorg Med Chem Lett 23:5397-5400.
48. Alberts P, Engblom L, Edling N, Forsgren M, Klingstrom G, Larsson C, Ronquist-Nii Y, Ohman B, Abrahmsen L. 2002. Selective inhibition of 11beta-hydroxysteroid dehydrogenase type 1 decreases blood glucose concentrations in hyperglycaemic mice. Diabetologia 45:1528-1532.

49. Schuster D, Maurer E M, Laggner C, Nashev L G, Wilckens T, Langer T, Odermatt A. 2006. The discovery of new 11beta-hydroxysteroid dehydrogenase type 1 inhibitors by common feature pharmacophore modeling and virtual screening. J Med Chem 49:3454-3466.
50. Sun D, Wang M, Wang Z. 2011. Small molecule 11beta-hydroxysteroid dehydrogenase type 1 inhibitors. Curr Top Med Chem 11:1464-1475.
51. Tiwari A. 2010. INCB-13739, an 11beta-hydroxysteroid dehydrogenase type 1 inhibitor for the treatment of type 2 diabetes. IDrugs 13:266-275.
52. Hale C, Wang M. 2008. Development of 11beta-HSD1 inhibitors for the treatment of type 2 diabetes. Mini Rev Med Chem 8:702-710.
53. Wamil M, Seckl J R. 2007. Inhibition of 11beta-hydroxysteroid dehydrogenase type 1 as a promising therapeutic target. Drug Discov Today 12:504-520.
54. Wyrwoll C S, Holmes M C, Seckl J R. 2011. 11beta-hydroxysteroid dehydrogenases and the brain: from zero to hero, a decade of progress. Front Neuroendocrinol 32:265-286.
55. Barf T, Vallgarda J, Emond R, Haggstrom C, Kurz G, Nygren A, Larwood V, Mosialou E, Axelsson K, Olsson R, Engblom L, Edling N, Ronquist-Nii Y, Ohman B, Alberts P, Abrahmsen L. 2002. Arylsulfonamidothiazoles as a new class of potential antidiabetic drugs. Discovery of potent and selective inhibitors of the 11beta-hydroxysteroid dehydrogenase type 1. J Med Chem 45:3813-3815.
56. Flyren K, Bergquist L O, Castro V M, Fotsch C, Johansson L, St Jean D J, Jr., Sutin L, Williams M. 2007. Piperidine amides as 11beta-hydroxysteroid dehydrogenase type 1 inhibitors. Bioorg Med Chem Lett 17:3421-3425.
57. Sutin L, Andersson S, Bergquist L, Castro V M, Danielsson E, James S, Henriksson M, Johansson L, Kaiser C, Flyren K, Williams M. 2007. Oxazolones as potent inhibitors of 11beta-hydroxysteroid dehydrogenase type 1. Bioorg Med Chem Lett 17:4837-4840.
58. Fotsch C, Bartberger M D, Bercot E A, Chen M, Cupples R, Emery M, Fretland J, Guram A, Hale C, Han N, Hickman D, Hungate R W, Hayashi M, Komorowski R, Liu Q, Matsumoto G, St Jean D J, Jr., Ursu S, Veniant M, Xu G, Ye Q, Yuan C, Zhang J, Zhang X, Tu H, Wang M. 2008. Further studies with the 2-amino-1,3-thiazol-4(5H)-one class of 11beta-hydroxysteroid dehydrogenase type 1 inhibitors: reducing pregnane X receptor activity and exploring activity in a monkey pharmacodynamic model. J Med Chem 51:7953-7967.
59. Hale C, Veniant M, Wang Z, Chen M, McCormick J, Cupples R, Hickman D, Min X, Sudom A, Xu H, Matsumoto G, Fotsch C, St Jean D J, Jr., Wang M. 2008. Structural characterization and pharmacodynamic effects of an orally active 11beta-hydroxysteroid dehydrogenase type 1 inhibitor. Chem Biol Drug Des 71:36-44.
60. Jean D J, Jr., Yuan C, Bercot E A, Cupples R, Chen M, Fretland J, Hale C, Hungate R W, Komorowski R, Veniant M, Wang M, Zhang X, Fotsch C. 2007. 2-(S)-phenethyl-aminothiazolones as potent, orally efficacious inhibitors of 11beta-hydroxysteriod dehydrogenase type 1. J Med Chem 50:429-432.
61. Veniant M M, Hale C, Hungate R W, Gahm K, Emery M G, Jona J, Joseph S, Adams J, Hague A, Moniz G, Zhang J, Bartberger M D, Li V, Syed R, Jordan S, Komorowski R, Chen M M, Cupples R, Kim K W, St Jean D J, Jr., Johansson L, Henriksson M A, Williams M, Vallgarda J, Fotsch C, Wang M. 2010. Discovery of a potent, orally active 11beta-hydroxysteroid dehydrogenase type 1 inhibitor for clinical study: identification of (S)-2-((1S,2S,4R)-bicyclo[2.2.1]heptan-2-ylamino)-5-isopropyl-5-methylthiazol-4(5H)-one (AMG 221). J Med Chem 53:4481-4487.
62. Zhu X, Slatter J G, Emery M G, Deane M R, Akrami A, Zhang X, Hickman D, Skiles G L, Subramanian R. 2013. Activity-based exposure comparisons among humans and nonclinical safety testing species in an extensively metabolized drug candidate. Xenobiotica 43:617-627.
63. Sun D, Wang Z, Di Y, Jaen J C, Labelle M, Ma J, Miao S, Sudom A, Tang L, Tomooka C S, Tu H, Ursu S, Walker N, Yan X, Ye Q, Powers J P. 2008. Discovery and initial SAR of arylsulfonylpiperazine inhibitors of 11beta-hydroxysteroid dehydrogenase type 1 (11beta-HSD1). Bioorg Med Chem Lett 18:3513-3516.
64. Julian L D, Wang Z, Bostick T, Caille S, Choi R, DeGraffenreid M, Di Y, He X, Hungate R W, Jaen J C, Liu J, Monshouwer M, McMinn D, Rew Y, Sudom A, Sun D, Tu H, Ursu S, Walker N, Yan X, Ye Q, Powers J P. 2008. Discovery of novel, potent benzamide inhibitors of 11beta-hydroxysteroid dehydrogenase type 1 (11beta-HSD1) exhibiting oral activity in an enzyme inhibition ex vivo model. J Med Chem 51:3953-3960.
65. Yan X, Wang Z, Sudom A, Cardozo M, DeGraffenreid M, Di Y, Fan P, He X, Jaen J C, Labelle M, Liu J, Ma J, McMinn D, Miao S, Sun D, Tang L, Tu H, Ursu S, Walker N, Ye Q, Powers J P. 2010. The synthesis and SAR of novel diarylsulfone 11beta-HSD1 inhibitors. Bioorg Med Chem Lett 20:7071-7075.
66. Rew Y, McMinn D L, Wang Z, He X, Hungate R W, Jaen J C, Sudom A, Sun D, Tu H, Ursu S, Villemure E, Walker N P, Yan X, Ye Q, Powers J P. 2009. Discovery and optimization of piperidyl benzamide derivatives as a novel class of 11beta-HSD1 inhibitors. Bioorg Med Chem Lett 19:1797-1801.
67. Sun D, Wang Z, Caille S, DeGraffenreid M, Gonzalez-Lopez de Turiso F, Hungate R, Jaen J C, Jiang B, Julian L D, Kelly R, McMinn D L, Kaizerman J, Rew Y, Sudom A, Tu H, Ursu S, Walker N, Willcockson M, Yan X, Ye Q, Powers J P. 2011. Synthesis and optimization of novel 4,4-disubstituted cyclohexylbenzamide derivatives as potent 11beta-HSD1 inhibitors. Bioorg Med Chem Lett 21:405-410.
68. Rew Y, DeGraffenreid M, He X, Jaen J C, McMinn D L, Sun D, Tu H, Ursu S, Powers J P. 2012. Discovery and optimization of benzenesulfonanilide derivatives as a novel class of 11beta-HSD1 inhibitors. Bioorg Med Chem Lett 22:3786-3790.
69. McMinn D L, Rew Y, Sudom A, Caille S, Degraffenreid M, He X, Hungate R, Jiang B, Jaen J, Julian L D, Kaizerman J, Novak P, Sun D, Tu H, Ursu S, Walker N P, Yan X, Ye Q, Wang Z, Powers J P. 2009. Optimization of novel di-substituted cyclohexylbenzamide derivatives as potent 11 beta-HSD1 inhibitors. Bioorg Med Chem Lett 19:1446-1450.
70. Hermanowski-Vosatka A, Balkovec J M, Cheng K, Chen H Y, Hernandez M, Koo G C, Le Grand C B, Li Z, Metzger J M, Mundt S S, Noonan H, Nunes C N, Olson S H, Pikounis B, Ren N, Robertson N, Schaeffer J M, Shah K, Springer M S, Strack A M, Strowski M, Wu K, Wu T, Xiao J, Zhang B B, Wright S D, Thieringer R. 2005. 11beta-HSD1 inhibition ameliorates metabolic syndrome and prevents progression of atherosclerosis in mice. J Exp Med 202:517-527.
71. Olson S, Aster S D, Brown K, Carbin L, Graham D W, Hermanowski-Vosatka A, LeGrand C B, Mundt S S, Robbins M A, Schaeffer J M, Slossberg L H, Szymonifka M J, Thieringer R, Wright S D, Balkovec J M. 2005. Adamantyl triazoles as selective inhibitors of 11beta-hydroxysteroid dehydrogenase type 1. Bioorg Med Chem Lett 15:4359-4362.
72. Aster S D, Graham D W, Kharbanda D, Patel G, Ponpipom M, Santorelli G M, Szymonifka M J, Mundt S S, Shah K, Springer M S, Thieringer R, Hermanowski-Vosatka A, Wright S D, Xiao J, Zokian H, Balkovec J M. 2008. Bis-aryl triazoles as selective inhibitors of 11beta-hydroxysteroid dehydrogenase type 1. Bioorg Med Chem Lett 18:2799-2804.
73. Zhu Y, Olson S H, Graham D, Patel G, Hermanowski-Vosatka A, Mundt S, Shah K, Springer M, Thieringer R, Wright S, Xiao J, Zokian H, Dragovic J, Balkovec J M. 2008. Phenylcyclobutyl triazoles as selective inhibitors of 11beta-hydroxysteroid dehydrogenase type I. Bioorg Med Chem Lett 18:3412-3416.
74. Zhu Y, Olson S H, Hermanowski-Vosatka A, Mundt S, Shah K, Springer M, Thieringer R, Wright S, Xiao J, Zokian H, Balkovec J M. 2008. 4-Methyl-5-phenyl triazoles as selective inhibitors of 11beta-hydroxysteroid dehydrogenase type I. Bioorg Med Chem Lett 18:3405-3411.
75. Sun W, Maletic M, Mundt S S, Shah K, Zokian H, Lyons K, Waddell S T, Balkovec J. 2011. Substituted phenyl triazoles as selective inhibitors of 11beta-Hydroxysteroid Dehydrogenase Type 1. Bioorg Med Chem Lett 21:2141-2145.
76. Gu X, Dragovic J, Koo C, Koprak L, LeGrand C, Mundt S S, Shah K, Springer M S, Tan E Y, Thieringer R, Hermanowski-Vosatka A, Zokian H J, Balkovec J M, Waddell S T. 2005. Discovery of 4-heteroarylbicyclo[2.2.2]octyltriazoles as potent and selective inhibitors of 11beta-HSD1: novel therapeutic agents for the treatment of metabolic syndrome. Bioorg Med Chem Lett 15:5266-5269.
77. Maletic M, Leeman A, Szymonifka M, Mundt S S, Zokian H J, Shah K, Dragovic J, Lyons K, Thieringer R, Vosatka A H, Balkovec J, Waddell S T. 2011. Bicyclo[2.2.2]octyltriazole inhibitors of 11beta-hydoxysteroid dehydrogenase type 1. Pharmacological agents for the treatment of metabolic syndrome. Bioorg Med Chem Lett 21:2568-2572.
78. Shah U, Boyle C D, Chackalamannil S, Baker H, Kowalski T, Lee J, Terracina G, Zhang L. 2010. Azabicyclic sulfonamides as potent 11beta-HSD1 inhibitors. Bioorg Med Chem Lett 20:1551-1554.
79. Siu M, Johnson T O, Wang Y, Nair S K, Taylor W D, Cripps S J, Matthews J J, Edwards M P, Pauly T A, Ermolieff J, Castro A, Hosea N A, LaPaglia A, Fanjul A N, Vogel J E. 2009. N-(Pyridin-2-yl) arylsulfonamide inhibitors of 11beta-hydroxysteroid dehydrogenase type 1: Discovery of PF-915275. Bioorg Med Chem Lett 19:3493-3497.
80. Bhat B G, Hosea N, Fanjul A, Herrera J, Chapman J, Thalacker F, Stewart P M, Rejto P A. 2008. Demonstration of proof of mechanism and pharmacokinetics and pharmacodynamic relationship with 4'-cyano-biphenyl-4-sulfonic acid (6-amino-pyridin-2-yl)-amide (PF-915275), an inhibitor of 11-hydroxysteroid dehydrogenase type 1, in cynomolgus monkeys. J Pharmacol Exp Ther 324:299-305.
81. Rohde J J, Pliushchev M A, Sorensen B K, Wodka D, Shuai Q, Wang J, Fung S, Monzon K M, Chiou W J, Pan L, Deng X, Chovan L E, Ramaiya A, Mullally M, Henry R F, Stolarik D F, Imade H M, Marsh K C, Beno D W, Fey T A, Droz B A, Brune M E, Camp H S, Sham H L, Frevert E U, Jacobson P B, Link J T. 2007. Discovery and metabolic stabilization of potent and selective 2-amino-N-(adamant-2-yl) acetamide 11beta-hydroxysteroid dehydrogenase type 1 inhibitors. J Med Chem 50:149-164.
82. Nair S K, Matthews J J, Cripps S J, Cheng H, Hoffman J E, Smith C, Kupchinsky S, Siu M, Taylor W D, Wang Y, Johnson T O, Dress K R, Edwards M P, Zhou S, Hosea N A, Lapaglia A, Kang P, Castro A, Ermolieff J, Fanjul A, Vogel J E, Rejto P, Dalvie D. 2013. N-(Pyridin-2-yl) arylsulfonamide inhibitors of 11beta-hydroxysteroid dehydrogenase type 1: strategies to eliminate reactive metabolites. Bioorg Med Chem Lett 23:2344-2348.
83. Cheng H, Hoffman J, Le P, Nair S K, Cripps S, Matthews J, Smith C, Yang M, Kupchinsky S, Dress K, Edwards M, Cole B, Walters E, Loh C, Ermolieff J, Fanjul A, Bhat G B, Herrera J, Pauly T, Hosea N, Paderes G, Rejto P. 2010. The development and SAR of pyrrolidine carboxamide 11beta-HSD1 inhibitors. Bioorg Med Chem Lett 20:2897-2902.
84. Xiang J, Ipek M, Suri V, Massefski W, Pan N, Ge Y, Tam M, Xing Y, Tobin J F, Xu X, Tam S. 2005. Synthesis and biological evaluation of sulfonamidooxazoles and beta-keto sulfones: selective inhibitors of 11beta-hydroxysteroid dehydrogenase type I. Bioorg Med Chem Lett 15:2865-2869.
85. Xiang J, Wan Z K, Li H Q, Ipek M, Binnun E, Nunez J, Chen L, McKew J C, Mansour T S, Xu X, Suri V, Tam M, Xing Y, Li X, Hahm S, Tobin J, Saiah E. 2008. Piperazine sulfonamides as potent, selective, and orally available 11beta-hydroxysteroid dehydrogenase type 1 inhibitors with efficacy in the rat cortisone-induced hyperinsulinemia model. J Med Chem 51:4068-4071.
86. Wan Z K, Chenail E, Li H Q, Kendall C, Wang Y, Gingras S, Xiang J, Massefski W W, Mansour T S, Saiah E. 2011. Synthesis of potent and orally efficacious 11beta-hydroxysteroid dehydrogenase type 1 inhibitor HSD-016. J Org Chem 76:7048-7055.
87. Wan Z K, Chenail E, Xiang J, Li H Q, Ipek M, Bard J, Svenson K, Mansour T S, Xu X, Tian X, Suri V, Hahm S, Xing Y, Johnson C E, Li X, Qadri A, Panza D, Perreault M, Tobin J F, Saiah E. 2009. Efficacious 11beta-hydroxysteroid dehydrogenase type I inhibitors in the diet-induced obesity mouse model. J Med Chem 52:5449-5461.
88. Wan Z, Chenail E, Li H, Ipek M, Xiang J, Suri V, Hahm S, Bard J, Svenson K, Xu X, Tian X, Wang M, Li X, Johnson C E, Qadri A, Panza D, Perreault M, Mansour T S, Tobin J F, Saiah E. 2013. Discovery of HSD-621 as a potential agent for the treatment of type 2 diabetes. ACS Med Chem Lett 4:118-123.
89. Scott J S, Bowker S S, Deschoolmeester J, Gerhardt S, Hargreaves D, Kilgour E, Lloyd A, Mayers R M, McCoull W, Newcombe N J, Ogg D, Packer M J, Rees A, Revill J, Schofield P, Selmi N, Swales J G, Whittamore P R. 2012. Discovery of a potent, selective, and orally bioavailable acidic 11beta-hydroxysteroid dehydrogenase type 1 (11beta-HSD1) inhibitor: discovery of 2-[(3S)-1-[5-(cyclohexylcarbamoyl)-6-propylsulfanylpyridin-2-yl]-3-piperidyl]acetic acid (AZD4017). J Med Chem 55:5951-5964.
90. Scott J S, Gill A L, Godfrey L, Groombridge S D, Rees A, Revill J, Schofield P, Sorme P, Stocker A, Swales J G, Whittamore P R. 2012. Optimisation of pharmacokinetic properties in a neutral series of 11beta-HSD1 inhibitors. Bioorg Med Chem Lett 22:6756-6761.

91. Goldberg F W, Leach A G, Scott J S, Snelson W L, Groombridge S D, Donald C S, Bennett S N, Bodin C, Gutierrez P M, Gyte A C. 2012. Free-Wilson and structural approaches to co-optimizing human and rodent isoform potency for 11beta-hydroxysteroid dehydrogenase type 1 (11beta-HSD1) inhibitors. J Med Chem 55:10652-10661.

92. Scott J S, Barton P, Bennett S N, deSchoolmeester J, Godfrey L, Kilgour E, Mayers R M, Packer M J, Rees A, Schofield P, Selmi N, Swales J G, Whittamore P R O. 2012. Reduction of acyl glucuronidation in a series of acidic 11β-hydroxysteroid dehydrogenase type 1 (11β-HSD1) inhibitors: the discovery of AZD6925. MedChemComm 3.

93. McCoull W, Augustin M, Blake C, Ertan A, Kilgour E, Krapp S, Moore J E, Newcombe N J, Packer M J, Rees A, Revill J, Scott J S, Selmi N, Gerhardt S, Ogg D J, Steinbacher S, Whittamore P R. 2013. Identification and optimisation of 3,3-dimethyl-azetidin-2-ones as potent and selective inhibitors of 11β-hydroxysteroid dehydrogenase type 1 (11β-HSD1). MedChemComm [Online early access] DOI: 101039/C3MD00234A published online: Nov. 6, 2013.

94. Scott J S, deSchoolmeester J, Kilgour E, Mayers R M, Packer M J, Hargreaves D, Gerhardt S, Ogg D J, Rees A, Selmi N, Stocker A, Swales J G, Whittamore P R. 2012. Novel acidic 11beta-hydroxysteroid dehydrogenase type 1 (11beta-HSD1) inhibitor with reduced acyl glucuronide liability: the discovery of 4-[4-(2-adamantylcarbamoyl)-5-tert-butyl-pyrazol-1-yl]benzoic acid (AZD8329). J Med Chem 55:10136-10147.

95. Coppola G M, Kukkola P J, Stanton J L, Neubert A D, Marcopulos N, Bilci N A, Wang H, Tomaselli H C, Tan J, Aicher T D, Knorr D C, Jeng A Y, Dardik B, Chatelain R E. 2005. Perhydroquinolylbenzamides as novel inhibitors of 11beta-hydroxysteroid dehydrogenase type 1. J Med Chem 48:6696-6712.

96. Duan X, Xin H, Yan H. 2014. Design, synthesis, and biological evaluation of 1,4-diaryl-1,4-dihydropyrazines as novel 11beta-HSD1 inhibitors. Biol Pharm Bull 37:840-846.

97. Su X, Lawrence H, Ganeshapillai D, Cruttenden A, Purohit A, Reed M J, Vicker N, Potter B V. 2004. Novel 18beta-glycyrrhetinic acid analogues as potent and selective inhibitors of 11beta-hydroxysteroid dehydrogenases. Bioorg Med Chem 12:4439-4457.

98. Vicker N, Su X, Lawrence H, Cruttenden A, Purohit A, Reed M J, Potter B V. 2004. A novel 18 beta-glycyrrhetinic acid analogue as a potent and selective inhibitor of 11 beta-hydroxysteroid dehydrogenase 2. Bioorg Med Chem Lett 14:3263-3267.

99. Su X, Vicker N, Lawrence H, Smith A, Purohit A, Reed M J, Potter B V. 2007. Inhibition of human and rat 11beta-hydroxysteroid dehydrogenase type 1 by 18beta-glycyrrhetinic acid derivatives. J Steroid Biochem Mol Biol 104:312-320.

100. Dahl G, Qiu F, Wang J. 2013. The bizarre pharmacology of the ATP release channel pannexin1. Neuropharmacology 75:583-593.

101. Silverman W, Locovei S, Dahl G. 2008. Probenecid, a gout remedy, inhibits pannexin 1 channels. Am J Physiol Cell Physiol 295:C761-767.

102. Silverman W R, de Rivero Vaccari J P, Locovei S, Qiu F, Carlsson S K, Scemes E, Keane R W, Dahl G. 2009. The pannexin 1 channel activates the inflammasome in neurons and astrocytes. J Biol Chem 284:18143-18151.

103. Wang J, Ma M, Locovei S, Keane R W, Dahl G. 2007. Modulation of membrane channel currents by gap junction protein mimetic peptides: size matters. Am J Physiol Cell Physiol 293:C1112-1119.

104. Bruzzone R, Barbe M T, Jakob N J, Monyer H. 2005. Pharmacological properties of homomeric and heteromeric pannexin hemichannels expressed in Xenopus oocytes. J Neurochem 92:1033-1043.

105. Qiu F, Dahl G. 2009. A permeant regulating its permeation pore: inhibition of pannexin 1 channels by ATP. Am J Physiol Cell Physiol 296:C250-255.

106. Jo S, Bean B P. 2011. Inhibition of neuronal voltage-gated sodium channels by brilliant blue G. Mol Pharmacol 80:247-257.

107. Di Stefano A, Wittner M, Schlatter E, Lang H J, Englert H, Greger R. 1985. Diphenylamine-2-carboxylate, a blocker of the Cl(−)-conductive pathway in Cl(−)-transporting epithelia. Pflugers Arch 405 Suppl 1:S95-100.

108. Gilpin N W, Smith A D, Cole M, Weiss F, Koob G F, Richardson H N. 2009. Operant behavior and alcohol levels in blood and brain of alcohol-dependent rats. Alcohol Clin Exp Res 33:2113-2123.

109. Rimondini R, Sommer W, Heilig M. 2003. A temporal threshold for induction of persistent alcohol preference: behavioral evidence in a rat model of intermittent intoxication. J Stud Alcohol 64:445-449.

110. Roberts A J, Heyser C J, Cole M, Griffin P, Koob G F. 2000. Excessive ethanol drinking following a history of dependence: animal model of allostasis. Neuropsychopharmacology 22:581-594.

111. Schulteis G, Markou A, Cole M, Koob G F. 1995. Decreased brain reward produced by ethanol withdrawal. Proc Natl Acad Sci 92:5880-5884.

112. Becker H C, Lopez M F. 2004. Increased ethanol drinking after repeated chronic ethanol exposure and withdrawal experience in C57BL/6 mice. Alcohol Clin Exp Res 28:1829-1838.

113. Lopez M F, Becker H C. 2005. Effect of pattern and number of chronic ethanol exposures on subsequent voluntary ethanol intake in C57BL/6J mice. Psychopharmacology (Berl) 181:688-696.

114. Rhodes J S, Best K, Belknap J K, Finn D A, Crabbe J C. 2005. Evaluation of a simple model of ethanol drinking to intoxication in C57BL/6J mice. Physiol Behav 84:53-63.

115. Rhodes J S, Ford M M, Yu C H, Brown L L, Finn D A, Garland T, Jr., Crabbe J C. 2007. Mouse inbred strain differences in ethanol drinking to intoxication. Genes Brain Behav 6:1-18.

116. Sprow G M, Thiele T E. 2012. The neurobiology of binge-like ethanol drinking: Evidence from rodent models. Physiol Behav doi:10.1016/j.physbeh.2011.12.026.

117. Beraki S, Litrus L, Soriano L, Monbureau M, To L K, Braithwaite S P, Nikolich K, Urfer R, Oksenberg D, Shamloo M. 2013. A pharmacological screening approach for discovery of neuroprotective compounds in ischemic stroke. PLoS One 8:e69233.

118. Gareri P, Condorelli D, Belluardo N, Russo E, Loiacono A, Barresi V, Trovato-Salinaro A, Mirone M B, Ferreri Ibbadu G, De Sarro G. 2004. Anticonvulsant effects of carbenoxolone in genetically epilepsy prone rats (GEPRs). Neuropharmacology 47:1205-1216.

119. Gareri P, Condorelli D, Belluardo N, Gratteri S, Ferreri G, Donato Di Paola E, De Sarro A, De Sarro G. 2004. Influence of carbenoxolone on the anticonvulsant efficacy of conventional antiepileptic drugs against audiogenic seizures in DBA/2 mice. Eur J Pharmacol 484:49-56.

120. Koob G F, Volkow N D. 2010. Neurocircuitry of addiction. Neuropsychopharmacology 35:217-238.
121. Draper N, Stewart P M. 2005. 11beta-hydroxysteroid dehydrogenase and the pre-receptor regulation of corticosteroid hormone action. J Endocrinol 186:251-271.
122. Leshchenko Y, Likhodii S, Yue W, Burnham W M, Perez Velazquez J L. 2006. Carbenoxolone does not cross the blood brain barrier: an HPLC study. BMC Neurosci 7:3.

What is claimed is:

1. A method of treating a mammal, optionally a human, in need thereof of with a medicament to reduce alcohol intake, comprising administering to the mammal an effective amount of a composition comprising at least one inhibitor of a pannexin, wherein the inhibitor is a compound selected from the group consisting of carbenoxolone, probenecid, and a salt of carbenoxolone or probenecid, respectively, to suppress the mammal's dependence or craving for alcohol, thereby reducing alcohol intake by the mammal.

2. A method according to claim 1 wherein the composition further comprises a carrier, optionally a pharmaceutically acceptable carrier.

3. A method according to claim 1 wherein the composition comprises probenecid or a salt thereof.

4. A method according to claim 1 wherein the composition is formulated for controlled release of the pannexin inhibitor.

5. A method according to claim 2 wherein the compound is:
  (a) carbenoxolone or a salt of carbenoxolone, and wherein the method further comprises administering to the mammal an effective amount of a second composition comprising a second agent capable of modulating 11β-HSD1 or 11β-HSD2 activity; or
  (b) probenecid or a salt of probenecid, and wherein the method further comprises administering to the mammal an effective amount of a second composition comprising a second agent capable of modulating 11β-HSD1 or 11β-HSD2 activity.

6. A method according to claim 5 wherein the second agent comprises amiloride (3,5-diamino-6-chloro-N-(diaminomethylene) pyrazinecarboxamide), or a salt thereof.

7. A method according to claim 5 wherein the second agent comprises amiloride-HCl.

8. A method according to claim 5 wherein the second agent comprises amiloride-monohydrochloride dihydrate.

9. A method according to claim 5 wherein the second agent comprises an aldosterone antagonist.

10. A method according to claim 5 wherein the second agent comprises an androstadiene-spiro-furan.

11. A method according to claim 5 wherein the second agent comprises spironolactone (17-hydroxy-7alpha-mercapto-3-oxo-17alpha-pregn-4-ene-21-carboxylic acid gamma-lactone) or a salt thereof, optionally spironolactone-acetate or Eplerenone.

12. A method according to claim 5 wherein the first and/or second composition comprises a slow-release formulation.

13. A method according to claim 5 wherein the first and second agents are formulated as a single composition.

14. A method according to claim 13 wherein the single composition provides controlled release of the first and second agents.

15. A method according to claim 1 wherein the composition comprises carbenoxolone or a salt thereof.

* * * * *